US007619057B2

(12) United States Patent
Wang et al.

(10) Patent No.: US 7,619,057 B2
(45) Date of Patent: Nov. 17, 2009

(54) MHC CLASS II RESTRICTED T CELL EPITOPES FROM THE CANCER ANTIGEN, NY ESO-1

(75) Inventors: Rong-Fu Wang, Houston, TX (US); Steven A Rosenberg, Potomac, MD (US); Gang Zeng, Germantown, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 528 days.

(21) Appl. No.: 10/182,506

(22) PCT Filed: Jan. 26, 2001

(86) PCT No.: PCT/US01/02765

§ 371 (c)(1),
(2), (4) Date: Oct. 28, 2002

(87) PCT Pub. No.: WO01/55393

PCT Pub. Date: Aug. 2, 2001

(65) Prior Publication Data

US 2005/0136402 A1 Jun. 23, 2005

(51) Int. Cl.
*C07K 5/10* (2006.01)
(52) U.S. Cl. ...................... 530/300; 530/327
(58) Field of Classification Search .................. None
See application file for complete search history.

(56) References Cited

U.S. PATENT DOCUMENTS 5,840,839 A * 11/1998 Wang et al. ............. 530/325

FOREIGN PATENT DOCUMENTS

| WO | WO 99/18206 | * | 4/1999 |
| WO | WO99/18206 A2 | | 4/1999 |
| WO | WO99/47641 A1 | | 9/1999 |
| WO | WO99/53938 A1 | | 10/1999 |
| WO | WO00/00824 A1 | | 1/2000 |
| WO | WO01/23560 A2 | | 4/2001 |
| WO | WO01/36453 A2 | | 5/2001 |

OTHER PUBLICATIONS

Wang et al (1998, J. Immunol 161(7):3596-606).*
Zeng et al. (2001, Proc. Natl. Acad. Sci. 98(7):3964-3969).*
Johnstone and Thorpe (Immunochemistry in Practice, 2nd Ed. 1987, Blackwell Scientific Publications, Oxford, p. 30 and pp. 49-50).*
(Khong et al., 2004, J. Immunother. 27(6):472-477) (p. 477).*
Spitler (Cancer Biotherapy, 1995, 10:1-3).*
Ezzell (J. NIH Res, 1995, 7:46-49).*
Chaux et al, Int J Cancer, 1998, 77: 538-542.*
Kirkin et al, (1998, APMIS 106:665-679).*
Boon (Adv Can Res, 1992, 58:177-210).*
Smith RT, 1994, Clin Immunol, 41(4): 841-849.*
Roitt et al, Immunology, Fourth Edition, 1996, Mosby, p. 7.9-7.11.*
Ben-Efraim, Tumor Biology 1999; 20: 1-24.*
Marincola et al., TRENDS in Immunology 2003; 24: 334-341.*
Frazer, I., Expert. Opin. Pharmacother. 2004; 5: 2427-2434.*
Dong et al, J Immunol, 1995, 154:4536-4545.*
Gebe et al, Tissue Antigens, 2002, 59:78-87.*
Acsadi et al., *Nature*, 352, 815-818 (1991).
Bloom et al., *J. Exp. Med.*, 185, 453-460 (1997).
Bowne et al., *J. Exp. Med.*, 190, 1717-1722 (1999).
Chaux et al., *J. Exp. Med.*, 189, 767-778 (1999).
Chen et al., *PNAS*, 94, 1914-1918 (1997).
Chen et al., *Cancer J. Sci. Am.*, 5(1), 16-17 (1999).
Cooney et al., *Lancet*, 337, 567-572 (1991).
Davis et al., *Hum. Gene Ther.*, 4, 151-159 (1993).
Eisenbraum et al., *DNA and Cell Bio.*, 12, 791-797 (1993).
Fuller et al., *AIDS Res. Hum. Retrovir.*, 10(11), 1433-1441 (1994).
Futaki et al., *Immunogenetics*, 42(4), 299-301 (1995).
Fynan et al., *Proc. Natl. Acad. Sci.*, USA, 90, 11478-11482 (1995).
GENBANK Accession No. AF038567, *Homo sapiens* cancer antigen-3 and cancer antigen-3-ORF2 mRNA (Jan. 16, 1999).
GENBANK Accession No. AJ223040, *Homo sapiens* mRNA for LAGE-1b protein (Jun. 23, 1998).
GENBANK Accession No. AJ223041, *Homo sapiens* mRNA for LAGE-1a protein (Jun. 23, 1998).
GENBANK Accession No. AJ223093, *Homo sapiens* LAGE-1 gene (Jun. 23, 1998).
GENBANK Accession No. AAB49693, gi: 1890099, autoimmunogenic cancer/testis antigen NY-ESO-1 [*Home sapiens*] (Dec. 22, 1999).
Gjertson et al., *Population Studies*, P. Teraskai and D.W. Gjertson, editors; UCLA Tissue Typing Laboratory, LA, CA, 174-427 (1997).
Haas et al., *Am. J. Reprod.Immunuol. Microbiol.*, 18, 47-51 (1988).
Hara et al., *J. Exp. Med.*, 182, 1609-1614 (1995).
Houghton, *J. Exp. Med*, 180, 1-4 (1994).
Hung, *J. Exp. Med.*, 188, 2357-2368 (1998).
Ito et al., *J. Exp. Med.*, 183, 2635-2644 (1996).
Jager et al., *J. Exp. Med.*, 187(2), 265-270 (1998).
Jager et al., *International J. Cancer*, 84(5), 506-510 (1999).
Jager et al., *J. Exp. Med.*, 191(4), 625-630 (2000).
Kawakami et al., *J. Exp. Med.*, 168, 2183-2191 (1988).
Kawakami et al., *Proc. Natl. Acad. Sci.*, USA, 91, 3515-3519 (1994).
Kawakami et al., *Proc. Natl., Acad. Sci.*, USA, 91, 6458-6462 (1994).
Kawakami et al., *Imp. Adv. in Encology*, 3-21 (1996).
Lee et al., *Cancer J. Sci. Am.*, 5(1), 20-25 (1999).
Lethe et al., *Int. J. Cancer*, 76, 903-908 (1998).
Li et al., *Cancer Immunol. Immunother.*, 47, 32-38 (1998).

(Continued)

*Primary Examiner*—Misook Yu
*Assistant Examiner*—Mark Halvorson
(74) *Attorney, Agent, or Firm*—Leydig, Voit & Mayer

(57) ABSTRACT

The present invention discloses the identification and isolation of novel MHC class II epitopes derived from the cancer antigen, NY ESO-1. The novel MHC class II epitopes from NY-EsO-1 are recognized by CD4+ T lymphocytes in an HLA class II restricted manner, in particular HLA-DR or HLA-DP restricted. The products of the gene are promising candidates for immunotherapeutic strategies for the prevention, treatment and diagnosis of patients with cancer.

12 Claims, 17 Drawing Sheets

OTHER PUBLICATIONS

Manici et al., *J. Exp. Med.*, 189, 871-876 (1999).
Marchand et al., *Int. J. Cancer*, 80, 219-230 (1999).
Mumberg et al., *Proc. Natl. Acad. Sci.*, USA, 96, 8633-8638 (1999).
Nestle et al., *Nat. Med.*, 4, 328-332 (1998).
Old et al., *J. Exp. Med*, 187, 1163-1167 (1998).
Ossendorp et al., *J. Exp. Med.*, 187(5), 693-702 (1998).
Overwijk et al., *Proc. Natl. Acad. Sci.*, USA, 96, 2982-2987 (1999).
Pardoll et al., *Curr. Opin. Immunol.*, 10, 588-594 (1998).
Pieper et al., *J. Exp. Med.*, 189, 757-766 (1999).
Rammensee et al., *Immunogenetics*, 41, 178-228 (1995).
Riley et al., *Immunity*, 2, 533-543 (1995).
Robbins et al., *J. Exp. Med.*, 183, 1185-1192 (1995).
Rosenberg et al., *J. Immunother.*, 19, 81-84 (1996).
Rosenberg et al., *Immunity.*, 10, 281-287 (1998).
Rosenberg et al., *Nat. Med.*, 4, 321-327 (1998).
Sonderstrup et al., *Immunol. Rev*, 164, 129-138 (1998).
Southwood et al., *J. Immunol.*, 160, 3363-3373 (1998).
Stockert et al., *J. Exp. Med.*, 187, 1349-1354 (1998).
Thurner et al., *J. Exp. Med.*, 190, 1669-1678 (1999).
Toes et al., *J. Exp. Med.*, 189, 753-756 (1999).
Topalian et al., *J. Exp. Med.*, 183, 1965-1971 (1996).
Touloukian et al., *J. Immunol.*, 164, 3535-3542 (2000).
Van Der Bruggen et al., *Science*, 254, 1643-1647 (1991).
Walter et al., *N. Engl. J. Med.*, 333, 1038-1044 (1995).
Wang et al., *Gene*, 153, 197-202 (1995).
Wang et al., *J. Exp. Med.*, 181, 799-804 (1995).
Wang et al., *J. Exp. Med.*, 184, 2207-2216 (1996).
Wang, *Mol. Med.*, 3, 716-31 (1997).
Wang et al., *J. Immunol.*, 161, 3596-3606 (1998).
Wang et al., *Immunol. Rev.*, 170, 85-100 (1999).
Wang et al., *J. Exp. Med.*, 189, 1659-1667 (1999).
Wang et al., *Science*, 284, 1351-1354 (1999).
Wang et al., *Trends in Immunology*, 22(5), 269-276 (2001).
Weber et al., *J. Clin. Invest.*, 102, 1258-1264 (1998).
Williams et al., *Proc. Natl. Acad. Sci,*. USA, 88, 2726-2730 (1991).
Wolff et al., *Science*, 247, 1465-1468 (1990).
Yang et al., *Proc. Natl. Acad. Sci*, USA, 87, 9568-9572 (1990).
Zeng et al., *J. Immunol.*, 165, 1153-1159 (2000).
Zeng et al., *PNAS*, 98(7), 3964-3969 (2001).

* cited by examiner

FIG. 1A

SEQ ID NO:1  AGCAGGGGCGCTGTGTGTACCGAGAATACCTCGTGGCCCTGACCTT

CTCTCTGAGAGCCGGGCAGAGGCTCCGGAGCCATGCAGGCCGAAGGCCGGGGCACA
                                  ↑
                                SEQ ID NO:2

(SEQ ID NO:3) ORF1▶ M  Q  A  E  G  R  G  T

GGGGGTTCGACGGGGACGGCGATGCTGGACGGGGCCCTGATTCCTGATGGCCC

ORF1▶ G  G  S  T  G  D  A  D  G  P  G  G  P  G  I  P  D  G  P

AGGGGGCAATGCTGGCGGCCCAGAGGCTGCCCACGGGGCAGAGAGTCCCC

ORF1▶ G  G  N  A  G  G  P  G  E  A  G  A  T  G  G  R  G  P

GGGGCCAGGGCAGCAAGGCCTCGGGGCCGGAGGAGGCCCCGCGGGGTCCG

ORF1▶ R  G  A  G  A  A  R  A  S  G  P  G  G  G  A  P  R  G  P

CATGGCGGGGCCTTCAGGGCTGAATGCTGCAGATGCGGGGGCCAGGGGGCC

ORF1▶ H  G  G  A  A  S  G  L  N  G  C  C  R  C  G  A  R  G  P

FIG. 1B

```
        GGAGAGCCGGCCTGCTTGAGTTCTACCTGCCTTTCGGCACACCCATGGAAG
ORF1▲    E  S  R  L  L  E  F  Y  L  A  M  P  F  A  T  P  M  E
                                      →SEQ ID NO:27
        CAGAGCTGGCCCGCAGGAGCCTGGCCCAGGATGCCCCACCGCTTCCCGTGCCAGGG
ORF1▲ A  E  L  A  R  R  S  L  A  Q  D  A  P  P  L  P  V  P  G
        GTGCTTCTGAAGGAGTTCACTGTCCGGCAACATACTGACTATCCGACTCACTGC
ORF1▲ V  L  L  K  E  F  T  V  S  G  N  I  L  T  I  R  L  T  A
        TGCAGACCACCGGCCAACTGCAGCTCTCCATCAGCTCCTGTCTCCAGCAGCTTTCCC
ORF1▲    A  D  H  R  Q  L  Q  L  S  I  S  S  C  L  Q  Q  L  S
        TGTTGATGTGGATCACGCAGTGCTTTCTGCCCGTGTTTTTGGCTCAGCCTCCCTCA
ORF1▲ L  L  M  W  I  T  Q  C  F  L  P  V  F  L  A  Q  P  P  S
                    ↑
        GGGCAGAGGGCGCTAAGCCCCAGCCCTGGCCCCCCTTCCTAGGTCATGCCTCCTCCCCT
ORF1▲ G  Q  R  R
        AGGGAATGGTCCCAGCACGAGTGGCCAGTTCATTGTGGGGCCTGATTGTTGTCG
        CTGGGAGGAGGACGGCTTACATGTTTGTTTCTGTAGAAAATAAAAACTGAGCTACGAA
        AAAAAAAAAAAAAAAAAAAA
```

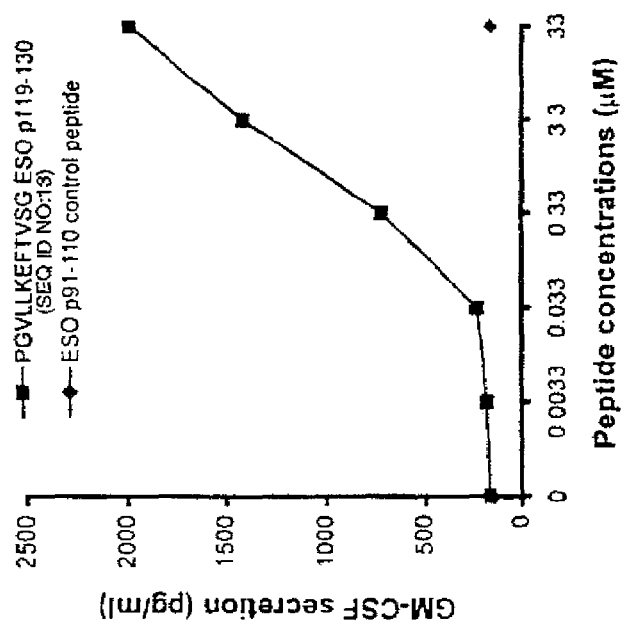
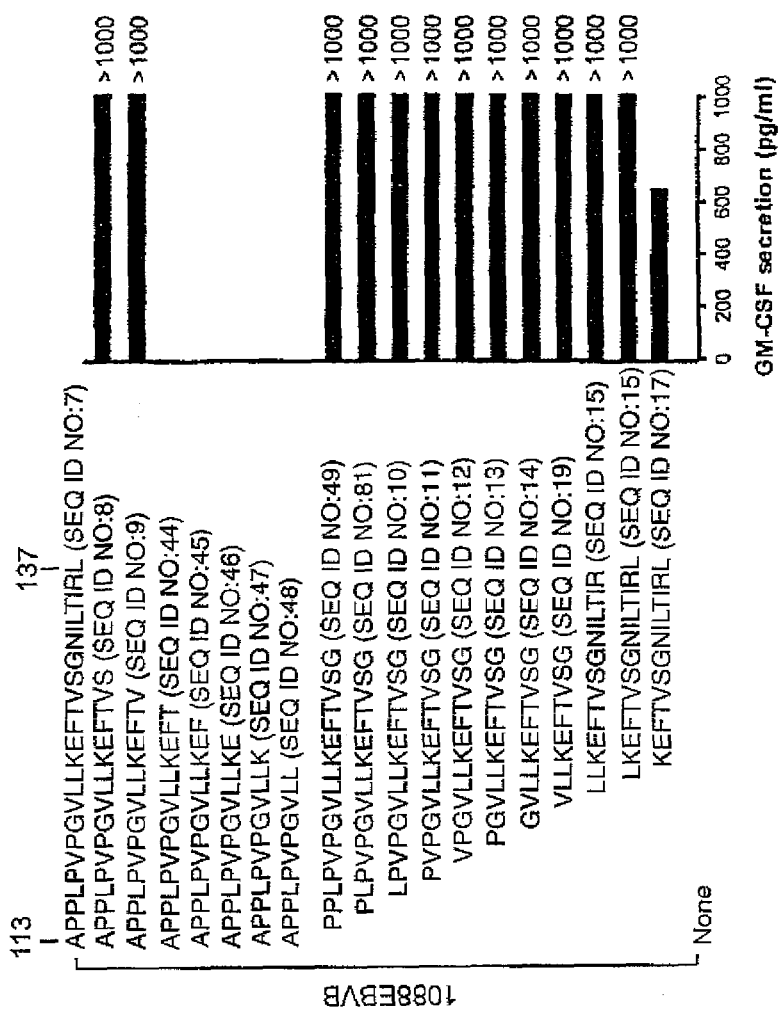
FIGURE 6A
FIGURE 6B

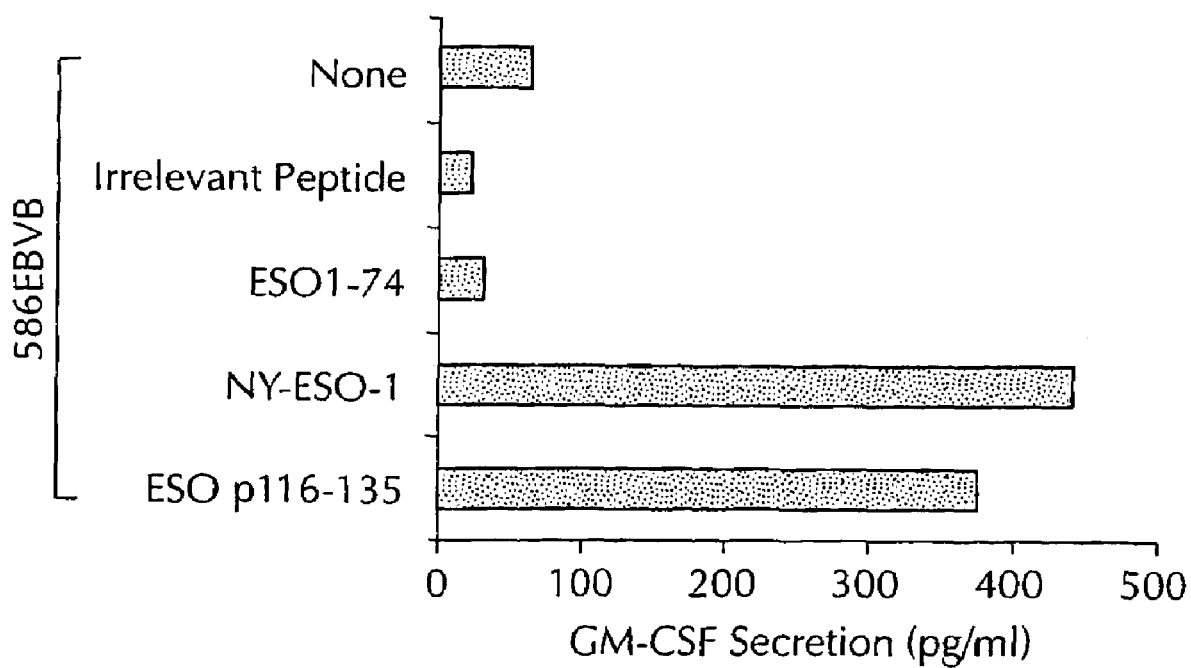

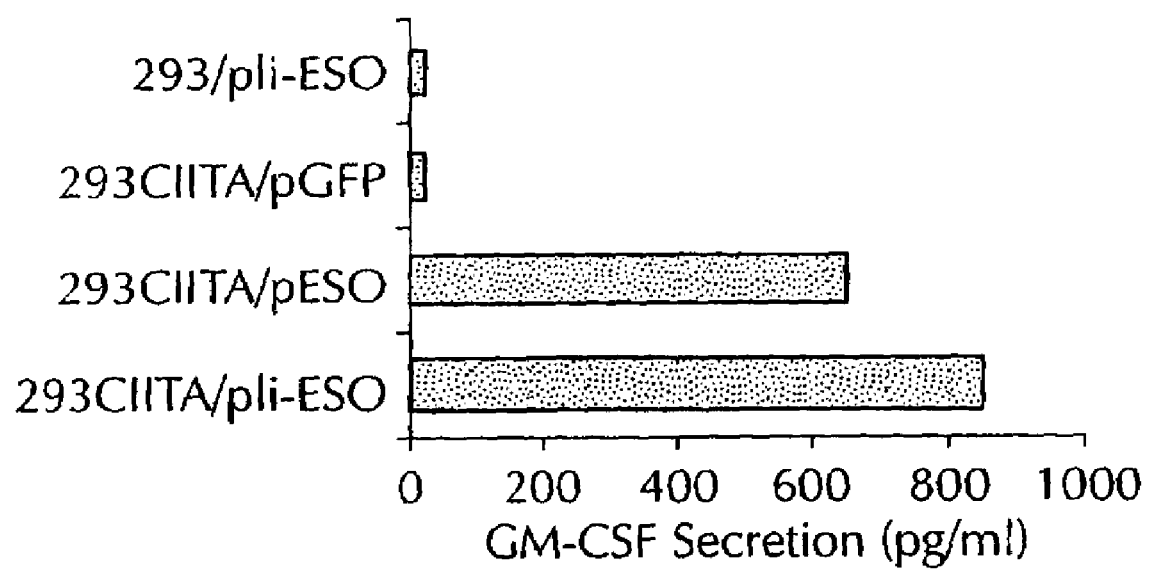

FIGURE 11A

121 ... 177
SCLQQLSLLMWITQCFLPVFLAQPPSG (SEQ ID NO:53)

1088 EBVB:
- none
- SLLMWITQCFLPVF (SEQ ID NO:54)
- LLMWITQCFLPVFL (SEQ ID NO:55)
- LMWITQCFLPVFLA (SEQ ID NO:56)
- MWITQCFLPVFLAQ (SEQ ID NO:57)
- WITQCFLPVFLAQP (SEQ ID NO:58)
- ITQCFLPVFLAQPP (SEQ ID NO:59)
- TQCFLPVFLAQPPS (SEQ ID NO:82)
- QCFLPVFLAQPPSG (SEQ ID NO:83)
- QQLSLLMWITQCFL (SEQ ID NO:84)
- LQQLSLLMWITQCF (SEQ ID NO:85)
- CLQQLSLLMWITQC (SEQ ID NO:86)
- SCLQQLSLLMWITQ (SEQ ID NO:87)
- SCLQQLSLLMWIT (SEQ ID NO:88)

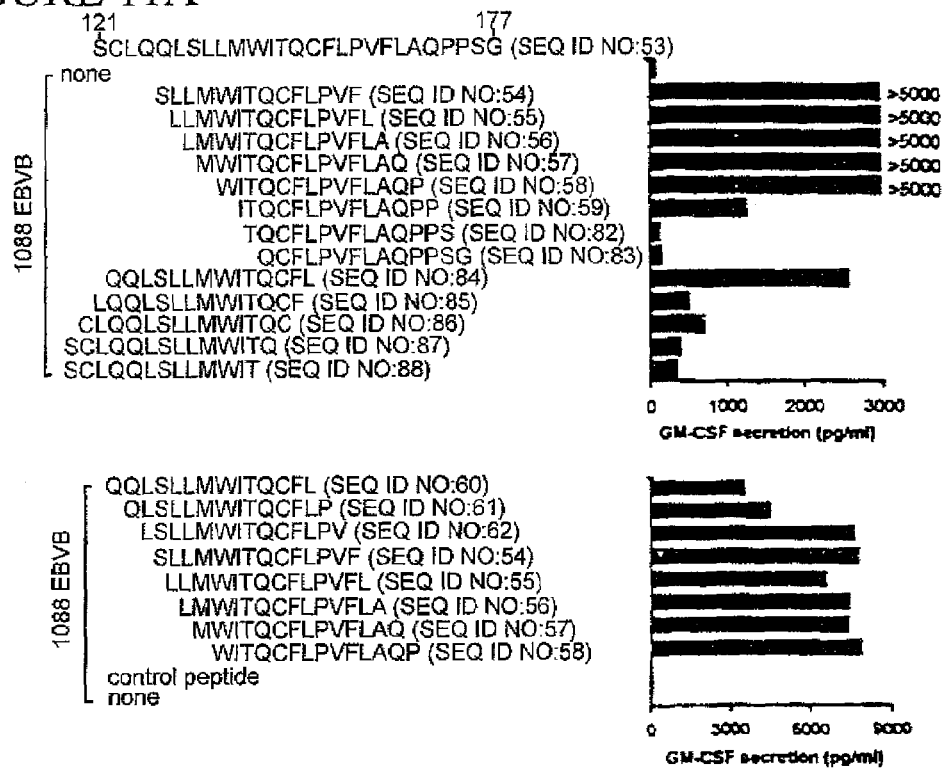

1088 EBVB:
- QQLSLLMWITQCFL (SEQ ID NO:60)
- QLSLLMWITQCFLP (SEQ ID NO:61)
- LSLLMWITQCFLPV (SEQ ID NO:62)
- SLLMWITQCFLPVF (SEQ ID NO:54)
- LLMWITQCFLPVFL (SEQ ID NO:55)
- LMWITQCFLPVFLA (SEQ ID NO:56)
- MWITQCFLPVFLAQ (SEQ ID NO:57)
- WITQCFLPVFLAQP (SEQ ID NO:58)
- control peptide
- none

FIGURE 11B

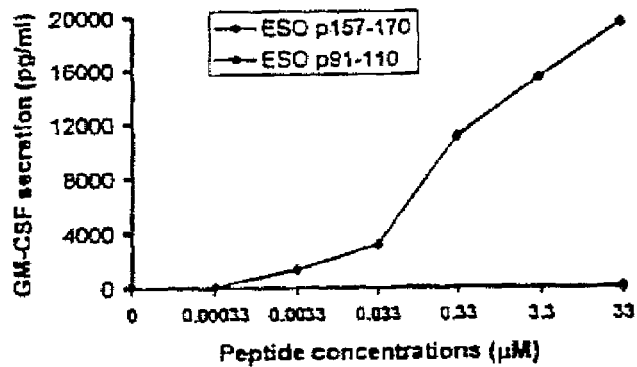

FIGURE 11C

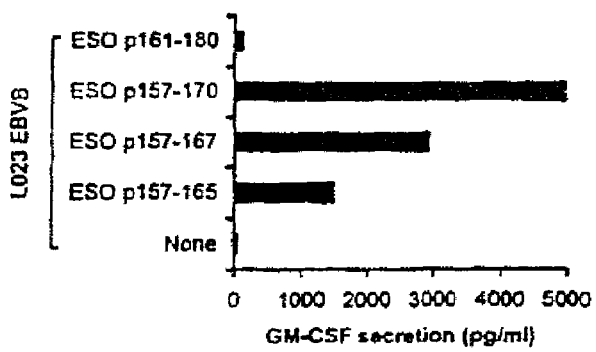

MHC CLASS II RESTRICTED T CELL EPITOPES FROM THE CANCER ANTIGEN, NY ESO-1

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 28,000 Byte ASCII (Text) file named "217955.2_ST25.TXT," created on Jan. 3, 2008.

FIELD OF THE INVENTION

The present invention relates to the area of cancer diagnostics and therapeutics including a cancer vaccine. More specifically, the invention relates to the isolation and purification of a novel human MHC class II restricted T cell epitope derived from the cancer peptide, NY ESO-1 and analogs thereof and DNA sequence encoding the MHC class II restricted T cell epitope or portion thereof. In particular, the invention relates to HLA-DR and HLA-DP restricted T cell epitopes from NY ESO-1. The invention further relates to methods of detecting, diagnosing and treating cancer and precancer in an individual.

BACKGROUND OF THE INVENTION

T cells play an important role in controlling tumor growth and mediating tumor regression. To understand the molecular basis of T cell-mediated antitumor immunity, a number of tumor antigens recognized by CD8[+] T cells have been identified in melanoma as well as in other types of cancers (1-3). These studies have led to several clinical trials using peptides derived from the molecularly defined tumor antigens (4-7). Although the clinical trial using a modified peptide derived from gp100 provided some evidence of therapeutic efficacy for the treatment of patients with metastatic melanoma (4), these studies mainly focused on the use of CD8[+] T cells. Increasing evidence from both human and animal studies has indicated that optimal cancer vaccines require the participation of both CD4[+] and CD8[+] T cells (8, 9). Moreover, tumor-specific CD4[+] T cells are required for generating protective immunity against MHC class II-negative tumor cells (10, 11). Identification of such antigens is thus important for the development of cancer vaccines as well as for our understanding of the mechanism by which CD4[+] T cells regulate host immune responses.

Thus far, only a limited number of MHC class II-restricted tumor antigens have been identified. Several known MHC class I-restricted tumor antigens such as tyrosinase, gp100 and MAGE-3 were demonstrated to contain MHC class II-restricted epitopes recognized by CD4[+] T cells (12-15). Recently, a genetic approach was developed to identify unknown MHC class II-restricted tumor antigens by using tumor-specific CD4+ T cells (16). This has led to the identification of several mutated tumor antigens including CDC27, TPI and LDFP (16, 17). Among them, TPI is a mutated antigen that was independently identified by a biochemical approach (18).

The NY-ESO-1 gene was previously identified by antibody screening (19), and was recently identified as an MHC class I-restricted tumor antigen as well (20, 21). High titers of antibodies against NY-ESO-1 were also detected from patients with cancer (22). The NY-ESO-1 cDNA encoded two gene products from two overlapping open reading frames (20). Because of its strict tumor-specific expression pattern with the exception of expression in normal testis as well as its high frequency of expression in many tumors including melanoma, breast, prostate, lung and other cancers (18, 20, 23), NY-ESO-1 is potentially an important immune target for the development of immunotherapies for a variety of cancer types (24).

Although both CTL and antibody immune responses against NY-ESO-1 were demonstrated in patients with cancer, no MHC class II-restricted T cell epitopes in the NY-ESO-1 protein have been reported.

The present invention is the identification and isolation of novel MHC class II restricted T cell epitopes from NY-ESO-1 which are recognized by CD4[+] T cells. The cancer epitopes of the invention are useful as an immunogen and vaccine to inhibit or prevent cancer in a mammal and as a diagnostic agent to detect cancer or precancer.

SUMMARY OF THE INVENTION

One object of the present invention is to provide a novel peptide and portions thereof recognized as a MHC class II restricted T cell epitope by CD4[+] T lymphocytes. The antigenic cancer peptides of the present invention are encoded within or by a portion of the NY ESO-1 (term used interchangeably herein with CAG-3) gene (SEQ ID NO:1) (Genbank Accession No. AF038567; 8:9), or variants or homologs thereof such as LAGE gene (Genbank Accession No. AJ223040, AJ223041, and AJ223093).

One aspect of the invention are MHC class II restricted T cell epitopes encoded by the NY-ESO-1 gene, or variants thereof, which are useful as a cancer vaccine capable of eliciting CD4[+] T lymphocytes which results in protection of the recipient from development of cancer and protection from metastasis. The present invention also relates to a method of administering the cancer vaccine in an effective amount to inhibit or prevent cancers or inhibit the growth of cells expressing the NY-ESO-1 gene product.

One aspect of the invention are HLA-DR and HLA-DP restricted T cell epitopes encoded by the NY-ESO-1 gene, or variants and homologs thereof, which are useful as an immunogen and as a cancer vaccine capable of eliciting CD4[+] T lymphocytes and an anti-NY-ESO-1 antibody response and in turn offering protection and/or therapeutic benefits to the recipient from development of cancer and protection from metastasis. The present invention also relates to a method of administering the cancer vaccine in an effective amount to inhibit or prevent cancers, inhibit the growth of cells expressing the NY-ESO-1 gene product and inhibit metastasis.

Another aspect of the present invention is a pharmaceutical composition comprising an MHC class II restricted T cell epitope derived from NY-ESO-1 or variant thereof alone or in combination with one or more immunostimulatory molecules. The pharmaceutical composition comprising at least one NY-ESO-1 MHC class II restricted T cell epitope, or combination of epitopes which stimulate NY-ESO-1 antigen specific CD4[+] T-cells to elicit an immunogenic response against tumors and cancers. The pharmaceutical composition may additionally comprise one or more MHC class I restricted T cell epitopes derived from NY-ESO-1 for generation of CD8[+] T lymphocytes. The NY-ESO-1 MHC class II restricted T cell epitope and the NY-ESO-1 MHC class I restricted T cell epitope may each be provided as a discrete epitope or linked together and may be provided in the form of multimers. The cancer epitope or variant thereof may be provided as an immunogen or as a vaccine for prevention or treatment of cancer. The pharmaceutical composition is useful in methods of treating or preventing cancer in a mammal. In the method of treatment, the pharmaceutical composition is administered to the mammal in an amount effective in preventing or inhibiting the cancer in the mammal.

Another aspect of the present invention is a pharmaceutical composition comprising an HLA-DR restricted and/or an HLA-DP restricted T cell epitope derived from NY-ESO-1 or variant thereof alone or in combination with one or more immunostimulatory molecules. The pharmaceutical composition comprising at least one NY-ESO-1 HLA-DR restricted T cell epitope or at least one NY-ESO-1 HLA-DP restricted T cell epitope, or combination of MHC class II restricted T cell epitopes which stimulate NY-ESO-1 antigen specific CD4+ T-cells to elicit an immunogenic response against tumors and cancers. The pharmaceutical composition may additionally comprise one or more MHC class I restricted T cell epitopes derived from NY-ESO-1 for generation of CD8+ T lymphocytes. The NY-ESO-1 HLA-DR restricted T cell epitope or NY-ESO-1 HLA-DP restricted T cell epitope and the NY-ESO-1 MHC class I restricted T cell epitope may each be provided as a discrete epitope or linked together. The cancer epitope or variant thereof may be provided as an immunogen or as a vaccine for prevention or treatment of cancer. The pharmaceutical composition is useful in methods of treating or preventing cancer in a mammal. In a method of treatment, the pharmaceutical composition is administered to the mammal in an amount effective in eliciting CD4+ T cell and/or anti-NY-ESO-1 antibody response for preventing or inhibiting cancer in the mammal.

Another object of the present invention is a method of generating MHC class II restricted T cell epitopes of NY-ESO-1 or variants thereof by translation of DNA sequence encoding same from a NY-ESO-1 gene, portion or homolog thereof.

Another object of the present invention is a method of generating HLA-DR restricted T cell epitopes or HLA-DP restricted T cell epitopes of NY-ESO-1 or variants or derivatives thereof by translation of DNA sequence encoding same from a NY-ESO-1 gene or portion or homolog thereof.

A further aspect of the invention is the isolated DNA or RNA sequence that encodes at least one MHC class II restricted T cell epitope of NY-ESO-1 or variant thereof, and complementary sequence thereof and the use of the DNA or RNA sequence as vaccines and in methods of producing the MHC class II restricted T cell epitopes of NY-ESO-1 or variants thereof. The invention further provides oligonucleotides of the DNA or RNA sequence for use as probes, primers or antisense.

A further aspect of the invention is the isolated DNA or RNA sequence that encodes HLA-DR restricted T cell epitopes, HLA-DP restricted T cell epitopes of NY-ESO-1 or variant and combinations thereof and the use of the DNA or RNA sequence in methods of producing the HLA-DR restricted T cell epitopes, the HLA-DP restricted T cell epitopes of NY-ESO-1 or variants and combinations thereof. The invention further provides oligonucleotides of the DNA or RNA sequence for use as probes, primers or antisense.

The present invention further provides vectors comprising nucleic acid sequences encoding at least one MHC class II restricted cell epitope of NY-ESO-1 or variant thereof alone or in combination with a second DNA sequence encoding at least one immunostimulatory molecule.

The present invention further provides vectors comprising nucleic acid sequences encoding at least one HLA-DR restricted T cell epitope or at least one HLA-DP restricted T cell epitope of NY-ESO-1 or variant or combination thereof alone or in combination with a second DNA sequence encoding at least one immunostimulatory molecule.

The invention also provides host cells transfected or transduced with a vector comprising DNA sequence encoding at least one MHC class II restricted T cell epitope of NY-ESO-1 or variant thereof alone or in combination with a second DNA sequence encoding at least one immunostimulatory molecule. The vectors and host cells may serve as vaccines in which expression of the MHC class II restricted T cell epitope results in the stimulation of tumor antigen specific CD4+ T lymphocytes in a mammal immunized with the vaccine.

The invention also provides host cells transfected or transduced with a vector comprising DNA sequence encoding at least one HLA-DR restricted T cell epitope or at least one HLA-DP restricted T cell epitope of NY-ESO-1 or variant or combination thereof alone or in combination with a second DNA sequence encoding at least one immunostimulatory molecule. The vectors and host cells may serve as vaccines in which expression of the HLA-DR restricted T cell epitope and/or the HLA-DP restricted T cell epitope results in the stimulation of tumor antigen specific CD4+ T lymphocytes in a mammal immunized with the vaccine.

The invention provides a method of diagnosis of cancer or precancer in a mammal by detection of a MHC class II restricted T cell epitope of NY-ESO-1 or variant thereof.

The invention provides a method of diagnosis of cancer or precancer in a mammal by detection of an HLA-DR restricted T cell epitope and/or an HLA-DP restricted T cell epitope of NY-ESO-1 or variant thereof.

It is yet another object of the invention to provide a method for diagnosing human preneoplastic and neoplastic cells and tissues. In accordance with the invention, the method comprises isolating cells, tissues or extracts thereof from a human and detecting the DNA sequence, RNA sequence or portion thereof encoding a MHC class II restricted T cell epitope of NY-ESO-1 or variant thereof or detecting the epitope or variant thereof expressed by the DNA sequence or RNA sequence, wherein detection odor increase in the DNA sequence, RNA sequence or expression product is indicative of preneoplasia and neoplasia.

It is still another object of the invention to provide a method for diagnosing human preneoplastic and neoplastic cells and tissues. In accordance with the invention, the method comprises isolating cells, tissues or extracts thereof from a human and detecting the DNA sequence, RNA sequence or portion thereof encoding an HLA-DR restricted T cell epitope or HLA-DP restricted T cell epitope of NY-ESO-1 or variant thereof or detecting the epitope or variant or combination thereof expressed by the DNA sequence or RNA sequence, wherein detection of/or increase in the DNA sequence, RNA sequence or expression product is indicative of preneoplasia and neoplasia.

Another object of the invention is to provide a transgenic animal which has incorporated into its genome one or more copies of the DNA sequence encoding at least one MHC class II restricted T cell epitope of NY-ESO-1 or variant thereof. The incorporation of the DNA sequence results in expression or overexpression of the epitope. Such transgenic animals are useful for screening of therapeutic agents useful in treating cancer.

Still another object of the invention is to provide a transgenic animal which has incorporated into its genome one or more copies of the DNA sequence encoding at least one HLA-DR restricted T cell epitope, or at least one HLA-DP restricted T cell epitope of NY-ESO-1 or variant or combination thereof. The incorporation of the DNA sequence results in expression or overexpression of the epitope. Such transgenic animals are useful for screening of therapeutic agents useful in treating cancer.

Still another aspect of the invention are monoclonal, polyclonal and recombinant antibodies reactive with the MHC class II restricted T cell epitope of NY-ESO-1 or variant thereof, for use as a therapeutic and in diagnostic and detection assays. The monoclonal and polyclonal antibodies may be provided in the form of a kit alone, or along with other reagents commonly used in diagnostic and detection assays.

Yet another aspect of the invention are monoclonal, polyclonal and recombinant antibodies reactive with the HLA-DR restricted T cell epitope or HLA-DP restricted T cell epitope of NY-ESO-1, or reactive with the HLA-DP epitope in combination with the HLA-DP molecule or react with the HLA-DR epitope in combination with the HLA-DR molecule, or variant thereof, for use as a therapeutic and in diagnostic and detection assays. The monoclonal and polyclonal antibodies may be provided in the form of a kit alone, or along with other reagents commonly used in diagnostic and detection assays.

BRIEF DESCRIPTION OF THE FIGURES

These and other objects, features, and many of the attendant advantages of the invention will be better understood upon a reading of the following detailed description when considered in connection with the accompanying drawings wherein:

FIGS. 1A and 1B. Nucleotide and amino acid sequence of NY-ESO-1. Numbering of nucleotide sequence of NY-ESO-1 starts from the first nucleotide in the 5' untranslated region.

FIG. 4A-4E. Characterization of the TE4-1 CD4$^+$ T cell line. (4A) TE4-1 specifically recognized 1088 EBV B cells (HLA-DR$^+$) pulsed with ESO p 116-135 peptide or purified NY-ESO-1 protein, but not ESO1-74 protein which lacked the putative epitope. (4B) HLA DR-restriction was required for the recognition of NY-ESO-1 by TE4-1. Two overlapping peptides ESO p 111-130 and p 116-135 were recognized when pulsed onto 2931MDR cells. 1×10$^5$ target cells were co-cultured with 4×10$^4$ TE4-1 cells overnight before GM-CSF secretion was measured. (4C) Recognition of 293MDR pulsed with ESO p116-135 peptide was specifically inhibited by the anti-HLA-DR antibody (HB55), but not by the anti-class I antibody (HB95). The amount of GM-CSF secreted by TE4-1 in the absence of antibodies was used as the reference, against which the percent GM-CSF release in the presence of antibodies was calculated. Inhibition by the control (mouse IgG2a) and the anti-MHC-class I antibodies (HB95) had little effect. CTL C3G1 (courtesy of C. Macalli) was a gp100 specific CD8$^+$ T cell line that recognized 624.38mel, and was used as a control for the activity of HB95 (FIG. 4D). T3-80 was a CD4$^+$ T cell line that recognized 1362mel and was used as the control for the activity of HB55 (FIG. 4E).

FIG. 6A-6B. Charaction of the NY-ESO-1 peptide epitope recognized by TE4-1. (6A) Determination of the anchor positions for the HLA DR-restricted NY-ESO-1 epitope. 1088 EBV B cells were pulsed with 20 M of the indicated peptides. TE4-1 cells were cocultured with the target cells for overnight before GM-CSF was measured. (6B) Peptide titration experiment using ESO p119-130. ESO p119-130 was chosen based on its recognition shown in FIG. 6(A). ESO p119-130 diluted at the indicated concentrations were pulsed onto 1088 EBV B cells, which were used as targets for recognition by TE4-1. Recognition of a control peptide, ESO p91-110 was measured only at the highest concentration of 33 M.

FIGS. 7A and 7B. 7A. Recognition of NY-ESO-1 protein and ESO p116-135 by TE4-1 using DR1+EBVB as APC. NY-ESO-1 protein (5 μg/ml) and peptides (33 μM) were pulsed onto 586EBV B(DR1+) cells and washed twice. TE4-1 T cells were then added and cocultured overnight before GM-CSF was assayed. FIG. 7B. 586EBV B pulsed with ESOp116-135 (33 μM) was used to stimulate TE4-1 with and without the blocking antibodies. IID95 (anti-class I antibody), IIB55 (anti-DR antibody), and isotype control antibodies were used.

(FIG. 8A) Specific peptide reactivity was detected in multiple wells after three in vitro stimulations. A total of 24 wells each containing 2.5×10$^5$ PBMC in a 96-well plate were stimulated weekly for three weeks. Fifteen of 24 wells showed marked growth and tested for specific activity. T cells from each well were incubated with 1088 EBVB cells and 1088 EBVB cells pulsed with the ESO p161-180 peptide, respectively. GM-CSF release was measured from supernatants. (FIG. 8B). TE4-2 T cells specifically reacted with NY-ESO-1 peptides and protein. Overlapping peptides ESO p161-180 and ESO p156-175 were pulsed onto 1088 (DR4+) and 586 EBVB (DR1$^+$) cells at 20 micro g/ml for 90 minutes. ESO p91-110 was used as an irrelevant peptide for pulsing. Purified NY-ESO-1 and ESO1-75 proteins were pulsed overnight at 5 micro g/ml and 2 micro g/ml respectively to maintain the same molar ratio. After three washes, TE4-2 T cells were added and incubated overnight. GM-CSF release was measured. (FIG. 8C). A panel of EBVB cells pulsed with ESO p161-180 were used as targets for TE4-2 CD4+ T cells. These EBVB lines were known to express different HLA DR and DQ alleles. Their HLA DP alleles were molecularly typed in this study (Table 2).

(FIG. 9A) CK3H6 T cells specifically recognized gp100 p209-218 peptide in the context of HLA A2 and was used as the specificity control for anti-MHC class I antibody (FIG. 9B). 1088 EBB (A2+) pulsed with gp100 p209-218 peptide was used as targets. A CD4+ T cell line (T3-80) recognized 1362mel in an HLA-DR restricted fashion and was used as the specificity control for anti-MHC class II and anti-DR antibodies (FIG. 9C).

(FIG. 10A). TE4-2 recognized melanoma lines expressing both NY-ESO-1 and DP4. Melanoma lines with known NY-ESO-1 expression (by RT-PCR) and HLA DP types (determined by RT-PCR and sequencing) were used as targets. An overnight IFN-gamma treatment (500 units/ml) was conducted for F026mel, 526mel, and 397mel to up-regulate their MHC class II expression in this experiment. TE4-2 T cells were co-cultured with tumor cells overnight before cytokine release was measured. (FIG. 10B). TE4-2 CD4+ T cell line recognized 293CIITA transfected with NY-ESO-1 with or without the invariant chain (Ii) targeting sequence. Parental 293 cells and 293CIITA cells were transfected with plasmid encoding NY-ESO-1 (pESO), Ii-NY-ESO-1 (pIi-ESO), or GFP pGFP), respectively. TE4-2 T cells were co-cultured with the transfectants overnight before cytokine release was assayed.

FIG. 11A-11C. Characterization of T cell epitopes recognized by TE4-2. (FIG. 11A). Determination of the anchor residues and minimal length of the NY-ESO-1 epitope for T cell recognition. Synthetic peptides with amino acid deletions at the N- or C-terminus were used to pulse 1088 EBVB cells at 40 micro g/ml. EBVB cells were then thoroughly washed and used as target cells to stimulate TE4-2 T cells. Two separate experiments were conducted and presented as the top and bottom panel in this figure. (FIG. 11B). Determination of the minimal peptide concentration required for T cell recognition. The ESO p157-170 peptide was used to pulse 1088 EBVB cells at various concentrations. The peptide pulsed cells were then washed and used as targets to stimulate TE4-2 line. A control peptide ESO p91-110 was used only at the highest concentration, 33 micromoles. (FIG. 11C). Recognition of the DPB1*0401-restricted CD4+ T cell epitope by the NY-ESO-1 specific CD8+ T cells. TE8-1 cell line was generated from PBMC of patient TE by in vitro stimulation with the ESO p157-167 peptide. L023 EBVB cells (BLA-A2+, DP4−) were pulsed with peptides covering the DPB1*0401 epitope region in a serum-free medium, washed, and used to stimulate TE8-1 T cells.

FIG. 12A. 586 EBVB cells (A2−, DP4+) were used as antigen-presenting cells to pulse with indicated peptides at various concentrations. Cells were washed and then incubated with TE4-2 CD4+ T cells before cytokine release was assayed. FIG. 12B. L023 EBVB cells (A2+, DP4−) were used as antigen-presenting cells to pulse with indicated peptides at various concentrations. Cells were washed and then incubated with TE4-2 CD4+ T cells before cytokine release was assayed.

DETAILED DESCRIPTION OF THE INVENTION

Figure 2A:
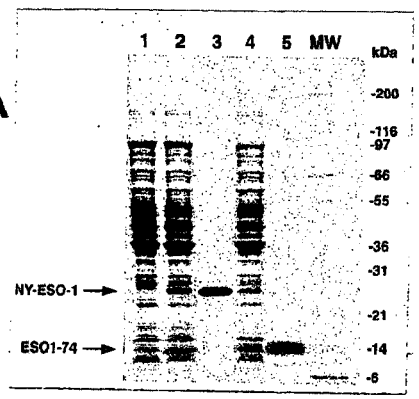
FIG. 2A-2C: 2(A) Purification of full-length NY-ESO-1 protein using a $Ni^{2+}$ chromatography column. SDS polyacrylamide gel showed the crude extract from E. coli st BL21 (DE3) bearing pET28 vector (lane 1), pNY-ESO-1 (lane 2), the purified NY-ESO-1 protein (lane 3), bacterial extract encoding the truncated NY-ESO-1 (lane 4), and the purified truncated NY-ESO-1 protein, ESO1-74 (lane 5). (2B) Western blot to confirm the specificity of antibodies against NY-ESO-1. Sera at 1 to 2000 dilution from two representative patients, one with (lanes 1, 2, and 3) and one without (lanes 4, 5, and 6) detectable NY-ESO-1 antibodies by ELISA were used against bacterial extract encoding the vector only (lanes 1 and 4), encoding NY-ESO-1 (lanes 2 and 5), and the purified NY-ESO-1 protein (lanes 3 and 6). (2C) Patient TE was among the melanoma patients who had antibodies against NY-ESO-1 protein. ELISA was performed using sera from 88 patients for the presence of antibodies against NY-ESO-1 (BSA as control protein). Values of O.D. 450 at 1:25, 1:250, and 1:2500 of sera dilutions were plotted. Sera from normal donors were used as controls, and their mean OD value was also plotted (ND).

The present invention encompasses cancer epitopes, portion, derivatives or variants thereof of NY-ESO-1 which are immunologically recognized by MHC class II restricted CD4+ T lymphocytes of the immune system. The cancer epitopes of the present invention specifically causes a humoral-mediated immune response by interaction with CD4+ T cells of the immune system. This interaction between the antigenic cancer epitope and the CD4+ T cells causes the CD4+ T cells to respond against, and recruit other cells in the immune system in the prevention, elimination or reduction of cancer in a mammal, including humans.

The NY-ESO-1 MHC class II restricted T cell epitopes of the present invention form part of, or are derived from, cancers including but not limited to primary or metastatic melanoma, thymoma, lymphoma, sarcoma, lung cancer, liver cancer, non-Hodgkin's lymphoma, Hodgkin's lymphoma, leukemias, uterine cancer, cervical cancer, bladder cancer, kidney cancer, head and neck cancer, neuroblastoma and adenocarcinomas such as breast cancer, prostate cancer, ovarian cancer, pancreatic cancer, thyroid cancer and the like.

The term melanoma includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome.

Of particular interest are cancer epitopes or derivatives thereof recognized by autologous CD4+ T lymphocytes in patients with cancer, in particular melanoma. Of further interest are cancer epitopes or derivatives thereof recognized by MHC (or HLA) class II restricted CD4+ T lymphocytes, in particular HLA-DR restricted T lymphocytes and/or HLA DP restricted T lymphocytes. In one embodiment, the NY-ESO cancer epitope is recognized by CD4+ T lymphocytes in context of HLA-DR molecule. In another embodiment, the NY-ESO cancer epitope is recognized by CD4+ T lymphocytes in context of an HLA-DP molecule.

The "cancer epitope" of the present invention encompasses a portion or variant portion of NY-ESO-1 protein that elicites MHC class II restricted T lymphocytes, such as HLA-DR restricted and HLA-DP restricted T lymphocytes. Such lymphocytes may specifically react with the full length NY-ESO-1 protein, the MHC class II restricted T cell epitope and with naturally processed antigen from tumor cells.

The MHC class II restricted T cell epitope of NY-ESO-1 of the present invention may vary in size from about 9 amino acids to about 30 amino acids, preferably about 10 to about 15 amino acids in length.

In a particular embodiment, the MHC class II restricted T cell epitope of NY-ESO-1 of the present invention is about 9 to 10 amino acids in length.

In one embodiment, the MHC class II restricted T cell epitope of NY-ESO-1 is a peptide of at least about 10 amino acids in length that comprises the amino acid sequence:

$Xaa_1$ KEFTVS$Xaa_2$ (SEQ ID NO: 4) and variants or derivatives thereof. The amino acid at $Xaa_1$ and $Xaa_2$ and the number of amino acids at these positions at the N-terminus and C-terminus may vary as long as the epitope retains its ability to bind to/and stimulate CD4⁺ T lymphocytes. The epitope may comprise about 10 to about 30 amino acids, preferably less than 20 amino acids, more preferably about 10 to about 15 amino acids.

In another embodiment of the present invention the MHC class II restricted T cell epitope of NY-ESO-1 may be represented by the formula:

Xaa$_1$ VLLKEFTVSGXaa$_2$ (SEQ ID NO: 5), wherein Xaa$_1$ is no amino acid or one to about 10 naturally occurring amino acids, preferably one to about 5 amino acids; and Xaa$_2$ is no amino acid or one to about seven amino acids in length.

In another embodiment of the present invention, the MHC class II restricted T cell epitope of NY-ESO-1 comprises the amino acid sequence:

QDAPPLPVPG VLLKEFTVSGNILTIRL (SEQ ID NO: 6), or fragments, or derivatives thereof.

Also encompassed in the ambit of the invention are cancer peptides or portions thereof that share partial sequence homology with SEQ. ID NO: 4, 5 or 6. By partial amino acid sequence homology is meant a peptide having at least 85% sequence homology with SEQ. ID NO: 4, 5 or 6 preferably at least 95% sequence homology or greater and has the biological function of stimulating NY-ESO-1 MHC class II restricted specific CD4⁺ T lymphocytes. Mammalian homologs are included in the ambit of the invention including but not limited to primate and murine homologs.

In one embodiment the MHC class II restricted T cell epitope of NY-ESO-1 comprises the amino acid sequence:

```
APPLPVPGVLLKEFTVSGNILTIRL;    (SEQ ID NO: 7)
APPLPVPGVLLKEFTVS;            (SEQ ID NO: 8)
APPLPVPGVLLKEFTV;             (SEQ ID NO: 9)
LPVPGVLLKEFTVSG;              (SEQ ID NO: 10)
PVPGVLLKEFTVSG;               (SEQ ID NO: 11)
VPGVLLKEFTVSG:                (SEQ ID NO: 12)
PGVLLKEFTVSG;                 (SEQ ID NO: 13)
GVLLKEFTVSG;                  (SEQ ID NO: 14)
LLKEFTVSGNILTIR               (SEQ ID NO: 15)
LKEFTVSGNILTIRL;              (SEQ ID NO: 16)
KEFTVSGNILTIRL;               (SEQ ID NO: 17)
LPVPGVLLKEFTVSGNILTI;         (SEQ ID NO: 18)
``` or variant or derivatives thereof.

In a preferred embodiment of the MHC class II restricted T cell epitope of NY-ESO-1 comprises the amino acid sequence:

```
VLLKEFTVSG,      (SEQ ID NO: 19)
|  | ||
1  4 67
``` and variants or derivatives thereof.

Epitopes having substitutions within the above sequence are encompassed by the present invention. A substitution of a naturally occurring amino acid may be at one or more anchor positions, provided the substituted amino acid(s) results in equivalent or enhanced binding compared to SEQ ID NO: 19. It is predicted that the anchor positions of SEQ ID NO: 19 are at position 1-Leu, position 4-Glu, position 6-Thr, and position 7-Val. In one embodiment alanine is substituted for leucine at position 1.

In another embodiment of the present invention the MHC class II restricted T cell epitope of NY-ESO-1 comprises the amino acid sequence:

```
DHRQLQLSIS SCLQQLSLLM,     (SEQ ID NO: 20)
``` portion, variants and derivatives thereof. In one embodiment, the portion of SEQ ID NO: comprises the amino acid sequence:

```
DHRQLQLSIS SCLQQLS;        (SEQ ID NO: 29)
DHRQLQLSIS SCLQ;           (SEQ ID NO: 30)
   QLQLSIS SCLQQL          (SEQ ID NO: 31)
``` or variants and derivatives thereof.

In another embodiment of the present invention the MHC class II restricted T cell epitope of NY-ESO-1 comprises the amino acid sequence:

```
WITQCFLPVF LAQPPSGQRR      (SEQ ID NO: 21)
``` portion, variants and derivatives thereof. In one embodiment, the portion of SEQ ID NO: 21 comprises the amino acid sequence:

```
QCFLPVF LAQPPSGQRR;        (SEQ ID NO: 32)
   LPVF LAQPPSGQRR;        (SEQ ID NO: 33)
   CFLPVF LAQPPSGQ;        (SEQ ID NO: 34)
``` or variants and derivatives thereof.

The NY-ESO-1 cancer epitopes and derivatives thereof are recognized by MHC class II restricted CD4⁺ T lymphocytes. The class II molecules recognized in combination with the NY-ESO-1 epitope includes but are not limited to at least one HLA-DR, such as HLA-DR1, HLA-DR3, HLA-DR4 and other class II molecules which function due to degeneracy of class II peptide binding. In one embodiment, an HLA subtype recognized by the cancer peptides is the HLA-DR4 subtype. In another embodiment, the NY-ESO-1 cancer epitope binds ELA-DR1 and HLA-DR4.

In another embodiment, the epitope is an HLA-DP restricted T cell epitope of NY-ESO-1, comprising the general amino acid motif of:

Xaa$_1$I TQ Xaa$_2$ FXaa$_3$P Xaa$_4$ (SEQ ID NO: 51), wherein Xaa$_1$ is at least one naturally occurring amino acid; preferably an amino acid selected from the group consisting of Trp, Phe, Tyr, Met, Ile, Val, Ala; and combinations thereof, Xaa$_2$ is at least one naturally occurring amino acid, preferably an amino acid selected from the group consisting of Cys, Ser, Val, Ala, Thr; and combinations thereof, Xaa$_3$ is at least one naturally occurring amino acid, preferably an amino acid selected from the group consisting of Leu, Phe, Tyr, Met, Ile, Val, Ala; and combinations thereof and Xaa$_4$ is at least one naturally occurring amino acid, preferably an amino acid selected from the group consisting of Val, Tyr, Ile, Ala, Leu, Pro and combinations thereof.

Also encompassed in the ambit of the invention are cancer peptides or portions thereof that share partial sequence homology with SEQ. ID NO: 51. By partial amino acid sequence homology is meant a peptide having at least 85% sequence homology with SEQ. ID NO: 51 preferably at least 95% sequence homology or greater and has the biological function of stimulating NY-ESO-1 MHC class II restricted specific CD4+ T lymphocytes, preferably HLA-DP restricted T lymphocytes. Mammalian homologs are included in the ambit of the invention including but not limited to primate and murine homologs. Homologs also include peptides having sequence homology with SEQ ID NO: 51 which may be encoded by a gene other than the NY-ESO-1 gene, such as the LAGE gene.

Epitopes having substitutions within the above sequence are encompassed by the present invention. A substitution of a naturally occurring amino acid may be at one or more anchor positions, provided the substituted amino acid(s) results in equivalent or enhanced binding compared to SEQ ID NO: 51. It is predicted that the anchor positions of SEQ ID NO: 51 are at position 1, 7, and 9, i.e., the W, L, and V residues, respectively. Substitutions of these anchor residues can be but not limited to F, Y, M, I, V, and A for the "W" residue; F, Y, M, V, I, and A for the "L" residue; and Y, I, A, L, and P for the "V" residue. Another subsitution may involve the C residue as position 5 of SEQ ID NO: 1, which can be but not limited to residues S, V, A, and T.

In one embodiment, the MEC class II restricted T cell epitope of NY-ESO-1 is a peptide of at least about 10 amino acids in length that comprises the amino acid sequence:

Xaa$_1$ WITQCFLPVFXaa$_2$ (SEQ ID NO: 52) and variants or derivatives thereof. Xaa$_1$ and Xaa$_2$ may be no amino acid or one or more of the same or a variety of naturally occurring amino acids. The number of amino acids at these positions at the N-terminus and C-terminus may vary as long as the epitope retains its ability to bind to/and stimulate CD4+ T lymphocytes, in particular HLA-DP restricted CD4+ T lymphocytes. The epitope may comprise about 10 to about 30 amino acids, preferably less than 20 amino acids, more preferably about 10 to about 15 amino acids.

In one embodiment, the HLA-DP restricted T cell epitope of NY-ESO-1 comprises the amino acid sequence:

151-SCLQQLSLLMWITQCFLPVFLAQPPSG-177; (SEQ. ID NO. 53)

SLLMWITQCFLPVF; (SEQ. ID NO. 54)

LLMWITQCFLPVFL; (SEQ. ID NO. 55)

LMWITWCFLPVFLA; (SEQ. ID NO. 56)

MWITQCFLPVFLAQ; (SEQ. ID NO. 57)

WITQCFLPVFLAQP; (SEQ. ID NO. 58)

ITQCFLPVFLAQPP; (SEQ. ID NO. 59)

QQLSLLMWITQCFL; (SEQ. ID NO. 60)

QLSLLMWITQCFLP; (SEQ. ID NO. 61)

LSLLMWITQCFLPV; (SEQ. ID NO. 62)

and derivatives thereof.

The NY-ESO-1 cancer epitopes and derivatives thereof are recognized by HLA-DP restricted CD4+ T lymphocytes, and derivatives thereof, preferably HLA-DP4 restricted CD4+ T lymphocytes. The class II molecules recognized in combination with the NY-ESO-1 epitope includes HLA-DP and class II molecules which function due to degeneracy of class II peptide binding. A preferred HLA subtype recognized by the cancer peptides is the HLA-DPB1*0401-0402 allele and other alleles that may bind to the peptides due to function degeneracy.

Another embodiment of the present invention encompasses derivatives and variants of the MHC class II restricted T cell epitopes of NY-ESO-1 having sufficient homology to the epitopes thereof to effectively act to elicite MHC class II restricted CD4+ T lymphocytes. Such peptides may have conservative amino acid changes at one or more positions, in particular in the anchor positions. By conservative amino acid changes is meant, an amino acid change at a particular position which is of the same type as originally present; i.e. a hydrophobic amino acid exchanged for a hydrophobic amino acid, a basic amino acid for a basic amino acid, etc. Such amino acid changes do not significantly alter the overall charge and configuration of the peptide and therefore such variants maintain or enhance the anti-cancer activity of a cancer peptide. Examples of such conservative changes are well-known to the skilled artisan and are within the scope of the present invention.

The present invention also relates to functionally equivalent variants of the NY-ESO-1 MHC class II restricted T cell epitopes. "Functionally equivalent variants" includes peptides with partial sequence homology, peptides having one or more specific conservative and/or non-conservative amino acid changes, peptide conjugates, chimeric proteins, fusion proteins and peptides.

Another aspect of the invention are NY-ESO-1 peptides that function as epitopes for both HLA-DP restricted T cells and HLA class I restricted CD8+ T lymphocytes, in particular for HLA-A restricted T lymphocytes, preferably HLA-A2 restricted T lymphocytes. In one embodiment, the HLA-DP restricted and HLA class I restricted epitope of NY-ESO-1 comprise the amino acid sequence: SLLMWITQCFLPVF (SEQ ID NO: 54), as well as variants and homologs thereof. Variants include but are not limited to peptides having one or more substitutions in SLLMWITQCFLPVF (SEQ ID NO: 54) including but not limited to ESOp156R-169 comprising: RSLLMWITQCFLPV (SEQ ID NO: 63) and ESOp157-170R comprismig: SLLMWITQCFLPVR (SEQ ID NO: 64). Such substitutions render the peptide more soluble in aqueous solution while retaining the immunologic functional activity of the native sequences. The highly water soluble peptides may be easily purified to more than 90% purity.

The NY-ESO-1 MHC class II restricted T cell epitopes may be purified and isolated from natural sources such as from primary clinical isolates, cell lines and the like. The NY-ESO-1 MHC class II restricted T cell epitopes thereof are at least 90% pure, preferably at least 95% pure and as pure as 100%. The epitopes may also be obtained by chemical synthesis or by recombinant DNA techniques known in the arts. Techniques for chemical synthesis are described in J. M. Steward and J. D. Young, "Solid Phase Peptide Synthesis", W.H. Freeman & Co., San Francisco, 1969; M. Bodansky et al "Peptide Synthesis", John Wiley & Sons, Second Edition, 1976, and J. Meienhofer, "Hormonal Proteins and Peptides", Vol. 2, p. 46, Academic Press, New York, 1983 and E. Schroder and K. Kubke, "The Peptides", Vol. 1, Academic Press, New York, 1965.

The NY-ESO-1 class II restricted T cell epitopes may be formulated with pharmaceutically acceptable carriers into pharmaceutical compositions by methods known in the art. The composition is useful as an immunogen to elicit NY-ESO-1 specific CD4+ T lymphocytes and may be useful in eliciting anti-NY-ESO-1 antibody. The composition is also useful as a vaccine to prevent or treat cancer. The composition may fierier comprise at least one immunostimulatory molecule. Immunostimulatory molecules to be used in conjunction with the cancer epitope or portion thereof for stimulating MHC class II specific T cell responses include but are not limited to one or more major histocompatibility complex (MHC) class II molecules or cells expressing MHC class II molecules. The composition may father comprise other stimulator molecules including B7.1, B7.2, ICAM-1, ICAM-2, LFA-1, LFA-3, CD72 and the like, and cytokines which include but are not limited to IL-1 through IL-15, TNF$\alpha$, IFN$\gamma$, RANTES, G-CSF, M-CSF, IFN$\alpha$, CTAP III, ENA-78, GRO, I-309, PF4, EP-10, LD-78, MGSA, MIP-1$\alpha$, MIP-1$\beta$, or combination thereof, and the like for immunopotentiation.

The stimulatory molecule may be provided as a physically separate entity or it may be provided in the membrane of an antigen presenting cell such as B-cell, macrophage or dendritic cell, in the membrane of a liposome, or expressed on the surface of a transduced or transfected cell. DNA sequences of MHC class II immunostimulatory molecules are available from GenBank and the like. DNA sequences of HLA-DP immunostimulatory molecules are available from the GenBank/EMBL/DNA Data Bank of Japan (DDBJ) at GenBank, National Center for Biotechnology Information, 8600 Rockville Pike, Bethesda, Md. 20894 USA or from its web sites.

The pharmaceutical composition of the present invention may comprise several distinct MHC class II restricted T cell epitopes from NY-ESO-1 in addition to the NY-ESO-1 HLA-DR or HLA-DP restricted T cell cancer peptide thereof. These include but are not limited to the HLA-DR restricted epitopes and variants thereof, such as LPVPGVLLKEFTVSG (SEQ ID NO: 10), VLLKEFTVSGNILTIRLT (SEQ ID NO: 65), AADHRQLQLSISSCLQQL (SEQ ID NO: 66), and combinations thereof.

The pharmaceutical composition of the present invention may optionally comprise an MHC class I restricted NY-ESO-1 cancer peptide for eliciting MHC class I restricted cytotoxic T lymphocytes in addition to eliciting MHC class II restricted CD4$^+$ T lymphocytes. MHC class I restricted NY-ESO-1 cancer peptide include but are not limited to a cancer peptide represented by the formula:

Xaa$_1$ Xaa$_2$ Xaa$_3$ GP GGG AP Xaa$_1$ (SEQ ID NO: 22), wherein Xaa$_1$ is no amino acid or one to about 20 naturally occurring amino acids, preferably one to about S amino acids, Xaa$_2$ is Ala, Thr, Val, Leu or Arg, Xaa$_3$ is Ser or a conservative substitution such as Ala, Val, Ile, Leu, Thr and the like, Xaa$_4$ is Arg, Lys, preferably Arg, and fragments and derivatives thereof. In one embodiment, the MHC class I restricted NY-ESO-1 cancer peptide for use in the pharmaceutical composition comprises the amino acid sequence: ASGPGGGAPR (SEQ ID NO: 23).

The NY-ESO-1 MHC class II restricted T cell epitope and the NY-ESO-1 MHC class I restricted T cell epitope may each be provided as a discrete epitope or linked together as a single peptide. The epitopes may be linked together or chemically synthesized by methods known in the art. A chemical linker, a peptide linker, a peptide bond and the like may be used for linking epitopes. Inone embodiment, the C-terminus of the MHC class II epitope is directly linked to the N-terminus of the MHC class I epitope via a peptide bond.

The NY-ESO-1 MHC class H restricted T cell epitopes are useful in methods of preventing or treating cancer and useful in diagnostic assay for detecting cancer or precancer in a mammal, including humans. In a diagnostic assay, the NY-ESO-1 HLA class II restricted T cell epitope peptides, variants and derivatives thereof of the present invention are useful in the detection of helper immune response against the tumor antigen, NY ESO-1. Since NY-ESO-1 is exclusively expressed in tumor cells (except normal testis, which is an immune privileged site), the immune response against the protein may be used as an indicator for early cancer detection in patients. As the development of helper T cell responses may be an earlier event than the development of detectable antibodies against the protein, detection of helper T cell responses against the NY-ESO-1 HLA class II restricted T cell epitope peptides are useful in early cancer detection. In a method of detecting helper T cells responses to NY-ESO-1, NY-ESO-1 HLA class II restricted T cell epitope peptides are applied to a substrate or solid support. Lymphocytes from a patient are grown in the presence of the NY-ESO-1 MHC class II restricted T cell epitope peptides in parallel with a control peptide such as a peptide from the flu virus. Specific cytokine release is then measured using such techniques such as ELISPOT and ELISA Detection of an enhanced helper T cell immune response in comparison to the negative controls is indicative of precancer or early cancer in the patient.

The NY-ESO-1 MHC class II restricted binding peptides of the present invention may be used to enhance the generation of antibody and/or CD8+ T cell responses against any given target antigen and/or hapten. Specifically, these peptides may be conjugated or covalently linked to a target antigen peptide, protein or any other hapten against which an antibody and/or CD8+ T cell response is intended. The linkage of the NY-ESO-1 MHC class II restricted epitope peptide to any target hapten or protein should act as a immunologic T cell carrier peptide in enhancing the immunogenicity of any target antigen, hapten or protein in a manner similar to conventional T cell cancer proteins such as tetanus toxoid, albumin and the like. The enhancement may be manifest in higher titer antibody to the target hapten or protein, immunoglobulin class switching form an IgM to an IgG or IgA antibody, and/or elicitation of CD8+ T cell responses. Examples of such target antigen, hapten or protein include but are not limited to TRP2, GP100, TRP1, gp120 and other HIV antigens, malaria antigens, epitopes thereof and the like. Similarly, the nucleic acid sequencing encoding the NY-ESO-1 MHC class II restricted epitope may be incorporated into an engineered vaccine construct along with a nucleic acid sequence encoding a target antigen or epitope thereof for enhancement of the immunogenicity to the target antigen or epitope thereof. Examples regarding this aspect include to incorporate the nucleic acid sequence of Class II epitopes into any vaccine construct in the form of naked DNA or RNA, vaccinia virus, adenovirus, fowlpox virus and the like in frame with the target gene. For example, to enhance the immunogenicity of TRP2 antigen in the form of a plasmid vaccine, the nucleic acid sequence of the NY-ESO-1 class II epitope can be fused in the same open reading frame with the TRP2 gene. The hybrid plasmid is then used to immunize patients instead of using the plasmid according only the TRP2.

The cancer epitopes or variants thereof may be in the form of a derivative in which other constituents are attached thereto such as radiolabels, biotin, fluorescein. A targeting agent may also be attached to the epitope that allow for specific targeting to a specific organ, tumor or cell types. Such targeting agents may be hormones, cytokines, cellular receptors and the like.

The epitope may be prepared in the form of a kit, alone or in combination with other reagents.

Another aspect of the invention is an immunogen or vaccine useful in inducing tumor-specific humoral-mediated immunity against cancer using the NY-ESO-1 MHC class II restricted epitopes of the present invention. The immunogen and vaccine elicit NY-ESO-1 specific CD4+ T lymphocytes and anti-NY-ESO-1 antibody. Optionally, the immunogen and vaccine may comprise an NY-ESO-1 MHC class I restricted epitope for eliciting $CD8^+$ T lymphocytes.

Approaches to cancer immunotherapy can be divided into active or passive categories. Active immunotherapy involves the direct immunization of cancer patients with cancer antigens in an attempt to boost immune responses against the tumor. Passive immunotherapy refers to the administration of immune reagents, such as immune cells or antibodies with antitumor reactivity with the goal of directly mediating antitumor responses.

Most prior attempts at active immunotherapy utilized either intact cancer cells or cancer cell extracts with the expectation that these materials contained tumor antigens in an amount and form capable of stimulating immune responses. The molecular identification of cancer antigens and epitopes however, has open new possibilities for developing immunotherapies for the treatment of human cancer. A summary of some of these approaches is presented in Table 1.

TABLE 1

Cancer Therapies Based on the Molecular
dentification of Cancer Antigens

1. Active immunotherapy with:
   a. Immunodominant peptides or epitopes
      1) alone
      2) combined with adjuvants
      3) linked to helper peptides, lipids or liposomes
      4) pulsed onto antigen presenting cells
   b. Immunodominant peptides with amino acids substitutions to increase binding to MBC molecules
   c. Proteins alone or combined with adjuvants
   d. "Naked" DNA encoding cancer antigens
      1) "gene gun" for intradermal injection
      2) intramuscular injection
      3) linked to lipids
   e. Recombinant viruses such as vaccinia, fowlpox or adenovirus encoding
      1) cancer antigens or epitopes alone
      2) cancer antigens or epitopes plus genes encoding cytokines, costimulatory molecules, or other genes to enhance the immune response
   f. Recombinant bacteria such as BCG, Salmonella or Listeria encoding cancer antigens alone or in combination with immunostimulatory molecules
2. Active immunotherapy (above) followed by the administration of immunostimulatory cytokines.
   1. IL-2
   2. IL-6
   3. IL-10
   4. IL-12
   5. LL-15,
      and the like.
3. Passive immunotherapy with anti-tumor lymphocytes raised by in vitro sensitization of TIL or PBL to
   1. immunodominant peptides pulsed onto antigen presenting cells (raise $CD8^+$cells)
   2. antigenic proteins coincubated with antigen presenting cells (exogenous antigen presenting pathway to raise $CD4^+$cells).

The insertion of the gene encoding at least one NY-ESO-1 MHC class II specific T cell epitope into high efficiency expression systems such as *E. coli*, yeast or baculovirus and the like provides the opportunity to obtain large amounts of purified tumor epitopes for use in immunization. Alternatively, the immunodominant epitopes may be readily be synthesized in vitro and purified in large amounts for immunization alone or in a form intended to improve their immunogenicity such as in combination with adjuvant, linkage to lipids/liposomes or helper peptides, or pulsed onto antigen presenting cells. Modification of individual amino acids of the immunodominant peptides to improve binding efficiency to MHC class II antigens can potentially increase immunogenicity compared to the native peptide.

Recent techniques utilizing "naked" DNA injected directly into muscle or into the skin have been shown to raise both cellular and humoral immune reactions to encoded antigens (Cooney, E. L., A. C. Collier, P. D. Greenberg, R. W. Coombs, J. Zarling, D. E. Arditti, M. C. Hoffman, S. L. Hu and L. Correy, 1991, *Lancet* 337: 567; Wolff, J. A., R. W. Malone, P. Williams, W. Chong, G. Acsadi, A. Jani, and P. L. Feigner, 1990, *Science* 247: 1465; Davis, H. L., R. G. Whalen, and B. A. Demeniex, 1993, *Hum. Gene Ther.* 4: 151; Yang, N. S., J. Burkholder, B. Roberts, B. Martinelli, and D. McCabe, 1990, *Proc. Nail. Acad. Sci. USA* 87: 9568; Williams, R. S., S. A. Johnston, M. Riedy, M. J. DeVit, S. G. McElligott, and J. C. Sanford, 1991, *Proc. Natl. Acad. Sci. USA* 88: 2726; Fynan, E. R., Webster, D. H. Fuller, J. R Haynes, J. C. Santoro, and H. L. Robinson, 1995, *Proc. Natl. Acad. Sci. USA* 90: 11478; Eisenbraum, M. D., D. H. Fuller, and J. R. Haynes, 1993, *DNA and Cell Bio.* 12: 791; Fuller, D. H. and J. R. Haynes, 1994, *AIDS Res. Hum. Retrovir.* 10(11): 1433; Acsadi, G., G. Dickson, D. R. Love, A. Jani, F. S. Walsh, A. Gurusinghe, J. A. Wolff, and K. E. Davies, 1991, *Nature* 352: 815). Techniques using nonviable DNA vectors have the advantage of ease of preparation and safety of administration. The nucleic acid sequence of the present invention is useful as an immunogen and as a DNA vaccine against cancer. The nucleic acid sequence of the present invention of the NY-ESO-1 MHC class II specific T cell epitopes or a nucleic acid sequence encoding a full length NY-ESO-1 protein having one or more variant NY-ESO-1 MHC class II restricted T cell epitopes thereof may be administered using a gene gun in amounts to elicit a humoral response against a cancer cell. Nanogram quantities are useful for such purposes.

An effective form of immunization involves the incorporation of genes encoding immunogenic molecules into recombinant bacteria such as BCG, *Salmonella* or *Listeria* or into recombinant viruses such as vaccinea, fowipox or adenovirus and the like. The genes encoding the NY-ESO-1 MHC class II specific T cell epitope can be expressed either alone or in combination with genes encoding immunostimulatory molecules or other genes which can enhance the immune response following infection. The construct may additionally comprise a gene encoding an additional NY-ESO-1 MHC class II restricted T cell epitope and/or at least one NY-ESO-1 MHC class I specific T cell epitope.

Studies with model tumor antigens in murine models have shown that incorporation of the gene for interleukin-2 (IL-2) or B7.1 can increase the immunogenicity of model tumor epitopes and even mediate the regression of established lung metastases bearing these epitopes. Active immunotherapy followed by the exogenous administration of immunostimulatory cytokines such as IL-2, IL-6, IL-10, EL-12, or IL-15 may also be used to improve immune responses.

Passive immunotherapy with genetically modified immune cells (commonly referred to as adoptive immunotherapy) capable of recognizing human tumor antigens is effective in mediating the regression of cancer in selected patients with metastatic melanoma In vitro techniques have been developed in which human lymphocytes are sensitized in vitro to tumor antigen immunodominant epitopes presented on antigen presenting cells. By repetitive in vitro stimulation cells can be derived with a far greater capacity to recognize human tumor antigens than the TIL that were used to clone the genes encoding these antigens. Thus by repeated in vitro sensitization with the cancer peptides, lymphocytes could be derived with 50 to 100 times more potency of TEL. The adoptive transfer of these cells may be more effective in mediating tumor regression in vivo than are conventionally grown TIL.

In one embodiment, peripheral blood mononuclear cells (PBMC) were stimulated with several candidate DRB1*0401 peptides identified following immunization of DR4-IE transgenic mice. NY-ESO-1 specific CD4+ T cells were generated by in vitro sensitization with a synthetic peptide, ESO p161-180. This CD4+ T cell line recognized NY-ESO-1 peptides presented by HLA DP4, a prevalent MHC class II allele present in approximately 43-70% of Caucasians (52). Moreover, the HLA DP4 haplotype was shared by 91% (10 out of 11) of the melanoma patients who produced high titer Ab against NY-ESO-1, but was not expressed in any of three patients with NY-ESO-1 positive tumors and possessing no detectable Ab. The results of in vitro stimulation demonstrated that the HLA DP4-restricted T cells could be generated from 5 out of 6 patients with NY-ESO-1 Ab. These results suggested that recognition of NY-ESO-1 by CD4+ T cells in the context of DP4 could be connected with the ability of these patients to mount an antibody response against this antigen.

In the methods of preventing or inhibiting cancer, the NY-ESO-1 MHC class II restricted T cell epitopes may be administered via one of several routes including but not limited to intravenous, intramuscular, subcutaneous, intradermal, intraperitoneal, intrathecal, intrapleural, intrauterine, rectal, vaginal, topical, intratumor and the like.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be by nasal sprays, for example, or suppositories. For oral administration, the cancer peptide, tumor antigen, portion or variant thereof is formulated into conventional oral administration form such as capsules, tablets and tonics.

In general, it is desirable to provide the recipient with a dosage of NY-ESO-1 MHC class II restricted T cell epitopes of at least about 1 ng per Kg bodyweight, preferably at least about 1 mg per Kg bodyweight, more preferably at least about 10 mg or greater per Kg bodyweight of the recipient. A range of from about 1 mg per Kg bodyweight to about 100 mg per Kg bodyweight is preferred although a lower or higher dose may be administered. The dose is effective to prime, stimulate and/or cause the clonal expansion of NY-ESO-1 MHC class II specific CD4+ T lymphocytes, which in turn are capable of preventing or inhibiting cancer in the recipient.

The dose is administered at least once and may be provided as a bolus or a continuous administration. Multiple administrations of the dose over a period of several weeks to months may be preferable. Subsequent doses may be administered as indicated.

In a method of treatment, a vaccine comprising the NY-ESO-1 class II restricted T cell epitope is administered to a mammal in an amount effective to prevent cancer in the mammals or to prevent metastasis in a mammal bearing a localized cancer. Optionally, the vaccine may include multiple distinct NY-ESO-1 MHC class II restricted T cell epitopes and/or an NY-ESO-1 MHC class I restricted cancer peptide or epitope to stimulate cytotoxic T lymphocytes.

In a method of reducing tumor burden in animals having tumors the method comprises administration of an effective amount of a NY-ESO-1 MHC class II restricted T cell epitope at a site of tumor burden, said amount is effective to reduce the size of the tumor at the site and may inhibit metastasis from the tumor site.

In another embodiment of a method of treatment, an immunogen comprising the NY-ESO-1 HLA-DP restricted T cell epitope is administered to a mammal in an amount effective to elicit NY-ESO-1 HLA-DP restricted CD4+ T lymphocytes and anti-NY-ESO-1 antibody. The immunogen may be provided alone or in combination with an adjuvant, immunomodulators, and the like.

In another method of treatment, autologous lymphocytes or tumor infiltrating lymphocytes may be obtained from a patient with cancer. The lymphocytes are grown in culture and cancer epitope specific CD4+ lymphocytes expanded by culturing in the presence of NY-ESO-1 MHC class II restricted T cell epitopes alone or in combination with at least one immunostimulatory molecule with cytokines. The epitope specific CD4+ lymphocytes are then infused back into the patient, alone or in combination with the epitope, in an amount effective to reduce or eliminate the tumors in the patient.

After immunization the efficacy of the vaccine can be assessed by production of immune cells that recognize the NY-ESO-1 MHC class II T cell epitope, as assessed by antibody titer, specific lytic activity, specific cytokine production, tumor regression or combination of these. If the mammal to be immunized is already afflicted with cancer or metastasis cancer the vaccine can be administered in conjunction with other therapeutic treatments such as immunomodulators, for example, IL-2, IL-6, IL-10, IL-12, IL-15, interferon, tumor necrosis factor and the like, chemotherapeutic drugs such as cisplatinum, antiviral such as gancyclovir, amphotericin B, antibiotics and the like.

Another aspect of the invention is a DNA sequence of the NY-ESO-1 gene encoding a MHC class II restricted T cell epitope thereof.

In one embodiment, the DNA sequence comprises a portion of SEQ. ID NO.: 1 or 2 and functionally equivalent sequence variants thereof that encode a MHC class II restricted T cell epitope recognized by CD4+ T lymphocytes. Also encompassed by the present invention are nucleic acid sequences complementary, as well as anticomplementary to the portion of SEQ. ID NO: 1 or 2 encoding the MHC class II restricted T cell epitope.

In an embodiment, the DNA sequence encodes an MHC class II restricted T cell epitope comprising at least one of SEQ ID NOS: 4 through 21 or 29-34.

In another embodiment, the DNA sequence encoding an MHC class II restricted T cell epitope comprises:

```
                                          (SEQ. ID NO: 24)
CAG GAT GCC CCA CCG CTT CCC GTG CCA GGG GTG CTT

CTG AAG GAG TTC ACT GTG TCC GGC AAC ATA CTG ACT

ATC CGA CTC
``` or functional portion or variant thereof.

In another embodiment, the DNA sequence encoding an MHC class II restricted T cell epitope comprises:

(SEQ ID NO: 25)
AGA CCA CCG CCA ACT GCA GCT CTC CAT CAG CTC CTG

TCT CCA GCA GCT TTC CCT GTT GAT or functional portion or variant thereof.

In another embodiment, the DNA sequence comprises:

(SEQ ID NO: 26)
TGG ATC ACG CAG TGC TTT CTG CCC GTG TTT TTG GCT

CAG CCT CCC TCA GGG CAG AGG CGC, or functional portion or variant thereof.

Another aspect of the invention is a DNA sequence of the NY-ESO-1 gene encoding a HLA-DP restricted CD4+ T cell epitope thereof.

In one embodiment, the DNA sequence comprises a nucleic acid sequence encoding one or more SEQ. ID NOS.: 51 through 64 and functionally equivalent sequence variants thereof that encode an HLA-DP restricted T cell epitope recognized by CD4+ T lymphocytes. Also encompassed by the present invention are nucleic acid sequences complementary, as well as anticomplementary to the nucleic acid sequence encoding the HLA-DP restricted T cell epitope.

Due to degeneracy in the generic code, variations in the DNA sequence will result in translation of an equivalent NY-ESO-1 epitope. As a result, substitutions are included in the ambit of the invention as long as the substitution results in expression of an NY-ESO-1 epitope that is recognized by NY-ESO-1 cancer antigen HLA-class II restricted CD4+ T cells.

All or part of an open reading frame DNA sequence-from the NY-ESO-1 gene may be used as probes to identify and isolate the homologs of the NY-ESO-1 MHC class II restricted T cell epitope in other mammalian species. In one embodiment, a human cDNA sequence is used to screen a mammalian cDNA library for a murine homolog nucleic acid sequence. Positive clones are selected and sequenced. Examples of tissue sources from which the cDNA library can be synthesized include but are not limited to dermis, epidermis, solid tumors, melanomas, melanocytes, and the like. One skilled in the art will understand the appropriate hybridization conditions to be used to detect the homologs. Conventional methods for nucleic acid hybridization construction of libraries and cloning techniques are described in Sambrook et al, (eds) (1989) in "Molecular Cloning. A Laboratory Manual" Cold Spring Harbor Press, Plainview, N.Y. and Ausubel et al (eds) in "Current Protocols in Molecular Biology" (1987), John Wiley and Sons, New York, N.Y.

Another aspect of the invention are nucleic acid probes for the detection and quantification of RNA that transcribes the NY-ESO-1 MHC class II restricted T cell epitopes of the present invention in biologic samples isolated from a mammal with cancer. Alterations in the level of RNA relative to a control RNA sample is useful in diagnosis and prognosis of the disease in the mammal.

In one embodiment, mRNA is derived from tissue of a patient suspected of having cancer or precancer and compared with mRNA derived from a healthy control subject A quantitative and/or qualitative increase of the mRNA encoding a NY-ESO-1 MHC class II restricted T cell epitope of the present invention in the patient, as compared to the control, is indicative of cancer or precancer in the patient. The mRNA may be detected using oligonucleotide probes hybridizable with the mRNA.

Combinations of oligonucleotides pairs based on the sequence encoding the NY-ESO-1 MHC class II restricted T cell epitopes of the present invention may be used as PCR primers to detect mRNA in biological samples using the reverse transcriptase polymerase chain reaction (RT-PCR) process for amplifying selected RNA sequences. The present invention also encompasses in situ PCR and in situ RT-PCR for detection of DNA and RNA encoding the NY-ESO-1 MHC class II restricted T cell epitopes. The technique is preferred when the copy number of a target nucleic acid is very low, or when different forms of nucleic acids must be distinguished. The method is especially useful in detecting and differentiating precancer and cancer cells from normal cells.

The present invention also encompasses antisense oligonucleotides which bind to certain complementary ('sense') regions on mRNA resulting in inhibition of synthesis of NY-ESO-1. Such antisense oligonucleotides are single stranded nucleic acid of about 12 to about 25 mononucleotides and are antisense to the sequence encoding the NY-ESO-1 MHC class II restricted T cell epitopes of the present invention. Such antisense oligonucleotides may be made by methods known in the art as described by Uhlmann, E. et al. Antisense oligonucleotides, structure and function of In: Molecular Biology and Biotechnology Ed. R. A. Meyers, VCH Publishers, Inc., New York, N.Y., 1995, pp. 3844.

The present invention also encompasses a vector comprising the DNA sequence encoding at least one or more NY-ESO-1 MHC class II restricted T cell epitopes. The vector may comprise a DNA sequence encoding a full length NY-ESO-1 protein having one or more variant NY-ESO-1 MHC class II restricted T cell epitopes. Optionally the vector may also comprise a DNA sequence encoding at least one immunostimulatory molecule. The vector may also comprise a DNA sequence encoding at least one or more NY-ESO-1 MHC class I restricted T cell epitopes. The vector may also contain a gene encoding green fluorescent protein for use in detecting localization of NY-ESO-1 MHC class II restricted T cell epitopes in cells and tissues.

Eukaryotic expression vectors include but are not limited to retroviral vectors, vaccinia virus vectors, adenovirus vectors, herpes virus vectors, fowlpox virus vectors, baculovirus vectors, human papillomavirus vectors, equine encephalitis vectors, influenza virus vectors and the like.

The present invention encompasses novel recombinant virus expressing at least one NY-ESO-1 MHC class II restricted T cell epitope encoded by an open reading frame nucleic acid sequence of a gene, fragments or variants thereof. The recombinant virus may also express at least one immunostimulatory molecule. The recombinant virus is capable of eliciting or upregulating a humoral immune response in a mammal for the purpose of preventing or treating cancer in the mammal, particularly humans.

A host cell infected with the recombinant virus expresses one or more NY-ESO-1 MHC class II restricted T cell epitopes, alone or in combination with at least one immunostimulatory molecule. The host cell may also be infected with a recombinant virus expressing an HLA class II molecule.

Methods for constructing and expressing exogenous gene products from recombinant vaccinia virus vectors are disclosed by Perkus et al *Science* 229: 981-984, 1985, Kaufman et al *Int. J. Cancer* 48: 900-907, 1991, Moss *Science* 252: 1662, 1991, Smith and Moss *BioTechniques* November/December, p. 306-312, 1984, and U.S. Pat. No. 4,738,846. Sutter and Moss (*Proc. Nat'l Acad. Sci. U.S.A.* 89: 10847-10851, 1992) and Sutter et al (*Virology* 1994) disclose the construction and use as a vector, the non-replicating recombinant Ankara virus (MVA, modified vaccinia Ankara) which may be used as a viral vector in the present invention. Baxby and Paoletti (*Vaccine* 10: 8-9, 1992) disclose the construction and use as a vector, a non-replicating poxvirus, including canarypox virus, fowlpox virus and other avian species for use as a viral vector in the present invention.

The vectors of the present invention may be placed in an appropriate host cell for the expression of the NY-ESO-1 MHC class II restricted T cell epitope. Eukaryotic host cell lines include, but are not limited to COS cells, CHO cells, Hela cells, NE/3T3 cells, insect cells, antigen presenting cells such as dendritic cells and the like. Optionally the host cell may also express a stimulatory molecule. In the case where the host cells express both the NY-ESO-1 MHC class II restricted T cell epitope in combination with at least one MHC (or HLA) class II molecule, it is preferable that a eukaryotic expression system be used to allow for proper glycosylation. The expression of both the cancer epitope and the immunostimulatory molecule by the host cell provides the necessary MHC class II restricted peptide to specific T cells and the appropriate signal to the T cell to aid in antigen recognition and proliferation or clonal expansion of antigen specific T cells. The overall result is an upregulation of the immune system. The upregulation of the immune response is manifest by an increase in cancer antigen specific $CD^4+$ lymphocytes and other effector cells of humoral immunity for inhibition of the growth of cancer or precancer cells.

The DNA may be inserted into the host cell by transfection, transduction, liposomes and the like by methods known in the art. (Sambrook et al, 1989, in: "Molecular Cloning A Laboratory Manual", Cold Spring Harbor press, Plainview, N.Y.). For liposomes, cationic lipids are preferred, for example, polycationic lipid, dimyristyloxypropyl-3-dimethyl-hydroxyethyl ammonium (DMRIE) complexed with the neutral phospholipid dioleoyl phosphatidyl-ethanolamine (DOPE) as disclosed by Nabel, E. G. et al, 1992, *Hum. Gene. Ther.* 3: 367-275; Nabel, G. J. et al, 1992, *Hum. Gene Ther.* 3: 649-656; Stewart, M. J. et al 1992 *Hum. Gene Ther.* 3: 399-410; Nabel, G. J. et al 1993 *Proc. Natl. Acad. Sci.* USA 90: 11307-11311; and Harrison, G. S. et al 1995 *Bio Techniques* 19: 816-823.

The recombinant NY-ESO-1 MSC class II restricted T cell epitopes expressed by the host cells may be purified from cell lysates or cell supernatants by standard protein purification procedures known in the art. These include but are not limited to molecular sieve chromatography, ion-exchange chromatography, isoelectric focusing, gel electrophoresis, affinity chromatography, HPLC, reverse phase HPLC and the like. (Ausubel et al, 1987, *Current Protocols in Molecular Biology*, John Wiley and Sons, New York, N.Y.). Immunoaffinity chromatography may also be used for purification using anticancer protein antibodies or antigen binding fragments thereof as described herein, as the immunoaffinity agent.

The recombinant virus may also be used as a therapeutic or vaccine. In such uses it is desirable to provide the recipient with a dosage of recombinant virus in the range of from about $10^5$ to about $10^{10}$ plaque forming units/mg mammal, although a lower or higher dose may be administered.

The recombinant viral vector may be introduced into a mammal either prior to any evidence of cancer such as melanoma or to mediate regression of the disease in a mammal afflicted with a cancer such as melanoma. Examples of methods for administering the viral vector into mammals include, but are not limited to, exposure of cells to the recombinant virus ex vivo, or injection of the recombinant virus into the affected tissue or intravenous, subcutaneous, intradermal, intramuscular and the like administration of the virus. Alternatively, the recombinant viral vector or combination of recombinant viral vectors may be administered locally by direct injection into the cancerous lesion or topical application in a suitable pharmaceutically acceptable carrier. The quantity of recombinant viral vector, carrying the nucleic acid sequence of interest is based on the titer of virus particles. A preferred range for immunization is about $10^5$ to $10^{10}$ virus particles per mammal, preferably a human.

The invention provides a transgenic animal which has incorporated into its genome one or more copies of the DNA sequence encoding at least one NY-ESO-1 MNC class II restricted T cell epitope. The general method of producing transgenic animals is described in Krimpenfort et al U.S. Pat. No. 5,175,384, Leder et al U.S. Pat. No. 5,175,383, Wagner et al U.S. Pat. No. 5,175,385, Evans et al U.S. Pat. No. 4,870,009 and Berns U.S. Pat. No. 5,174,986. The incorporation of the gene results in overexpression, altered expression or expression of multiple forms or variants of the NY-ESO-1 MHC class II restricted T cell epitope. The resulting transgenic animal are useful in studies of the development of cancer or tumor antigen of the present invention The animal model is useful in screening vaccines and chemotherapeutic drugs for cancer treatment. The transgenic animal is also useful in studies of the development of cancer.

This invention further comprises an antibody or antigen binding portion thereof elicited by immunization with the NY-ESO-1 MHC class II restricted T cell epitope of the present invention. In the case where the NY-ESO-1 MHC class II restricted T cell epitope is comprised of only a few amino acids, the epitope may be conjugated to a carrier protein in order to elicit an antibody response. Carrier proteins such as KLH, tetanus toxoid, albumin and the like and methods of conjugation are known in the art. The antibody has specificity for and reacts or binds with the NY-ESO-1 MHC class II restricted T cell epitope of the present invention, as well as with the intact NY-ESO-1 protein, and naturally processed forms of the NY-ESO-1 protein.

Exemplary antibody molecules are intact immunoglobulin molecules, substantially intact immunoglobulin molecules or these portions of an immunoglobulin molecule that contain the antigen binding site, including those portions of immunoglobulin molecules known in the art as F (ab), F (ab), F (ab')$_2$, humanized chimeric antibody, and F(v). Polyclonal or monoclonal antibodies may be produced by methods known in the art. (Kohler and Milstein (1975) *Nature* 256, 495-497; Campbell "Monoclonal Antibody Technology, the Production and Characterization of Rodent and Human Hybridomas" in Burdon et al (eds.) (1985) "Laboratory Techniques in Biochemistry and Molecular Biology", Vol. 13, Elsevier Science Publishers, Amsterdam). The antibodies or antigen binding fragments may also be produced by genetic engineering. The technology for expression of both heavy and light chain genes is the subject of the PCT patent applications: publication number WO 901443, WO 9014424, Huse et al (1989) *Science* 246: 1275-1281, and U.S. Pat. No. 4,946,778. Humanized immunoglobulins having one or more complementary determining regions and methods of making the antibodies are disclosed in U.S. Pat. Nos. 5,585,089 and 5,530,101.

In one embodiment, the antibodies of the invention are used in immunoassays to detect NY-ESO-1 peptides or portions containing the MHC class II restricted T cell epitope in biological samples. The antibodies or antigen binding fragments thereof may be used to detect cancer peptides in tissue biopsy samples from a mammal afflicted with cancer. Assessment of the NY-ESO-1 MHC class II restricted T cell epitope in a diseased tissue can be used to prognose the progression of the disease in a mammal or may diagnose the efficacy of a treatment The immunoassay may be a radioimmunoassay, Western blot assay, immunofluorescent assay, enzyme immunoassay, chemiluminescent assay, immunohistochemical assay and the like and may be performed in vitro, in vivo or in situ. Standard techniques known in the art for ELISA are described in "Methods in Immunodiagnosis", 2nd Edition, Rose and Bigazzi, eds. John Wiley & Sons, 1980; Campbell et al "Methods and Immunology", W. A. Benjamin, Inc., 1964; and Oellerich, M. 1984, *J. Clin. Chem. Clin. Biochem.* 22: 895-904. Conventional methods for immunohistochemistry are described in Harlow and Lane (eds) (1988) In "Antibodies A Laboratory Manual", Cold Spring Harbor Press, Cold Spring Harbor, N.Y.; Ausbel et al (eds) (1987) In Current Protocols In Molecular Biology, John Wiley and Sons (New York, N.Y.). Biological samples appropriate for such detection assays include but are not limited to cells, tissue biopsy, whole blood, plasma, serum, sputum, cerebrospinal fluid, pleural fluid, urine and the like.

The antibodies or antigen binding fragments of the present invention may also be used in immunotherapy. The antibodies or antigen binding fragment thereof is provided to a mammal in an amount sufficient to prevent, lessen or attenuate the severity, extent or duration of the cancer.

All articles and patents referred to are incorporated herein by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

EXAMPLE 1

Materials and Methods

Purification and Analysis of Recombinant NY-ESO-1 Protein: To construct a bacterial expression vector encoding the full-length NY-ESO-1 gene, we generated a PCR fragment by using a pair of primers, ESO-5p (5'GCTCCGGA CATATGCAGGCCG AAGGCCGGGG) (SEQ D NO: 35) containing an NdeI site and ESO-3p (5'AAGGGG CTCGAGGCT GGGCTTAGCGCCTCT) (SEQ ID NO: 36) containing an XhoI site. After digestion with restriction enzymes and gel purification of the PCR product, a DNA fragment encoding NY-ESO-1 was fused to DNA encoding a poly-histidine peptide in frame in pET-28(+) (Novagen, Madison, Wis.). A similar strategy was also used to construct an expression vector for a truncated NY-ESO-1, ESO1-74, which contained only the first 74 amino acid residues. *E. coli* strain BL21(DE3) bearing the correct plasmid construct was grown at 37° C. to log phase, then induced for protein production by adding isopropyl-d-thiogalactoside (IPTG) to a final concentration of 0.5 mM and shaking for 3 hours. Soluble fractions of bacterial extract were obtained; and NY-ESO-1 was purified by $Ni^{2+}$ affinity chromatography. SDS-PAGE analysis of the purified protein was performed as previously reported (25). The N terminal sequence of the purified protein was determined by automatic Edman degradation.

Serum mod PBMC: Sera from patients with metastatic melanoma were stored at −80° C. Sera of normal donors were obtained from the Blood Bank at the Clinical Center of NIH. The MHC class II genotype of patient TE with metastatic melanoma was HLA-DR1*0401, 1*1501. The patient was treated with the gp100:209-217(210M) peptide plus high does of IL-2, and experienced an objective tumor regression.

Detection of Antibodies against NY-ESO-1 Protein: About 50 ng of purified NY-ESO-1 protein diluted in 50 1 PBST (phosphate-buffered saline with 0.1% Tween 20) was adsorbed to each well of a 96-well MaxiSorp plate (Nunc, Denmark) overnight at room temperature. Control plates were coated with 150 ng BSA/well. Plates were blocked with 5% dry milk in PBST for at least 2 hours, washed, and were loaded with 100 1 of diluted serum samples. All serum samples were diluted at 1:25, 1:250, and 1:2500 with 3% dry milk in PBST. Each sample at the three different dilutions was loaded onto NY-ESO-1-coated plates as well as BSA-coated plates. After one hour incubation at room temperature, plates were washed, and loaded with secondary antibody (goat anti-human IgG conjugated with horseradish peroxidase, Sigma Co., St. Louis, Mo.) diluted with 1% dry milk in PBST. Plates were developed after a 0.5-hour incubation, and absorbance at 450 nm was read by using an ELISA reader (Dynatech, Chantilly, Va.). A positive reaction was defined as an O.D. value against NY-ESO-1 that exceeded the mean O.D. value plus 3 times standard derivations of normal donors at serum dilutions of both 1:25 and 1:250. Western blot was performed as described (24) to confirm the specificity of the antibody in a few representative sera samples.

Cell Lines and Antibodies: Melanoma lines F049 and F050 were early cultures of fine needle asparate samples, provided by Adam Riker at the Surgery Branch of NCI. All other melanoma lines and EBV B lines were generated and maintained in RPMI 1640 (Life Technologies, Rockville, Md.) supplemented with 10% fetal calf serum (Biofluid, Inc., Gaithersburg, Md.). 293DR1 and 293MDR4 were genetically engineered to express human invariant chain, DMA, DMB and DR molecules, and were cultured in RPMI 1640 supplemented with 10% fetal calf serum (15). Culture medium for murine lymphocytes was RPMI 1640 with 0.05 mM-mercaptoethanol, 5 CU/ml IL-2 plus 10% fetal calf serum provided by Hyclone Inc. (Logan, Utah). Medium used for human T cell culture was RPMI 1640 with 0.05 mM-mercaptoethanol, 50 CU/ml IL-2 plus 10% human AB serum provided by Sigma Co. (St. Louis, Mo.). Antibody blocking experiments were performed as previously described (15). Hybridoma HB55 and HB95 were obtained from American Type of Cell Culture (ATCC; Manassas, Va.). Control antibody was purchased from Pharmingen Int. (San Diego, Calif.).

Transgenic Animals and Immunization Procedures: HLA-DR4 transgenic (DR4-Tg) mice were murine class II-deficient, and expressed HLA-DR-IE- and HLA-DR1*0401-IE-chimeric molecules (26). Founder mice were obtained through Paul Lehmann at Case Western Reserve University. Mice were inbred and maintained at Biocon Inc. (Rockville, Md.). Female mice aged between 6 and 10 weeks were immunized with the full-length recombinant NY-ESO-1 protein. About 50 microgram of purified protein were emulsified in complete Freund's adjuvant (CFA), divided evenly and given to each mouse via subcutaneous injection into rear foot pads and the base of tail. Eleven days after the injection, mice were sacrificed and the bilateral hindlimb popliteal and the inguinal lymph nodes were harvested. Single cell suspensions were obtained from the lymph nodes of two immunized animals, and followed by in vitro stimulation.

Peptide Synthesis: Synthetic peptides used in this study were made using a solid phase method on a peptide synthesizer (Gilson Co. Inc., Worthington, Ohio) at the Surgery Brach of NCI. The purity of each peptide was evaluated by mass spectrometry (Bio-synthesis, Inc., Lewisville, Tex.).

In Vitro Sensitization (IVS) Procedure amid Cytokine Release Assays: Peptides at a final concentration of 10 M were mixed with $2.5 \times 10^5$ mouse lymphocytes for a week before cytokine release assays were conducted. For IVS of human PBMC, $2.5 \times 10^5$ cells were pulsed with peptides at 10 M concentration and incubated in each well of a flat-bottomed 96-well plate. After two in vitro stimulations, cells were tested against various targets and supernatants were harvested for cytokine release assays. Rapid expansion and cloning of human T cells were performed as described (20).

Peptide at a final concentration of 10 M or protein at a final concentration of 5 g/ml were pulsed onto target cells. After 4 hr incubation, cells were washed in serum-free RPMI medium, and approximately $3 \times 10^4$ target cells were incubated with the same number of TE4-1 cells overnight, and cytokine release was measured using GM-CSF ELISA kits (R&D Systems, Minneapolis, Minn.) for human or IFN-kits (Endogen, Inc. Woburn, Mass.) for mouse. Other cytokines such as human IFN-, IL-10, TNF-, and IL-4 were measured using ELISA kits from Endogen Inc. or R&D Systems according to the manufacturer's instructions.

EXAMPLE 2

Recombinant NY-ESO-1 Protein and Detection of NY-ESO-1 Reactive Antibody

NY-ESO-1 reactive antibodies and CTL have been reported in patients with cancer (19-22). It thus appeared that NY-ESO-1 specific CD4+ T cells might play a role in orchestrating the development of antibodies as well as CTLa against the NY-ESO-1 antigen However, no CD4+ T cell epitopes from NY-ESO-1 have been reported thus far. In order to identify MHC class II-restricted CD4+ T cell epitopes, we began by purifying NY-ESO-1 protein from a bacterial expression system as the starting material. To facilitate NY-ESO-1 expression and protein purification, a cDNA fragment encoding NY-ESO-1 was fused to a polyhistidine tag in frame located at the N-terminus in the pET28 expression vector and a high-level production of recombinant protein was obtained. Several milligrams of the NY-ESO-1 protein were purified by using a $Ni^{2+}$-charged affinity chromatography column. The purified protein showed an apparent molecular weight of approximately 26 kDa on an SDS polyacrylamide gel (FIG. 2A). To confirm the identity of the purified protein, N terminal microsequencing of protein was performed by automatic Edman degradation. All 25 amino acid residues obtained by Edman degradation matched the predicted amino acid sequences (data not shown). A short version of NY-ESO-1 containing the first 74 amino acid residues, ESO1-74, was also purified by the same approach (FIG. 2A).

Figure 2B:
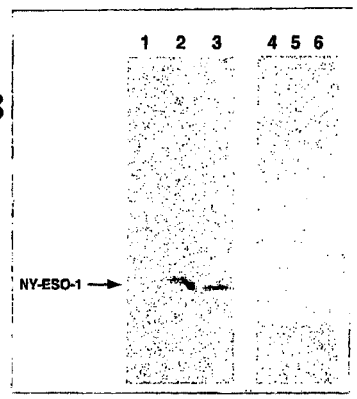
Figure 2C:
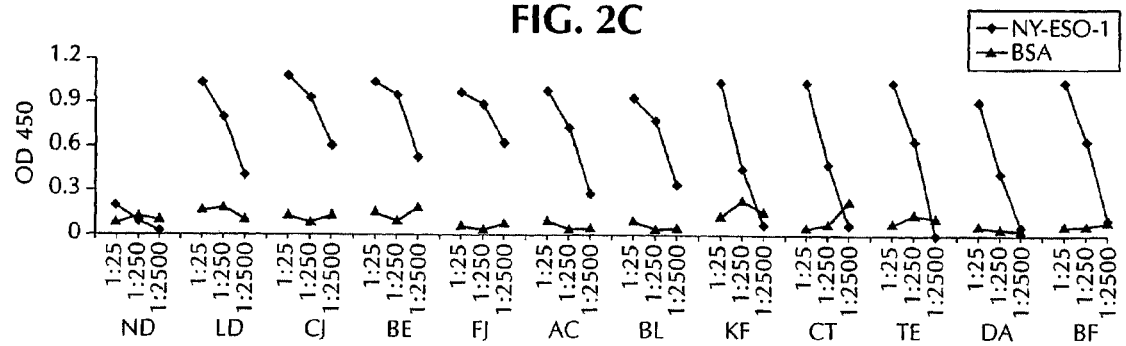

To determine whether melanoma patients developed antibodies against the NY-ESO-1 protein, sera from 88 metastatic melanoma patients enrolled in cancer vaccine treatment protocols in the Surgery Branch, NCI were screened. Sera from 8 normal donors were used as controls for screeing. Eleven of 88 patients (13%) were found to have high titers of antibodies against NY-ESO-1 (FIG. 2C). This data was consistent with results obtained by other groups (22). To exclude the possibility that patients' sera reacted with a minor contaminant present in the purified NY-ESO-1 protein, Western blot was performed using representative sera samples. FIG. 2B showed that the NY-ESO-1 reactive sera from a patient reacted only with cell lysates from NY-ESO-1 expressing bacteria and the purified NY-ESO-1 protein, but not with extracts from bacteria containing the control vector. A non-reactive serum sample was also tested (FIG. 2B, lanes 4, 5, 6).

EXAMPLE 3

Identification of Putative MHC Class II-Restricted Epitopes from HLA-DR4-Transgenic Mice To identify CD4+ T cell epitopes, DR4-transgenic mice were immunized in the tail base and rear foot pads with approximately 50 g of full-length NY-ESO-1 protein in CFA. Eleven days after the injection, single cell suspensions obtained from bilateral hindlimb popliteal and inguinal lymph nodes of two immunized mice were prepared and used for in vitro sensitization with synthetic peptides derived from the NY-ESO-1 protein based on the predicted peptide binding properties of the HLA-DR4 molecules (27).

Figure 3:
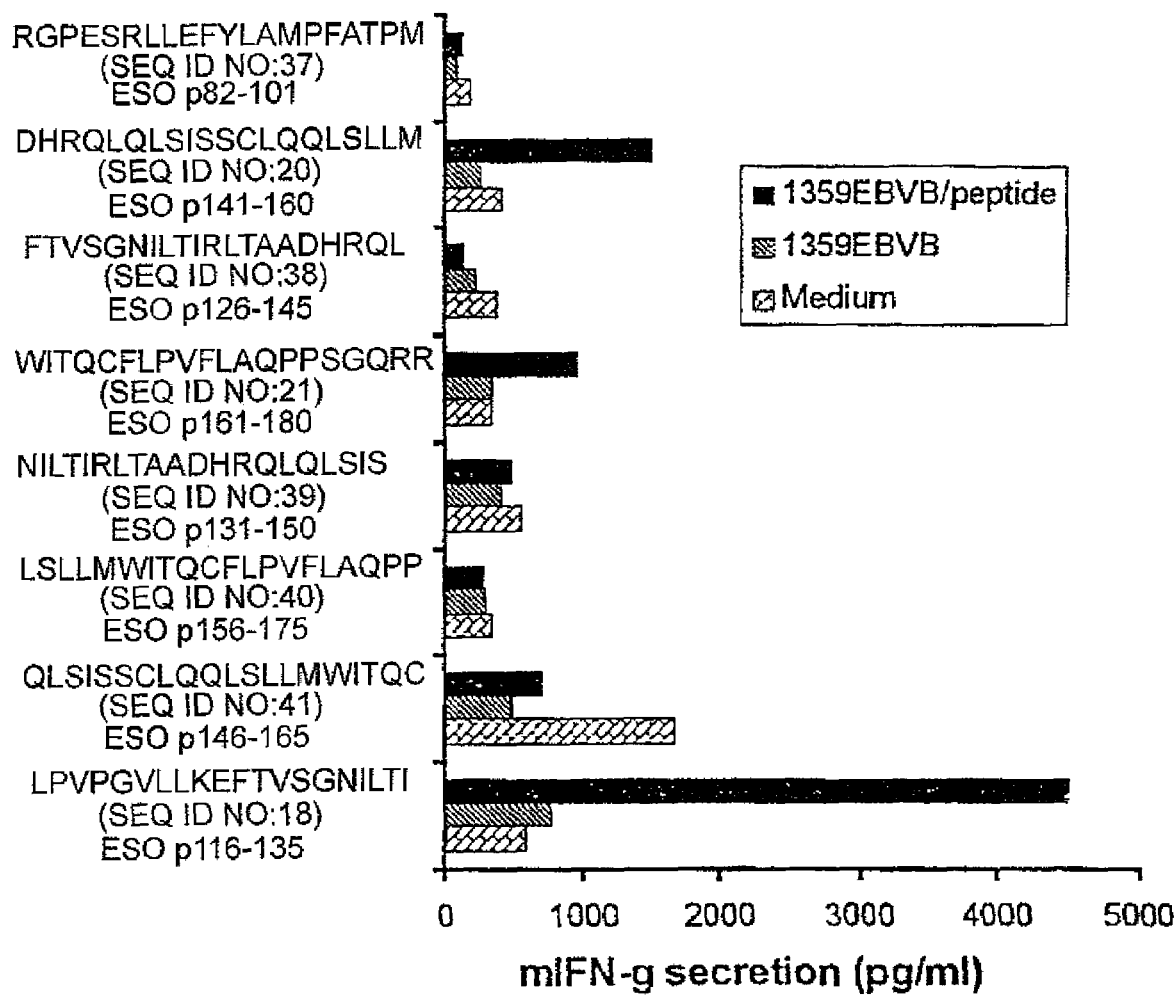
FIG. 3. Testing of putative NY-ESO-1 epitopes using HLA-DR4-Tg mice immunized with NY-ESO-1 protein. Eight peptides based on the predicted binding affinity to HLA-DR4 were used for in vitro sensitization of lymphocytes from immunized mice. Murine lymphocytes were tested for IFN-production against either medium alone, 1359EBV B (HLA DR4$^+$) cells alone or 1359EBV B cells pulsed with the peptide used for in vitro stimulation.

Eight high-binding peptides containing amino acid sequence segments predicted to bind to HLA-DR4 were used for the in vitro sensitization experiments. Six days after the initial in vitro sensitization, murine lymphocytes were tested for cytokine release against human HLA-DR4 positive 1359EBV B cells alone and 1359EBV B pulsed with the corresponding peptide used for stimulation. Three peptides were recognized by murine T cells based on cytokine secretion from T cells while other 5 peptides showed no recognition (FIG. 3). The ESO p116-135 showed the strongest activity among the positive peptides, suggesting that this peptide might contain an epitope presented by the HLA-DR4 molecule for T cell recognition. This peptide was thus chosen for further analysis.

EXAMPLE 4

Generation of Human CD4+ T Cells Specific for NY-ESO-1

PBMCs from patient TE, who had high-titered antibodies against NY-ESO-1 (FIG. 2C), were used for in vitro stimulation with the ESO p116-135 peptide. After one week of in vitro stimulation, PBMC from patient. TE showed marked expansion. IL-2 was added in the second week of stimulation. The cell line thus established was named TE4-1, which continued growth for more than two weeks in the presence of 20 CU/ml IL-2. The TE4-1 T cells were 90% CD4+ T cells based on FACS analysis. TE4-1 contained Th1-type CD4+ T cells as they secreted GM-CSF, IFN- and TNF, but not IL-10 or IL-4 (data not shown). After depletion of a few percent of CD8+ T cells, the purified population of CD4+ T cells still retained its reactivity. Some T cell clones derived from TE4-1 cell line were also shown to recognize the ESO p116-135 peptide (data not shown).

Figure 4A:
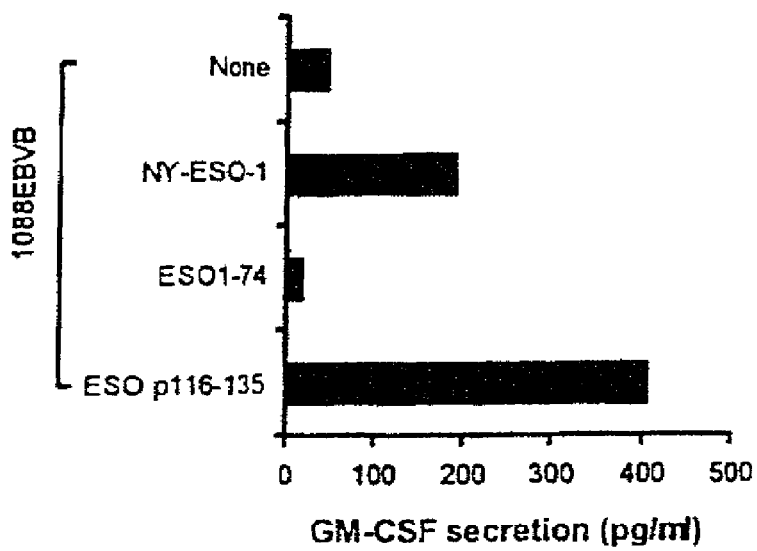

TE4-1 recognized EBV B cells pulsed with the full-length NY-ESO-1 protein as well as the ESO p116-135 peptide in the context of HLA-DR4, but not with the truncated NY-ESO-1 protein containing the first 74 amino acids (FIG. 4A). The TE4-1 cell line was also reactive specifically with DR4 positive-dendritic cells infected with adenovirus encoding NY-ESO-1, but not adenovirus encoding the green fluorescence protein (data not shown).

Figure 4B:
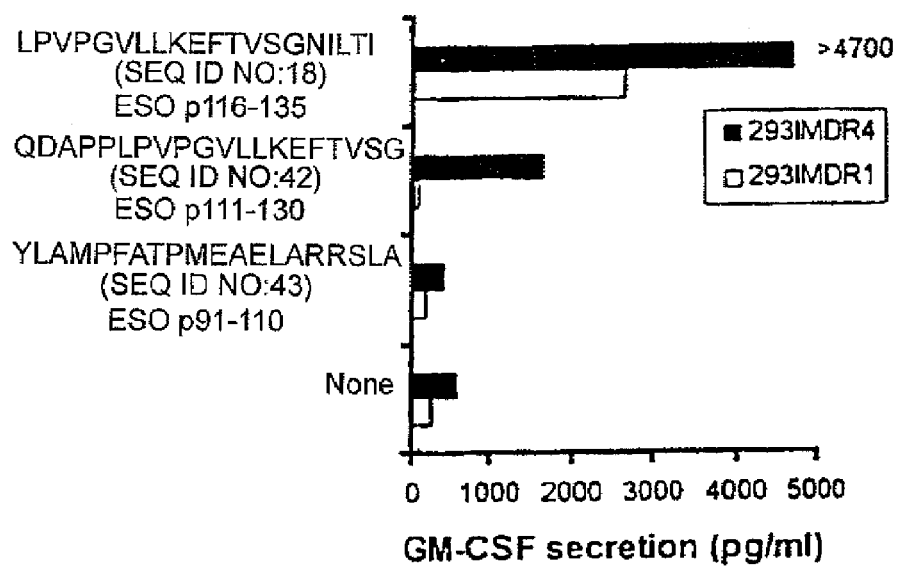
Figure 4D:
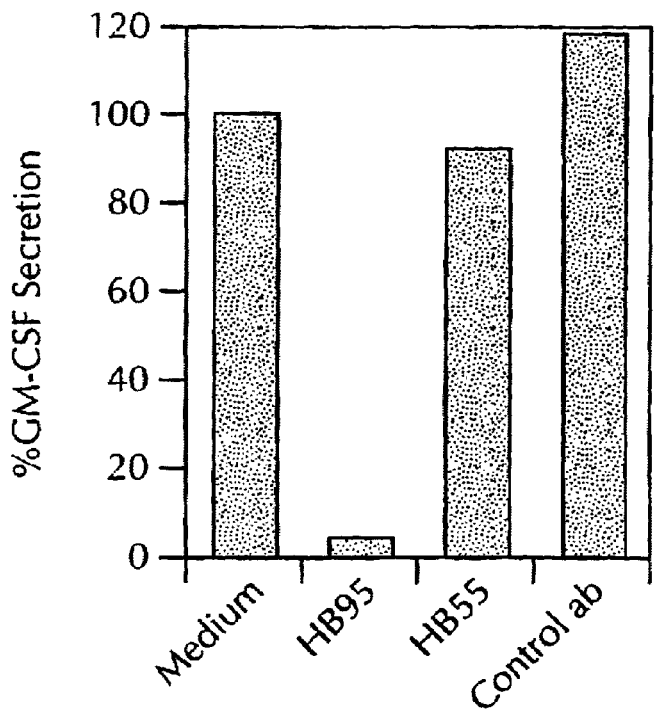
Figure 4E:
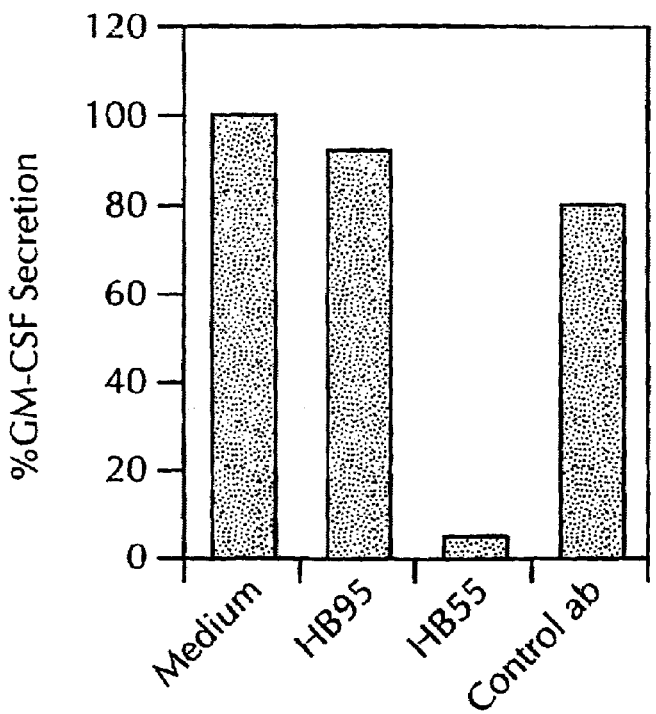

To test whether T cell recognition by TE4-1 was restricted by HLA-DR4, two overlapping peptides (ESO p116-135 and ESO p111-130) and a control peptide (ESO p91-110) were pulsed onto 293IMDRI and 293IMDR4 cells in serum-free medium. Cells were washed and subsequently incubated with TE4-1 cells overnight. As shown in FIG. 4B, both peptide 116-135 and peptide 111-130 were recognized by TE4-1 in the context of HLA-DR4. Interestingly, peptide 116-135 was also capable of stimulating cytokine secretion from T cells when pulsed onto 293IMDR1 cells. No activity was detected with 293IMDR4 pulsed with the control ESO p91-110 peptide (FIG. 4B). The recognition of ESO-p116-135-pulsed 293IMR4 was completely inhibited by an anti-HLA-DR antibody (HB55), but not by the control and anti-HLA-class I antibodies (HB95) (FIG. 4C). A gp100-specific $CD8^+$ T cell line (CTL-C3G1) and an HLA-DR1-restricted $CD4^+$ T cell line (T3-80) were used as specificity controls for the antibody blocking.

EXAMPLE 5

Recognition of Tumor Cells by TE4-1

Figure 5:
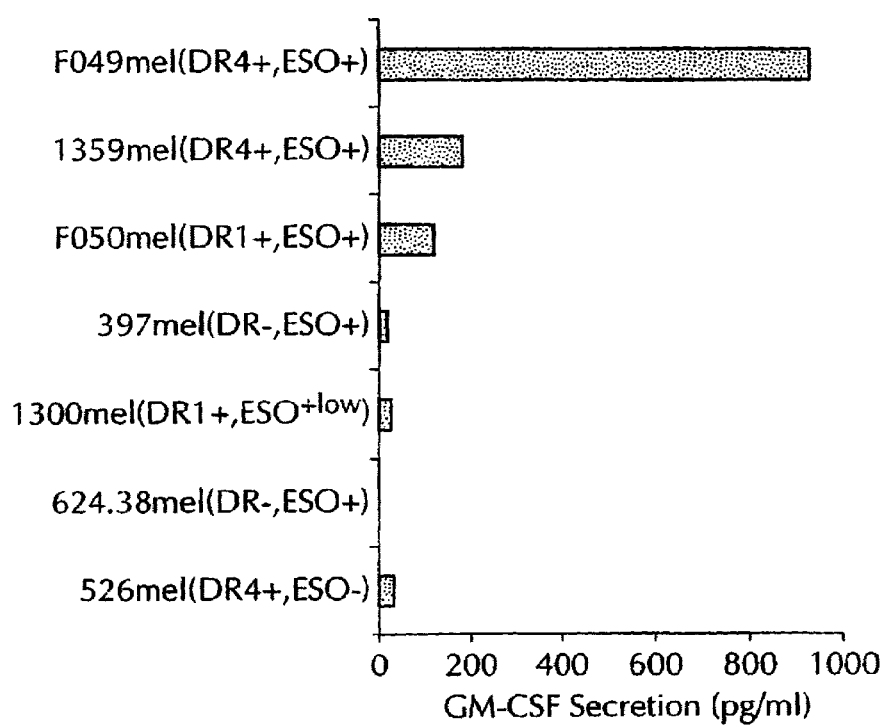
FIG. 5. Recognition of tumor cells by the CD4$^+$ T cell line TE4-1. All melanoma lines used as targets for TE4-1 were analyzed for the expression of HLA-DR4 and NY-ESO-1 by FACS and RT-PCR, respectively. TE4-1 was able to recognize NY-ESO-1$^+$ tumor lines constitutively expressing the HLA-DR4 molecule (1359mel and F049mel). F050mel expressing DR1 and NY-ESO-1 was also recognized by T cells. There was no reactivity against control targets 526mel (DR4 positive and NY-ESO-1 negative), 397mel, 624.38mel (DR negative and NY-ESO-1 positive), nor 1300mel (DR positive and NY-ESO-1 weakly positive).

Although peptide-specific $CD4^+$ and $CD8^+$ T cell activities can often be generated against a putative tumor antigen, in many cases tumor reactivity could not be demonstrated due to either the low affinity of the T cells or the failure of presentation of naturally processed peptides on the tumor cell surface (3). To test whether TE4-1 could recognize NY-ESO-1 epitopes naturally processed and presented by tumor cells, several melanoma lines were used as targets. The expression of NY-ESO-1 in each line was determined by RT-PCR, while the expression of HLA-DR alleles was determined by FACS analysis (data not shown). As shown in FIG. 5, TE4-1 was capable of recognizing NY-ESO-1/HLA-DR4 positive tumors (1359mel and F049mel), but failed to recognize tumor cell lines 397mel and 624.38mel (NY-ESO-1+/HLA-DR−), nor 526mel (NY-ESO-1−/HLA-DR4+). Interestingly, TE4-1 also recognized F050mel (DR1+/NY-ESO-1+), but did not recognize 1300mel expressing DR1 and a low level of NY-ESO-1. One possible explanation is that $CD4^+$ T cells may recognize the same peptide presented by different DR molecules. The recognition of F049mel could be specifically blocked in the presence of anti-HLA-DR antibody, but not the anti-MHC-class I antibody (data not shown). These studies suggested that the TE4-1 cell line recognized a naturally processed peptide on the tumor cell surface.

EXAMPLE 6

Characterization of the NY-ESO-1 Epitope Recognized by TE4-1

Since the two reactive peptides shared 15 amino acids (LPVPGVLLKBFTVSG) (SEQ ID NO: 10), the minimal length of peptide was determined by testing a series of N- and C-terminal truncated peptides. Peptides were pulsed onto $DR4^+$ 1088 EBV B cells and tested for their ability to stimulate TE4-1 cells. The Valine residue at position 128 was found to be critical for T cell recognition (FIG. 6A). The peptides with the N-terminal deletions up to Leucine residue at position 123 did not affect T cell recognition, but the peptide with further deletions partially lost its ability to stimulate T cells. The Leucine residue at position 123 may be a P1 anchor residue since the P1, P4, P6 and P7 residues contributed to the peptide binding to MHC class II molecules. Further deletions are required to determine the critical residues for binding to MHC class II molecules.

Based on the deletion experiments, we used a short version of peptide ESO p119-130 to determine the binding affinity of the peptide recognized by TE4-1. Peptides were pulsed onto 1088EBV B cells (HLA-DR4+) as targets at different peptide concentrations. As shown in FIG. 5B, no or little T cell activity was observed at 33 nM or lower concentrations of the ESO p119-130 peptide; high activities were detected at 0.33 M peptide concentration and the T cell activity did not reached a plateau at a 33 M peptide concentration. The control peptide was not recognized by TE41 even at a 33 M peptide concentration.

EXAMPLE 7

Figure 7B:
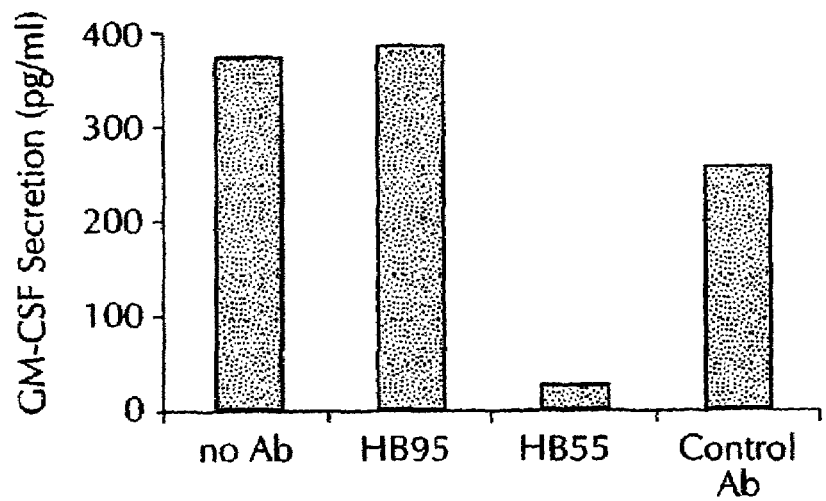

We have shown that T4-1 $CD4^+$ T cell line recognize ESO p116-135 in the context of DR4 and maybe DR1 as well. Here it is shown that TE4-1 can recognize not only the peptide but also the protein in the context of HLA-DR1. The recognition is blocked by anti-DR antibodies FIGS. 7A and 7B). This result shows evidence that ESO p116-135 may be a promiscuous peptide and can bind to DR4 as well as DR1. Thus, the applicable population of this peptide vaccine is quite large.

EXAMPLE 8

Materials and Methods for HLA-DP Studies

Cell Lines, Tissue Culture Reagents, and Antibodies Used in the Study

293CIITA is a cell line generated by transduction of 293 cells with a retrovirus encoding the MHC class II transactivator (53) (The retroviral plasmid is a courtesy of Dr. George Blanc at the University of South Florida, Tampa, Fla.). All is melanoma lines and EBVB lines were generated and maintained in RPMI 1640 (Life Technologies, Rockville, Md.) supplemented with 10% fetal calf serum (Biofluid, Inc., Gaithersburg, Md.). Culture medium for lymphocytes was RPMI 1640 with 0.05 mM beta-mercaptoethanol, 50 CU/ml IL-2 plus 10% human male AB serum provided by Valley Biochemicals Inc. (Winchester, Va.). Antibodies used in blocking assays were obtained from the following sources: W6/32 (HLA class I) and L243 (HLA DR) were hybridoma supernatant purified by Loftstrand Labs Lt. (Gaithersburg, Md.); Antibody clones IVA12 (HLA class II), B7/21 (HLA DP), Genox 3.53, and IVD12 (both HLA DQ) were purchased from Beckton Dickinson Immunocytometry Systems (San Jose, Calif.).

Construction of Plasmids

The pESO plasmid was an expression vector containing the NY-ESO-1 cDNA driven by a CMV promoter as described before (45). The pIi-ESO plasmid was constructed by inserting an NheI and NotI-digested PCR product of the whole NY-ESO-1 cDNA into the pTi80 vector digested with the same enzymes (54). The NY-ESO-1 cDNA was fused in frame with the first 80 amino acid residues of invariant chain (Ii) leader sequence at its N terminus. PCR primers used to amplify NY-ESO-1 were as follows: forward primer 5' cattgctagcATG CAG GCC GAA GGC CGG GGC A3' (SEQ. ID NO. 73) containing an NheI site and the reverse primer 5' aaggctacattGC GGC CGC TTA GCG CCT CTG CCC TGA G3' (SEQ. ID NO. 74) containing an NotI site.

Peptides and Generation of $CD4^+$ T Cells

Synthetic peptides used in this study were made using a solid phase method on a peptide synthesizer (Gilson Co. Inc., Worthington, Ohio) at the Surgery Branch, National Cancer Institute, Bethesda, Md. After deprotecting, the purity of each peptide was evaluated by mass spectrometry (Bio-synthesis, Inc., Lewisville, Tex.). Synthetic peptides were lyophilized and reconstituted in DMSO at 20 mg/ml and diluted to the indicated concentrations.

The in vitro sensitization procedure was carried out as previously described (50). Briefly, approximately $2.5 \times 10^5$ PBMC were plated in a 96-well flat-bottom plate in the presence of 20 micro g/ml peptide. On days 7 and 14, $1 \times 10^5$ non-irradiated PBMC were pulsed with 20 micro g/ml peptide, washed twice, and added to each well, and IL-2 at 20 CU/ml was added on day 8, day 11, day 15, and day 18. On day 21, cells were harvested and incubated with target cells overnight before the supernatants were taken for cytokine release assays.

T cells from those wells with specific activities were pooled and expanded using the OKT-3 rapid expansion method (55). After expansion, $CD8^+$ T cells were depleted from cultures using magnetic beads selection (Dynal Inc, Lake Success, N.Y.); and the cell lines were subsequently analyzed for $CD4^+$ and $CD8^+$ expression by flow cytometry.

Cytokine Release Assays

To prepare protein or peptide pulsed targets, peptides were used at a final concentration of 20 micro g/mL and proteins were used at a final concentration of 10 micro mg/ml. Cells were washed in serum-free RPMI medium, pulsed at 37 C in the absence of serum for 4 hours, followed by 2x washes. Unless specified, approximately $3 \times 10^4$ target cells were incubated with the same number of T cells for at least 16 hours before a cytokine release assay was carried out. Cytokine secretion was measured using a GM-CSF ELISA it (R&D Systems, Minneapolis, Minn.). Quantitation of the levels of human IL-4, TNF-alfa, and TGF-beta was carried out using cytokine kits obtained from the R&D Systems; and an IFN-gamma ELISA kit was purchased from Endogen Inc (Woburn, Mass.). Assays were cared out according to the manufacturer's instruction.

Molecular Typing of HLA DP Molecules

Total RNA was obtained from EBVB cells, CD40 ligand-stimulated B cells, $CD4^+$ T cells, or MHC class II positive melanoma lines for typing. Total RNA was purified using an RNeasy kit (Qiagen, Germany), and between 100 ng and 1 micro g of RNA was used for oligo dT-primed first strand cDNA synthesis. One tenth of the cDNA product was used to carry out PCR amplification with the advantage PCR system from Clontech (Palo Alto, Calif.). The following primer pairs were used for HLA DP-A and DP BPCR DPA forward primer 5' ATG CGC CCT GAA GAC AGA ATG T 3' (SEQ. ID NO. 75), DPA reverse primer 5'TCA CAG GGT CCC CTG GGC CCG GGG GA3' (SEQ. ID NO. 76), DPB forward primer 5'ATG ATG GTT CTG CAG GTT TCT G3' (SEQ. ID NO. 77), and DPB reverse primer 5'TTA TGC AGA TCC TCG TTG AAC TTT C3' (SEQ. ED NO. 78). The PCR product was subsequently purified and sequenced using the identical primers that were used to carry out the PCR. A number of patients appeared to be homozygous for the highly prevalent HLA DPB1*0401 gene product, as a single sequence was obtained from the PCR product. In the case of heterozygous patients, the PCR product was first cloned into a pCR4 vector vitrogen, Carlsbad, Calif.) and sequenced using 5' and 3' primers complementary to the vector sequence. The final sequence was searched against the IMGT-HLA database to confirm HLA DP identity http://www3.ebi.ac.uk/Services/imgt/hla).

EXAMPLE 9

Generation of a $CD4^+$ T Cell Line TE4-2 Against NY-ESO-1

Figure 8A:
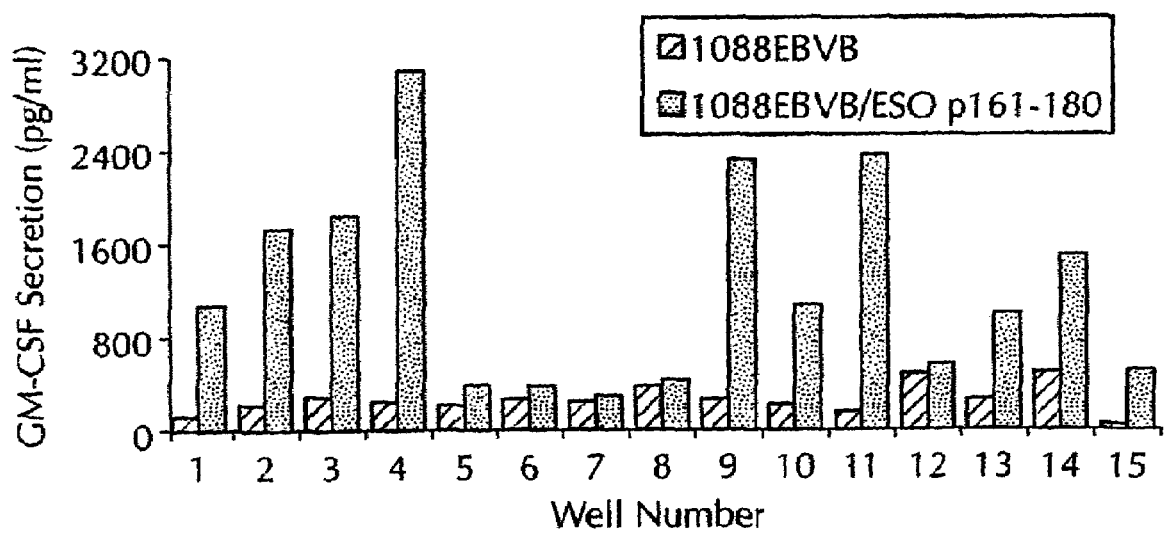
FIG. 8A-C. Generation of CD4$^+$ T cells from PBMC after in vitro stimulation with synthetic peptides.

Initial studies were carried out to identify NY-ESO-1 epitopes restricted by the HLA DR4 alleles. Eight 20-mer peptides which contained predicted 9-mer DR4 binding motifs were examined for recognition by lymphocytes from HLA-DR4-IE transgenic mice immunized with the NY-ESO-1 recombinant protein and stimulated int vitro (50). Three 20-mer peptides were found to be positive in these experiments. One of them was characterized as a promiscuous epitope of both DRB1*0401 and DRB1*0101(50). To further characterize two other peptides, ESO p161-180 and ESO p141-160, we used them to stimulate PBMC from a DRB1*0401 patient (TE) who had high titer antibodies as well as $CD4^+$ and $CD8^+$ T cells against NY-ESO-1 (50). A total of 24 micro-culture wells were used for each peptide. After three rounds of weekly stimulation, 15 out of 24 wells showed marked growth from PBMC that were stimulated with ESO p161-180. Nine of the 15 growth positive wells tested showed specific cytokine release against peptide pulsed DRB1*0401-expressing 1088 EBVB cells (FIG. 8A). Specific $CD4^+$ T cells were also generated from the PBMC stimulated with ESO p141-160, but were not discussed in this study (data not shown).

T cells from cultures that specifically responded to the ESO p161-180 peptide stimulation were then combined and expanded using a protocol described previously (55). Following the depletion of $CD8^+$ T cells, this culture, designated TE4-2, contained greater than 95% $CD4^+$ T cells as assessed by FACS analysis (data not shown).

Analysis of the cytokine secretion profile of TE4-2 demonstrated that this T cell line secreted IFN-gamma, TNF-alfa, IL-4 and GM-CSF, but not TGF-beta in response to peptide pulsed targets (data not shown). Thus, both Th1 and Th2 types of $CD4^+$ T cells may be present in this cell line. Alternatively, cells with a Th0 phenotype may be present in this culture.

EXAMPLE 10

Recognition of NY-ESO-1 by TEA2 in the Context of HLA DPB1*0401-0402

Figure 8B:
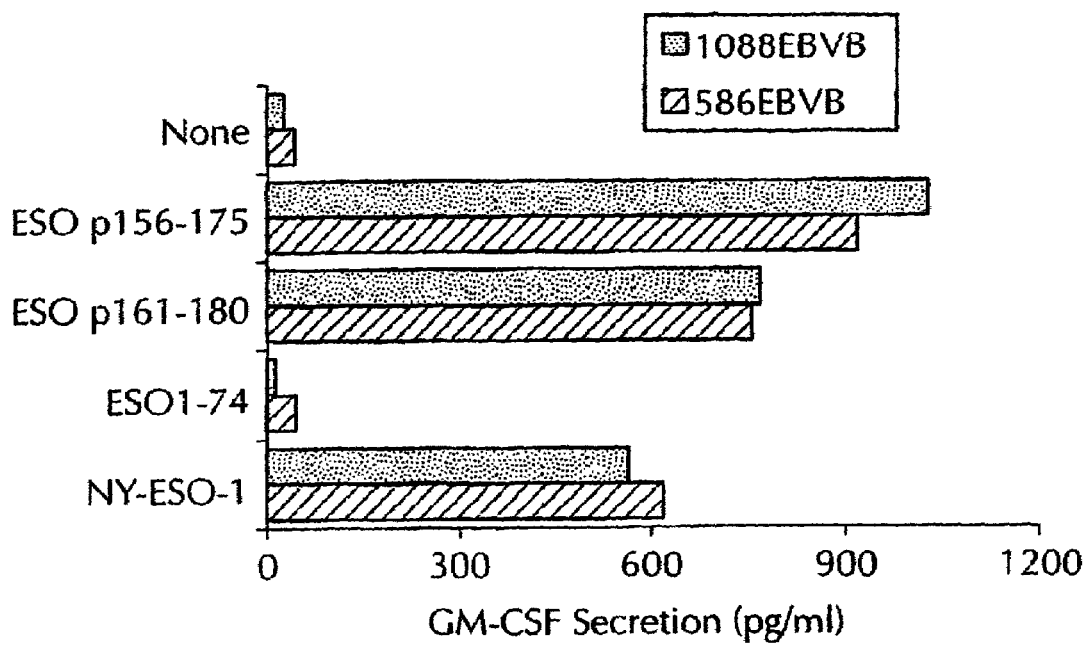

TE4-2 T cells was examined to respond to DR4 expressing target cells pulsed with ESO p161-180, an overlapping peptide, ESO p156-175, as well as the full-length NY-ESO-1 protein, respectively. 586 EBVB cells, which expressed DR1 but not DR4, were also used as APC. An irrelevant peptide, ESO p91-110, and a purified truncated recombinant protein, ESO1-74, comprising amino acid 1-74 (50) were used as controls. TE4-2 T cells specifically recognized a $DR^{++}$ 1088 EBVB line, when pulsed with the full-length NY-ESO-1 protein, but not the truncated ESO1-74 protein (FIG. 8B). Both the ESO p161-180 and p156-175 were recognized by TE4-2, indicating that the minimal peptide epitope resided between amino acid 161 and 175. In contrast, the initially predicted DR4-binding motif resided between amino acid 167 and 175. Unexpectedly, the TE4-2 T cell line appeared to respond equally well to peptides and proteins pulsed on 586 EBVB cells, which expressed DRB1*0101 but not DRB1*0401. This result suggested that either similar peptides were presented by multiple MHC class II restriction elements, or 1088 and 586 EBVB cell lines shared an MHC class II restriction element that presented the peptides to TE42 T cells. To test these possibilities, a number of other EBVB cells with known HLA DR and DQ types were also used as APC in an attempt to identify the restriction element utilized by TE4-2 T cells. All but one of the EBVB cell lines tested were able to present the ESO p161-180 peptide to TE4-2 (FIG. 5C).

Figure 9A:
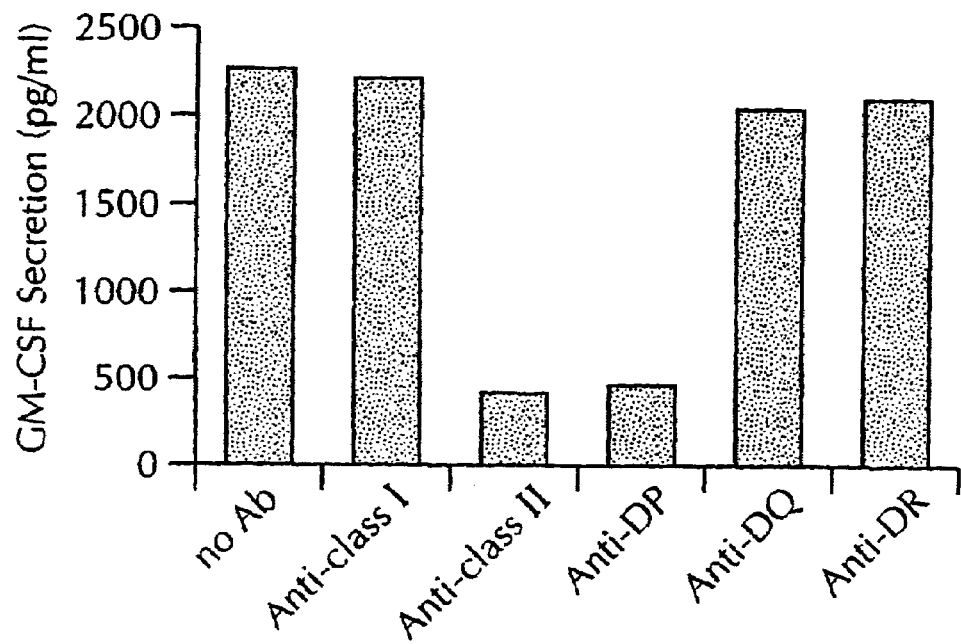
FIG. 9A-9C. Blocking of T cell recognition of NY-ESO-1 epitopes by an anti-DP antibody. 1088 EBVB cells pulsed with 20 micro g/ml ESO p161-180 peptide were used as target cells in the presence of different blocking antibodies. Specificity of antibodies used was as follows: anti-MHC class I (HLA A, B, C) antibody (W6/32), anti-MHC class II (HLA DP, DQ, DR) antibody (IVA12), anti-HLA DP antibody (B4/21), anti-HLA DR antibody (L243), and anti-HLA DQ antibodies (mixture of Genox 3.53 (anti-DQw1) and IVD12 (anti-DQw3)). All antibodies were used at a final concentration of 20 micro g/ml each.
Figure 9B:
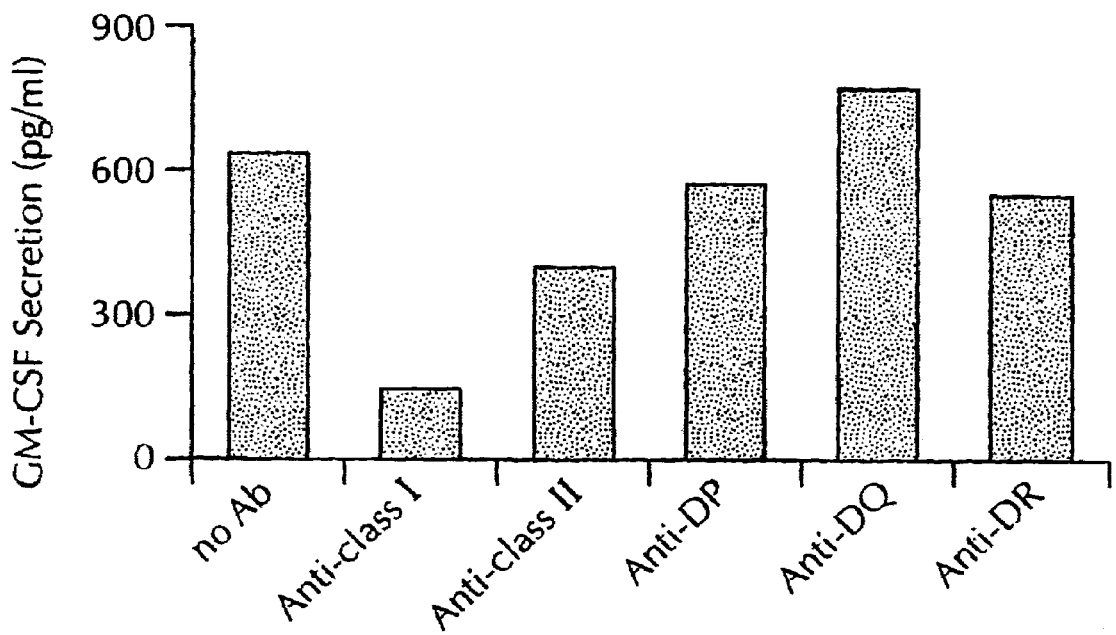
Figure 9C:
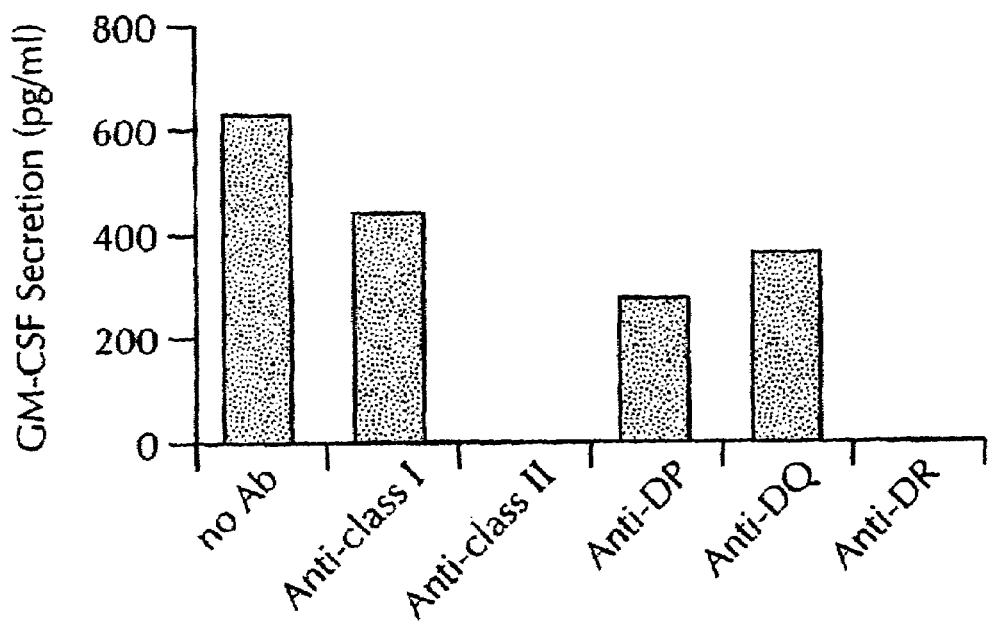

T cell recognition of peptides was then carried out in the presence of specific antibodies that blocked the recognition of peptides restricted by different MIC restriction elements. The results in FIG. 9A through 9C demonstrated that an antibody which blocked all MHC class II alleles (IVA12) and an antibody with a specificity for blocking all HLA DP alleles (B4/21), abolished the ability of TE4-2 T cells to recognize ESO p161-180. Antibodies directed against HLA-A, B, and C alleles (W6/32) as well as antibodies against the MHC class R DR (L243) and DQ (a mix of Genox 3.53 and IVD12) alleles, had little or no effect on the stimulation of TE4-2 T cells. Thus, these results suggested that the TE4-2 T cells recognized ESO p161-180 in the context of a highly prevalent HLA DP allele shared by EBVB cell lines used in this study.

Figure 8C:
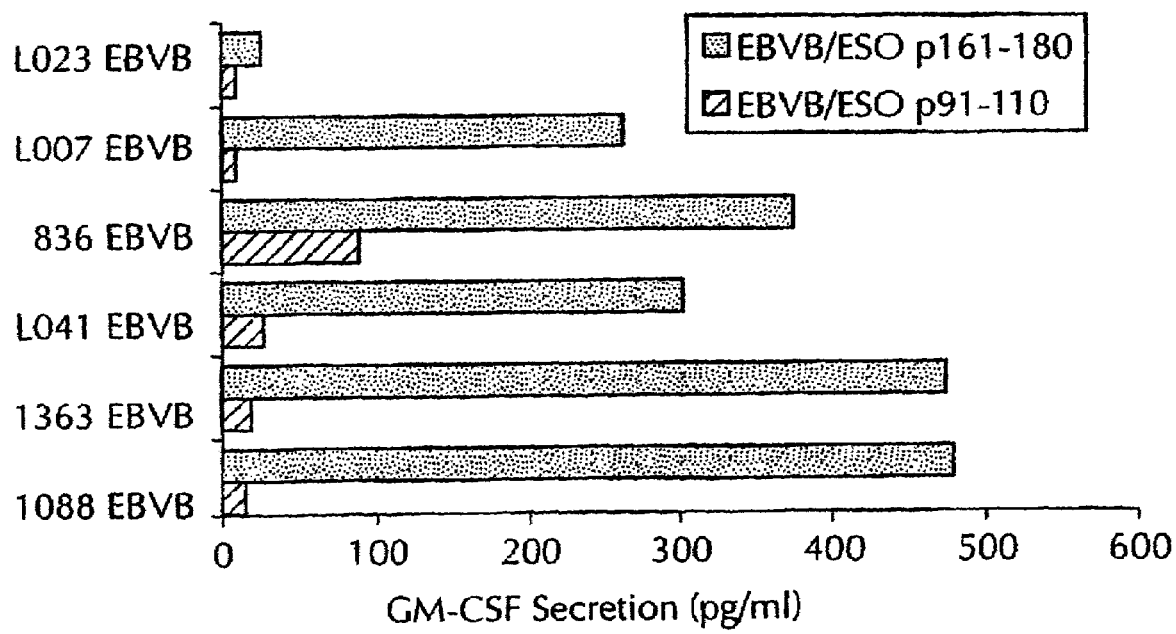

The HLA-DP alleles were then molecularly cloned and sequenced for cell lines used in FIG. 8C. These studies showed that 1088 and 586 EBVB lines were both homozygous for the HLA DPB1*0401 gene product, and patient TE expressed DPB1*0401 as well as an unknown DP allele (Table 2). L023 EBVB cell line, which did not present the ESO p161-180 peptide to TE4-2 was typed as homozygous for the HLA DP allele, which was distinct from DPB1*0401 and 0402. The 1363, 1088, 836, and L007 EBVB cell lines all expressed DPB1*0401, whereas L041 EBVB cell line expressed DPB1*0402, which was different from the DPB1*0401 molecule by two amino acid residues at position 84 and 85. Thus, it appeared that both the DPB1*0401 and DPB1*0402 were able to present the ESO p161-180 epitope to TE4-2 CD4⁺ T cells.

TABLE 2

HLA (DP, DQ, and DR alleles) typing of patients used in this study.

| | HLA-DP | HLA-DQ | HLA-DR | |
|---|---|---|---|---|
| Patients with NY-ESO-1 antibodies: | | | | |
| TE | B1*0401, nd | 0302, 06** | B1*0401, 1501; | B4*0101, B5*0101 |
| BE | B1*0401 | 0301, 0302 | B1*0401, 1102; | B3*0202, B4*01** |
| AC | B1*04 negative | 0603, 0604 | B1*1301, 1302; | B3*0202, B3*0301 |
| FJ | B1*0401 | 0502, 0601 | B1*1502, 1601; | B5*0102, B5*02** |
| LD | B1*0401 | 0303, 0603 | B1*0901, 1301; | B3*0101, B4*01** |
| CJ | B1*0401, nd | 0201, 0301 | B1*0701, 1101; | B3*0202, B4*01** |
| BFE | B1*0402, nd | 0303, 0602 | B1*0701, 1501; | B4*01**, B5*0101 |
| KF | B1*0401, 0402 | 0301, 0603 | B1*0401, 1301; | B3*0101, B4*0101 |
| CT | B1*0401, 0402 | 0301, 0603 | B1*1101, 1502; | B3*0202, B5*0102 |
| DA | B1*0401 | 06** | B1*08**, 15**; | nd |
| BL | BP*0401, nd | 0201, 0602 | B1*0301, 1501; | B3*0101, B3*0202 |
| Patients with NY-ESO-1 expressing tumor but no detectable Ab: | | | | |
| FS | B1*04 negative | 0301, 0501 | B1*0101, 1101; | B3*0202 |
| BFJ | B1*04 negative | 0201, 05** | B1*0701, 1601; | B3*0101, B3*0202 |
| MS | B1*04 negative | 0501 | B1*1501; | B5*0101 |
| EBVB lines used for antigen presentation: | | | | |
| L007 EBVB | B1*0401 | 0602 | B1*1501 | B5*0101 |
| L023 EBVB | B1*04 negative | 0301 | B1*1201 | B3*0202 |
| L041 EBVB | B1*0402, nd | 0402 | B1*0822 | nd |
| 836 EBVB | B1*0401, nd | 02** | B1*0701; | B4*01** |
| 1363 EBVB | B1*0401 | 0501 | B1*0101; | nd |
| 1088 EBVB | B1*0401 | 0201, 0301 | B1*0301,04**; | B3*0101,B4*01** |
| 586 EBVB | B1*0401 | 0501, 0201 | B1*0101,07**; | B4*01** |

"nd": not determined.
**: subtypes unknown.
The detection of the presence of NY-ESO-1 antibodies in melanoma patients was previously described (50).

To determine whether it required a specific DPA chain to present the epitope to TE42 T cells, the HLA DPA molecules in DPB1*0401-0402 expressing EBVB cells were also analyzed. DPB1*0401-0402 expressing EBVB cells as used in FIG. 8C had more than one type of HLA DPA molecule (data not shown); however, all were able to present the NY-ESO-1 epitope to TE4-2 T cells equally well.

EXAMPLE 11

Recognition of a Naturally Processed NY-ESO-1 Epitope on Tumor Cells by TE4-2

Figure 10A:
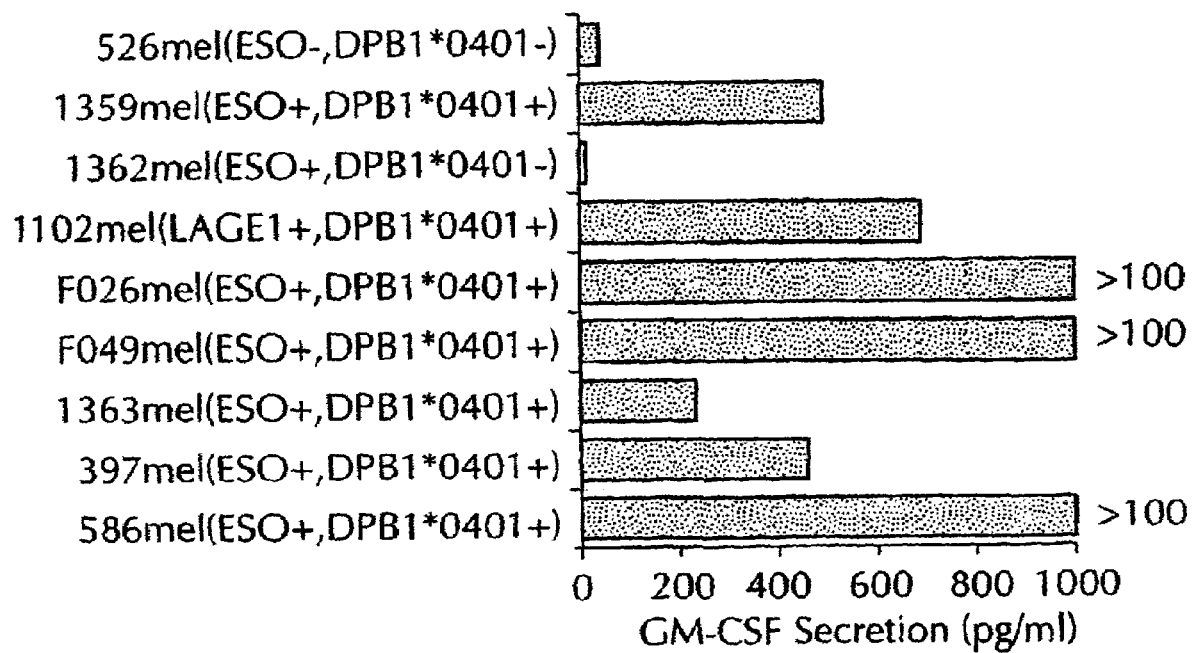
FIG. 10A-10B. Recognition of tumor cells and 293CIITA/NY-ESO-1 by TE4-2 CD4+ T cells.

To investigate whether the T cell epitope recognized by TE4-2 was naturally processed and presented on the surface of tumor cells, tumor lines that expressed NY-ESO-1 as well as DPB1*0401 were used as targets. TE4-2 T cells recognized multiple tumor lines expressing both NY-ESO-1 and DPB1*0401, but failed to recognize a tumor line that expressed NY-ESO-1, but did not express any of the HLA DPB1*0401 and 0402 alleles (1362mel) (FIG. 10A). In addition, TE4-2 T cells failed to recognize DPB1*0401 negative and NY-ESO-1 negative tumors (526met). One melanoma line, 1102mel, which expressed HLA DPB1*0401 but did not express NY-ESO-1, was also recognized by TE2 T cells. The results of RT-PCR analysis demonstrated that 1102mel expressed the LAGE-1 gene, a cancer/testis antigen possessing approximately 90% amino acid similarity to NY-ESO-1 (57). A sequence identical to ESO p161-175 was also present in the LAGE-1 protein. These results suggested that epitopes recognized by TE4-2 were present on the surface of tumor cells, and that it is shared between NY-ESO-1 and the closely related tumor antigen LAGE-1.

Figure 10B:
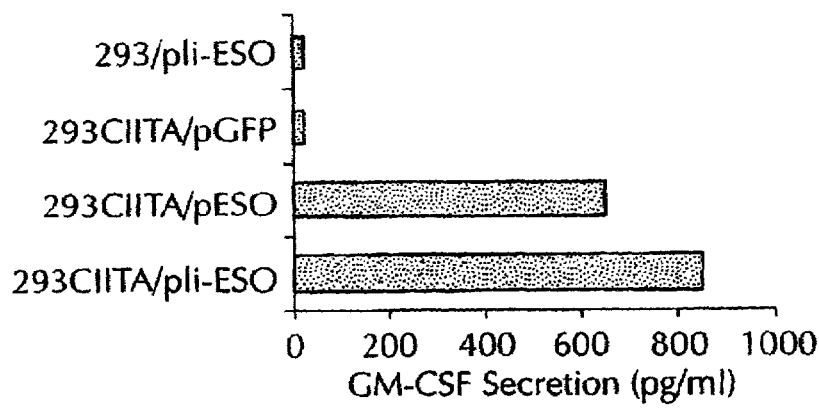

In addition to NY-ESO-1 expressing melanoma lines, TE4-2 T cells were also tested for recognition of NY-ESO-1 transfected 293CIITA cells. 293CIITA cell line was generated by transducing 293 cells with a retrovirus expressing the MHC class II transactivator gene (CIITA) (53). The 293CIITA cells but not the parental 293 cells expressed homozygous HLA DPB1*0401 molecule as determined by RT-PCR (data not shown). TE4-2 T cells reacted specifically with NY-ESO-1 transfected 293CIITA cells (FIG. 10B). In contrast, TE4-2 T cells failed to recognize either 293CIITA cells transfected with the pGFP plasmid or parental 293 cells transfected with Ii-NY-ESO-1. An Ii targeting sequence was not required for the processing and recognition of NY-ESo-1, but slightly enhanced T cell recognition (FIG. 10B). These results further demonstrated that TE4-2 T cells recognized a naturally processed NY-ESO-1 epitope.

EXAMPLE 12

HLA DP4-Restricted Epitopes Overlapping with an HLA-A2 Restricted Epitope

Target cells pulsed with the two overlapping peptides, ESO p161-180 and p156-175 were recognized equally well by TE4-2 T cells, indicating that the minimal T cell epitope was located in the region ranging from amino acids 161 to to 175 (FIG. 8B).

Figure 11A:
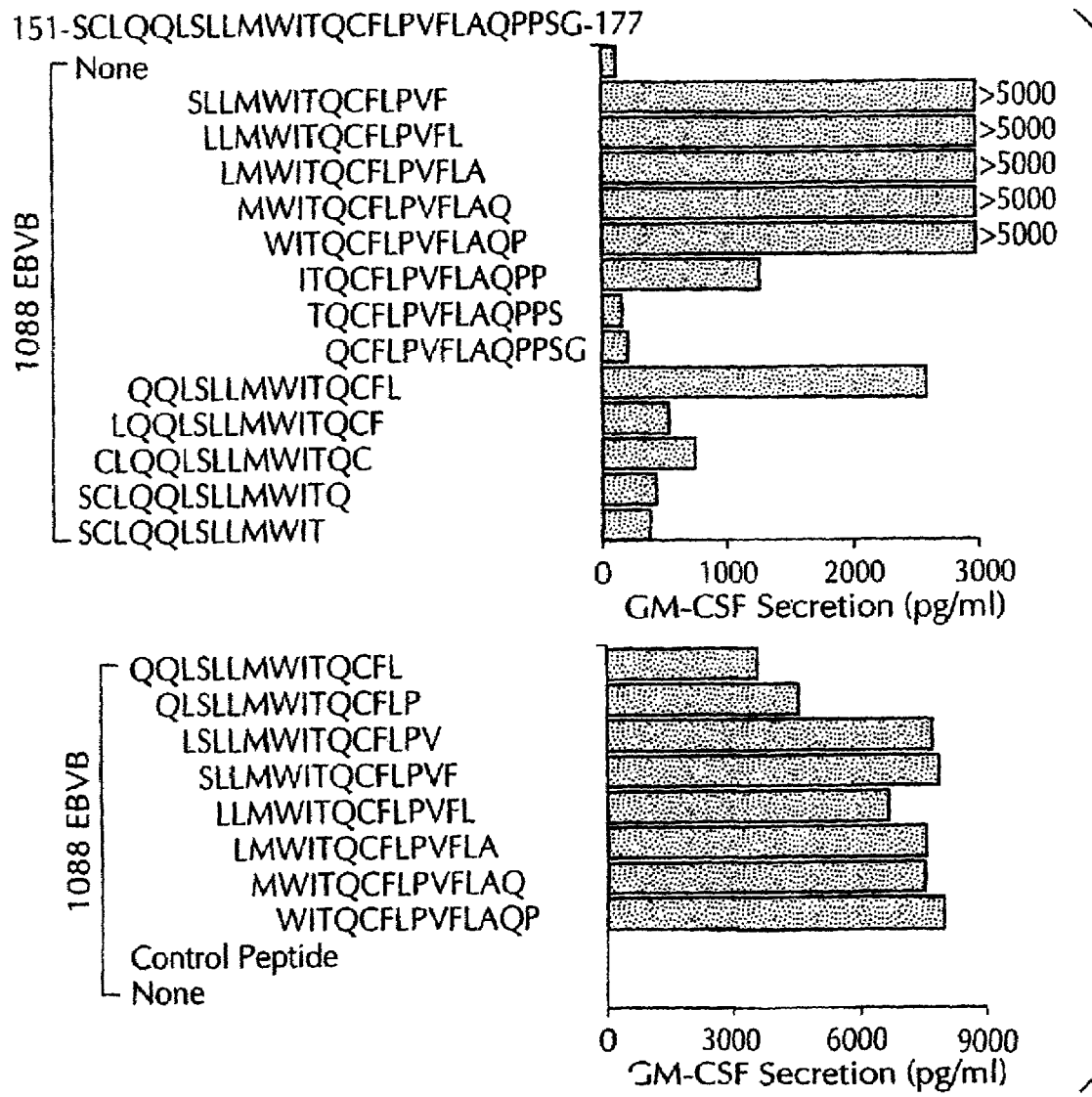

In an attempt to identify the anchor residues present between amino acid 161 and 175, a series of overlapping 13 mer peptides were used to pulse 1088 EBVB cells and tested for their abilities to stimulate TE4-2 T cells. As shown in FIG. 11A, a partial loss of activity was observed when the W residue at position 161 was removed; and a complete loss of activity was observed when the I residue at position 162 was removed. The deletion of a C-terminal L residue at position 167 also abolished the recognition of the peptide by TE4-2 T cells. Moreover, the residue V at position 169 also appeared to be important, as deletion of this residue resulted in a two-fold decrease in the peptide's stimulatory activity. Thew results indicated that the W residue at position 161 may be a P1 anchor, and the L residue at position 167 represented the P7 anchor. The V residue at position 169 also appeared to contribute to the stimulatory capacity of the peptide epitope, indicating that it may represent the P9 anchor residue. These putative anchor residues closely matched the previously described consensus HLA DPB1*0401 binding motif (57).

The ESO p157-170 peptide, which contained all three anchor residues, was used in the titration experiment to determine the minimal stimulatory concentration for the peptide. The results demonstrated that ESO p157-170 was able to stimulate significant cytokine releases from TE4-2 T cells at a minimum concentration between 3 and 33 nM (FIG. 11B). These results indicated that TE4-2 T cells recognized ESO p157-170 with a high affinity. This apparent affinity is superior to most known MHC class II binding epitopes from non-mutated peptides, such as those from gp100 (58), tyrosinase (59), and CDC-27 (54). Other peptides spanning the same region such as the ESO p161-180 and p156-175 also had similar minimal stimulatory concentrations for TE4-2 T cells (data not shown).

Interestingly, a previously identified HLA-A2 epitope, ESO p157-167 (47) was contained within the DPB1*0401-0402 epitope, ESO p157-170. To assess whether the HLA-DP epitope may be presented by HLA-A2 and cross-react with CD8$^+$ T cells, ESO p157-170 was tested for recognition by TE8-1, a CD8$^+$ T cell line specifically recognizing the HLA-A epitope ESO p157-167. ESO p157-170 was able to simulate significant cytokine releases from TE8-1 T cells when pulsed onto L023 EBVB cells, which expressed HLA-A2 but not the DPB1*0401-0402 allele (FIG. 11C). This experiment demonstrated that the ESO p157-170 epitope had dual MHC class I and class II specificity and could stimulate both CD4$^+$ and CD8$^+$ T cells recognizing the NY-ESO-1 protein. Therefore, ESO p157-170 might be a attractive candidate for cancer vaccines aimed at eliciting both CD4$^+$ and CD8$^+$ T cells specifically recognizing tumor cells.

EXAMPLE 13

Association of the NY-ESO-1 Antibody Production with HLA DPB1*0401-0402

HLA DPB1*0401-0402 is a dominant MHC class II allele present in a large portion of Caucasians, ranging between 43% and 70% in population studies involving different ethnic groups (52). Previous studies (48, 50) have shown that normal donors as well as cancer patients without NY-ESO-1 expressing tumors do not develop antibodies against NY-ESO-1. In contrast, 50% of patients with NY-ESO-1 expressing tumor developed NY-ESO-1 specific Ab. In a panel of 88 melanoma patients whose serum samples were tested, 11 patients were found to have high titers of NY-ESO-1 antibodies (50). The previously identified DR4-restricted CD4$^+$ T cell peptides cannot account for the production of NY-ESO-1 specific Ab since many patients did not express DR4 alleles at all (Table 2). To further investigate whether NY-ESO-1 specific DP4-restricted CD4$^+$ T cells were associated with the production of NY-ESO-1 specific Ab in these melanoma patients, we first analyzed their HLA DP subtypes. Ten out of the 11 patients with NY-ESO-1 antibodies expressed DPB1*0401 and/or 0402, whereas no dominant DQ or DR restriction elements could be identified in this group of patients (Table 2). Three patients from this panel with known NY-ESO-1 expressing tumors but with no detectable antibodies did not express the DPB1*0401-0402 alleles. Since tumor cell lines from the remaining 74 patients were not available to assess the NY-ESO-1 expression from these patients, further studies were not carried out to identify their HLA DP types. A p-value of 0.011 was obtained from a Fisher's exact test, indicating the significance of the association between antibody responses and the HLA-DPB1*0401-0402 expression. Since NY-ESO-1 is expressed in 25-30% of tumor cell lines and DP4 is expressed in 43-70% of the population, the percentage of patients expressing both NY-ESO-1 and DP4 and with the potential to develop antibody responses is in the range of 10-21%. This hypothetical prediction is very close to the observed 10-13% frequency of patients with NY-ESO-1 antibodies.

In order to obtain additional evidence as to the association between NY-ESO-1 antibody responses and the DPB1*0401-0402 expression, PBMC from 6 of the 11 patients with NY-ESO-1 antibodies were used for in vitro stimulation with the ESO p161-180 peptide. In vitro sensitization was also carried out with PBMC from two DPB1*0401+patients with no detectable NY-ESO-1 antibodies. T cells were examined for their response to 293CIITA cells pulsed with the ESO p161-180 peptide after two or three rounds of in vitro stimulation. T cells from 5 out of the 6 patients (including TE) with NY-ESO-1 antibodies showed a specific recognition of the ESO p161-180 epitope presented by 293CIITA cells (DP4$^+$ and HLA-A2) (Table 3). Multiple wells from patient CT and BL appeared to react with peptide pulsed targets. Sensitized PBMC from these two patients also showed significant tumor recognition of DPB1*0401+ and NY-ESO-1+ melanoma lines without further enrichment of the CD4+ T cells (data not shown). In contrast, NY-ESO-1 reactive T cells were not generated using PBMC from two patients (WC and EW) with no detectable NY-ESO-1 antibodies after three stimulations. These results suggested that patients who developed anti-NY-ESO-1 antibodies also contained relatively high precursor frequency of T cells reactive with the DPB1*0401-restricted epitope. These NY-ESO-1 specific CD4+ T cells may have contributed to the development of antibody responses against the NY-ESO-1 cancer/testis antigen.

TABLE 3

Recognition of DPB1*0401-restricted ESO p161-180 by CD4+T cells generated from patients with and without specific antibody responses.

| Patients | T Cell Reactivity (pg/ml IFN-gamma secretion) | | Antibody Responses | DPB1*04 01 |
|---|---|---|---|---|
| | Irrelevant peptide@ | ESO p161-180 | | |
| BE | 0 | 0 | + | + |
| FJ | 0 | 160 | + | + |
| CJ | 150 | 475 | + | + |
| CT | 150 | 2350 | + | + |
| BL | 180 | 1089 | + | + |
| TE | 90 | 207 | + | + |
| WC% | 0 | 0 | − | + |
| EW% | 0 | 0 | − | + |

@293CIITA cells (DPB1*0401 positive and HLA-A2 negative) were pulsed with the indicated peptides and used as targets. Cultures showing more than 100 pg/ml IFN-production in response to ESO p161-180 pulsed targets and at least two-fold above the background were defined as positive. Values of cytokine secretion were from representative positive wells.
%Anti-NY-ESO-1 antibody titers as well as the HLA DP types of patients WC and EW were determined in this study (data not shown). Expression of NY-ESO-1 in tumors from these two patients was not known since their tumor specimens were not available.

EXAMPLE 14

Modifications were made to one of the wild type HLA DP4 peptides. The modification was designed to make the peptide more soluble so that it could be purified to more than 90% homogeneity, which is required by FDA for peptide clinical trials. The wild type as well as the modified peptides are as follows:

```
                                  (SEQ ID NO: 54)
    Wild type ESOp157-170;       SLLMWITQCFLPVF;

(SEQ ID NO: 79)
    Wild type ESOp157-167;       SLLMWITQCFL;

(SEQ ID NO: 63)
    ESOp156R-169;                RSLLMWITQCFLPV;
    and (SEQ ID NO: 64)
    ESOp157-170R;                SLLMWITQCFLPVR.
```

Figure 12A:
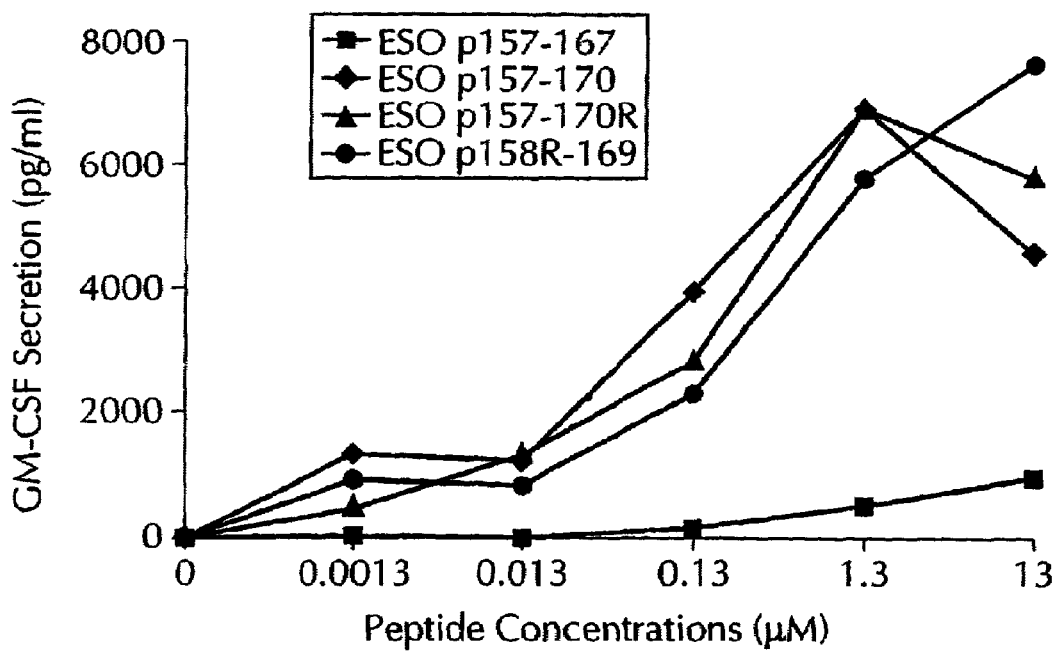
FIGS. 12A and 12B. Titration of peptides for recognition by TE4-2 CD4+ T cells and TE8-1 CD8+ T cells.
Figure 12B:
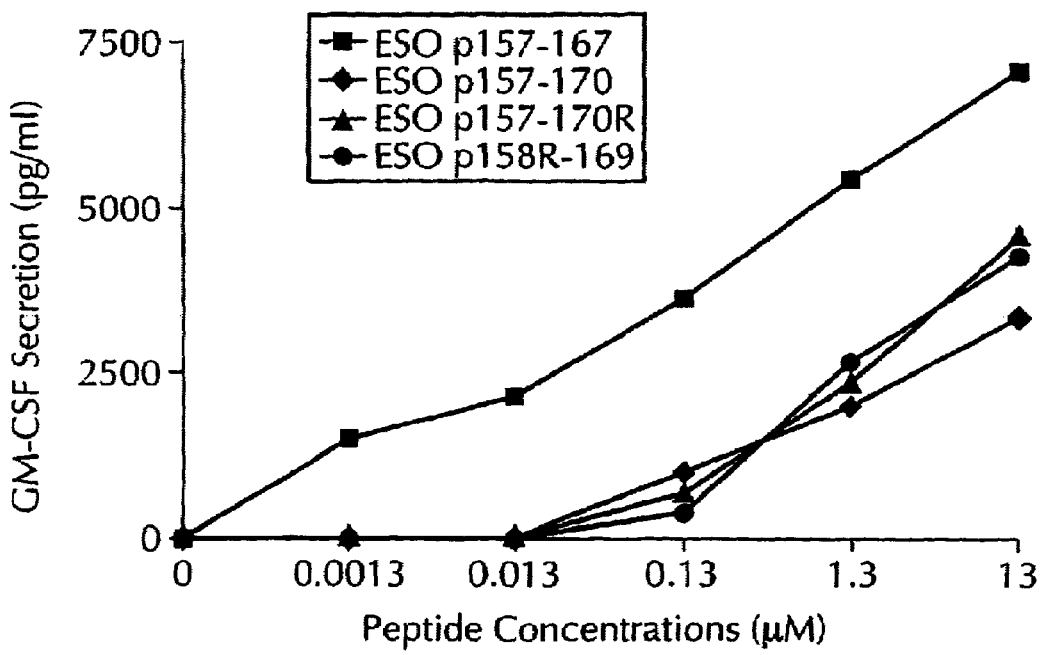

Experiments were carried out to test whether these modified peptides were equality well recognized by T cells. Since ESO p157-170 showed dual HLA-A2 and HLA-DP4 binding specifications, the recognition in both DP4 (FIG. 12A) and A2 (FIG. 12B) restricted fashion by TE4-2 CD4+ T cells and TE8-1 CD8+ T cells, respectively was determined.

Results indicated that these modified peptides were equally well recognized as the wild type by CD4+ T cells as well as CD8+ T cells.

EXAMPLE 15

NY-ESO-1 Epitope Specific CD4+ T Lymphocytes Immunotherapy

T-lymphocytes presensitized to a melanoma antigen may be effective in therapeutically treating mammals afflicted with a melanoma. T-lymphocytes are isolated from peripheral blood or melanoma tumor suspensions and cultured in vitro (Kawakami, Y. et al, 1988, *J. Exp. Med.* 168: 2183-2191).

The T lymphocytes are exposed to the epitope VLLKEFTVSG (SEQ ID NO: 19) or the epitope WITQCFLPVF (SEQ ID NO: 80) at a concentration of 1 μg/ml alone or in the presence of IL-2, resensitized and expanded in culture. CD4+ T-lymphocytes exposed to the epitope are administered to a mammal at about $10^9$ to $10^{12}$ lymphocytes per mammal. The lymphocytes are administered either intravenously, intraperitoneally or intralesionally. The treatment may be administered concurrently with other therapeutic treatments such as cytokines, surgical excision of melanoma lesions and chemotherapeutic drags. NY-ESO-1 specific CD8+ T lymphocytes may be administered concurrently with CD4+ T lymphocytes.

EXAMPLE 16

Treatment of Patients with Metastatic Melanoma

In this protocol, patients with advanced melanoma are immunized with an antigenic cancer epitope.

Patients eligible for the trial must have evidence of measurable or evaluable metastatic melanoma that has failed standard effective therapy. Patients must have tumors that express the NY-ESO-1 antigen as evidenced by PCR or Northern Blot analysis of tumor cell RNA.

Patients receive either 1 ng, 1 μg, 1 mg or 500 mg/kg body weight of a MHC class II restricted T cell epitope via intravenously at day zero) day 7 and day 14 alone or in combination with IL2 and/or an immunostimulatory molecule. Patients are evaluated for toxicity, immunologic effects and therapeutic efficacy. Patients may additionally receive an NY-ESO-1 class I restricted T cell epitope.

Lymphocytes taken from the treated patients are tested for specific response to the NY-ESO-1 cancer antigen or MHC class II restricted T cell epitope.

A complete response is defined as the disappearance of all clinical evidence of disease that lasts at least four weeks. A partial response is a 50% or greater decrease in the sum of the products of the perpendicular diameter of all measurable lesions for at least four weeks with no appearance of new lesions or increase in any lesions. Minor responses are defined as 25-49% decrease in the sum of the products of the perpendicular diameters of all measurable lesions with no appearance of new lesions and no increase in any lesions. Any patient with less than a partial response is considered a non-responder. The appearance of new lesions or greater than 25% increase in the product of perpendicular diameters of prior lesions following a partial or complete response is considered as a relapse.

Discussion

NY-ESO-1 is an important immune target because it gives rise to both humoral and cellular immune responses (19-21).

Although its expression pattern is similar to antigens in the MAGE gene family, NY-ESO-1 is more frequently expressed in breast, prostate and lung cancers than any member of the MAGE family (19, 20, 23). More interestingly, high titered NY-ESO-1 reactive antibodies were frequently detected in patients with cancer (FIGS. 2B and 2C) while a very low percentage of patients developed high titers of antibodies against the MAGE antigens or differentiation antigens such as tyrosinase, gp100, TRP-1 and TRP-2 (data not shown and (22). These studies strongly suggest that NY-ESO-1 reactive CD4$^+$ T cells may be involved in antibody production and CTL proliferation. In this study, we identified the HLA-DR4-restricted T cell epitope derived from NY-ESO-1 by the use of HLA-DR4-transgenic mice and in vitro stimulation of human PBMC with candidate peptides. To our knowledge, this is the first demonstration that T cell epitopes from NY-ESO-1 were shown to be presented by MHC class II molecules to CD4$^+$ T cells. Since NY-ESO-1-specific antibodies and CTL were detected in patients with different HLA genotypes, other CD4$^+$ T cell epitopes presented by HLA class II molecules other than HLA-DR4 were identified in the present invention.

Recently, two groups reported the identification of MHC class II-restricted T cell epitopes from the known MHC class I-restricted tumor antigen, MAGE-3. CD4$^+$ T cell clones generated from PBMC stimulated with DC pulsed with purified MAGE-3 protein recognized peptide or protein pulsed on HLA-DR13-matched EBV B cells, but not MAGE-3$^+$/DR13$^+$ tumor cells (14). However, in another study, CD4$^+$ T cells generated from PMBC stimulated with peptides predicted by a computer-assisted algorithm were capable of recognizing both peptide pulsed on EBV B cells and MAGE-3$^+$/DR11$^+$ tumor cells (15). In the case of NY-ESO-1, we here show that CD4$^+$ T cells can recognize the NY-ESO-1 protein or peptide pulsed on DR4 matched EBV B cells as well as tumor cells expressing NY-ESO-1 (FIGS. 4 and 5). Utilization of HLA-DR transgenic mice may have advantages in identifying putative peptides since immunized transgenic mice presumably have a high precursor frequency of specifically reactive T cells. Once candidate peptides were identified, CD4$^+$ T cells could be generated from PBMC stimulated with synthetic candidate peptides. Therefore, the combined use of transgenic mice immunized with the whole protein and stimulated with the peptides predicted by a computer-assisted algorithm may avoid the need to stimulate human PBMC with a large number of peptides and several rounds of in vitro stimulation. Furthermore, candidate peptides identified by using the immunized transgenic mice are likely to be peptides that are naturally processed and presented on the cell surface. This may increase the likelihood that peptide-specific CD4$^+$ T cells can recognize tumor cells as well. Finally, the use of PBMC from a patient (TE), who developed a high titer of antibody and a high precursor frequency of CTL against NY-ESO-1, may make it easier to generate tumor-specific CD4$^+$ T cells since both antibody production and CTL require the help of CD4$^+$ T cells. This approach has been used to identify a number of MHC class II-restricted T cell epitopes from known autoantigens involved in autoimmune diseases (28). Therefore, the strategy used in this study may be applicable to many other known MHC class I-restricted tumor antigens while other strategies such as a direct gene cloning approach may facilitate the identification of unknown MHC class II-restricted tumor antigens.

Clinical trials using peptides derived from tissue-specific differentiation antigens such as gp100 showed some evidence of therapeutic efficacy in the treatment of patients with melanoma (4). Although no significant toxic side effects were observed in the patients treated with the modified gp100 peptides, vitiligo or depigmentation was often found in patients who responded to therapy (29), suggesting that anti-tumor immunity induced by immunization with self-antigens may cause autoimmunity. In animal studies using TRP-1 as an immune target, similar results (antitumor immunity and coat depigmentation) were also obtained (30-32). Interestingly, antitumor immunity and autoimmunity mediated by gp75/TRP-1 appeared to involve CD4$^+$ T cells and antibodies (33). Immunization of mice with hTRP-2 (34), but not mTRP-2 (35), broke tolerance to the self-antigen and the antitumor immunity required the particular of both CD4$^+$ and CD8$^+$ T cells (33). These studies suggested that antitumor immunity could be mediated by either antibodies or CD8$^+$ T cells, but both require the critical help of CD4$^+$ T cells (24, 33).

The MHC class II-restricted NY-ESO-1 peptides identified in this study may be useful in clinical applications since CTL and antibodies against NY-ESO-1 were detected in patients with cancer. Immunization with both MHC class I and II-restricted peptides or with a purified NY-ESO-1 protein may induce NY-ESO-1 specific CD4$^+$, CD8$^+$ T cells as well as antibodies. Alternatively, patients could be immunized with dendritic cells loaded with both class I and II peptides or infected with recombinant viruses encoding the NY-ESO-1 gene. Because testicular germ cells do not express MHC class I and II molecules (36), immune responses against NY-ESO-1 should be specific for tumor cells, and thus generate little or no autoimmune responses. Similar studies using MHC class I-restricted peptides of MAGE-3 or peptides pulsed on dendritic cells indicated that while antitumor immunity (CTL responses) and slow tumor regression was demonstrated, no depigmentation/vitiligo or other significant side effects were observed (6, 7). Antitumor immunity may be enhanced by providing tumor-specific CD4$^+$ T cell help.

REFERENCES

1. Houghton A N. (1994) Commentary: Cancer antigens: Immune recognition of self and alterted self. *J. Exp. Med.* 180: 14.
2. Wang R-F. (1997) tumor antigens discovery: perspectives for cancer therapy. *Mol. Med.* 3: 716-31.
3. Wang R-F, Rosenberg S A. (1999) Human tumor antigens for cancer vaccine development. *Immunological Reviews* 170: 85-100.
4. Rosenberg S A, Yang J C, Schwartzentruber D J, et al. (1998) Immunologic and therapeutic evaluation of a synthetic tumor-associated peptide vaccine for the treatment of patients with metastatic melanoma. *Nat. Med.* 4: 321-327.
5. Nestle F O, Alijagic S, Gilliet M, et al. (1998) Vaccination of melanoma patients with peptide- or tumor lysate-pulsed dendritic cells. *Nat. Med.* 4: 328-32.
6. Marchand M, van Baren N, Weynants P, et al. (1999) Tumor regressions observed in patients with metastatic melanoma treated with an antigenic peptide encoded by gene MAGE-3 and presented by HLA-A1. *Int. J. Cancer* 80: 219-30.
7. Thurner B, Haendle R, Dieckanann P, et al. (1999) Vaccination with Mage-3A1 peptide pulsed mature, monocyte-derived dendritic cells expands specific cytotoxic T cells and induces regression of some metastases in advanced stage IV melanoma. *J. Exp. Med.* 190: 1669-1678.
8. Hung K, Hayashi R, Lafond-Walker A, Lowenstein C, Pardoll D, Levitsky H. (1998) The Central Role of CD4(+) T Cells in the Antitumor Immune Response. *J. Exp. Med.* 188: 2357-2368.

9. Toes R E, Ossendorp F, Offringa R, Melief C J. (1999) CD4 T Cells and their role in antitumor immune responses. *J. Exp. Med.* 189: 753-756.

10. Ossendorp F, Mengede E, Camps M, Filius R, Melief C J. (1998) Specific T helper cell requirement for optimal induction of cytotoxic T lymphocytes against major histocompatibility complex class II negative tumors. *J. Exp. Med.* 187: 693-702.

11. Mumberg D, Monach P A, Wanderling S, et al. (1999) CD4(+) T cells eliminate MHC class II-negative cancer cells in vivo by indirect effects of IFN-gamma. *Proc. Natl. Acad. Sci. U.S.A.* 96: 8633-8.

12. Topalian S L, Gonzales M I, Parkhurst M, et al. (1996) Melanoma-specific CD4+ T cells recognize nonmutated HLA-DR-restricted tyrosinase epitopes *J. Exp. Med.* 183: 1965-1971.

13. Li K, Adibzadeh M, Halder T, et al. (1998) Tumour-specific MHC class-II-restricted responses after in vitro sensitization to synthetic peptides corresponding to gp100 and annexin II eluted from melanoma cells. Cancer *Immunol. Immunother.* 47: 32-8.

14. Chaux P, Vantomme V, Stroobant V, et al. (1999) Identification of MAGE-3 epitopes presented by HLA-DR molecules to CD4(+) T lymphocytes. *J. Exp. Med.* 189: 767-778.

15. Manici S, Sturniolo T, Imro M A, et al. (1999) Melanoma cells present a MAGE-3 epitope to CD4(+) cytotoxic T cells in association with histocompatibility leukocyte antigen DR11. *J. Exp. Med.* 189: 871-876.

16. Wang R-F, Wang X, Atwood A C, Topalian S L, Rosenberg S A. (1999) Cloning genes encoding MHC class II-restricted antigens: mutated CDC27 as a tumor antigen. *Science* 284: 1351-1354.

17. Wang R-F, Wang X, Rosenberg S A. (1999) Identification of a novel MHC class II-restricted tumor antigen resulting from a chromosomal rearrangement recognized by CD4+ T cells. *J. Exp. Med.* 189: 1659-1667.

18. Pieper R, Christian R E, Gonzales M I, et al. (1999) Biochemical identification of a mutated human melanoma antigen recognized by CD4(+) T cells. *J. Exp. Med.* 189: 757-766.

19. Chen Y T, Scanlan M J, Salin U, et al. (1997) A testicular antigen aberrantly expressed in human cancers detected by autologous antibody screening. *Proc. Natl. Acad. Sci. U.S.A.* 94: 1914-1918.

20. Wang R-F, Johnston S L, Zeng G, Schwartzentruber D J, Rosenberg S A. (1998) A breast and melanoma-shared tumor antigen: T cell responses to antigenic peptides translated from different open reading frames. *J. Immunol.* 161: 3596-3606.

21. Jager E, Chen Y T, Drijihout J W, et al. (1998) Simultaneous humoral and cellular immune response against cancer-testis antigen NY-ESO-1: definition of human histocompatibility leukocyte antigen (HLA)-A2-binding peptide epitopes. *J. Exp. Med.* 187: 265-70.

22. Stockert E, Jager E, Chen Y T, et al. (1998) A survey of the humoral immune response of cancer patients to a panel of human tumor antigens. *J. Exp. Med.* 187: 1349-54.

23. Lee L, Wang R-F, Wang X, et al. (1998) NY-ESO-1 may be a potential target for lung cancer immunotherapy. *Cancer J. Sci. Am.* 5: 20-25.

24. Old U J, Chen Y T. (1998) New paths in human cancer serology. *J. Exp. Med.* 187: 1163-7.

25. Wang R F, Mullins J I. (1995) Mammalian cell/vaccinia virus expression vectors with increased stability of retroviral sequences in *Escherichia coli*: production of feline immunodeficiency virus envelope protein. *Gene* 153: 197-202.

26. Ito K, Bian H J, Molina M, et al. (1996) HLA-DR4-IE chimeric class II transgenic, murine class II-deficient mice are susceptible to experimental allergic encephalomyelitis. *J. Exp. Med.* 183: 2635-44.

27. Southwood S, Sidney J, Kondo A, et al. (1998) Several common HLA-DR types share largely overlapping peptide binding repertoires. *J. Immunol.* 160: 3363-73.

28. Sonderstrup G, McDevitt H. (1998) Identification of autoantigen epitopes in MHC class II transgenic mice [In Process Citation]. *Immunol. Rev.* 164: 129-38.

29. Rosenberg S A, White D E. (1996) Vitiligo in patients with melanoma: normal tissue antigens can be targeted for cancer immunotherapy. *J. Immunother.* 19: 81-84.

30. Hara I, Takechi Y, Houghton A N. (1995) inplicating a role for immune recognition of self in tumor rejection: passive immunization aghast the Brown locus protein. *J. Exp. Med.* 182: 1609-1614.

31. Weber L W, Bowne W B, Wolchok J D, et al. (1998) Tumor immunity and autoimmunity induced by immunization with homologous DNA. *J. Clin. Invest.* 102: 1258-64.

32. Overwijk W W, Lee D S, Sunman D R, et al. (1999) Vaccination with a recombinant vaccinia virus encoding a "self" antigen induces autoimmune vitiligo and tumor cell destruction in mice: Requirement for CD4(+) T lymphocytes. *Proc. Natl. Acad. Sci. U.S.A.* 96: 2982-2987.

33. Bowne W B, Srinivasan R, Wolchok J D, et al. (1999) Coupling and Uncoupling of tumor immunity and autoimmunity. *J. Exp. Med.* 190: 1717-1722.

34. Wang R-F, Appella E, Kawakami Y, Kang X, Rosenberg S A. (1996) Identification of TRP-2 as a human tumor antigen recognized by cytotoxic T lymphocytes. *J. Exp. Med.* 184: 2207-2216.

35. Bloom M B, Perry-Lalley D, Robbins P F, et al. (1997) Identification of tyrosinase-related protein 2 as a tumor rejection antigen for the B16 melanoma. *J. Exp. Med.* 185: 453-460.

36. Haas G G J, D'Cruz O J, Bault L E D, (1988) Distribution of human leukocyte antigen-ABC and -D/DR antigens in the unfixed human testis. *Am. J. Reprod. Immunuol. Microbiol.* 18: 47-51.

37. Rosenberg, S. A. 1998. A new era for cancer immunotherapy based on the genes that encode cancer antigens. *Immunity.* 10: 281-287.

38. Wang, R. F. and S. A. Rosenberg. 1999. Human tumor antigens for cancer vaccine development. *Immunol. Rev.* 170: 85-100.

39. Kawakami, Y.; Eliyahu, S.; Delgado, C. H.; Robbins, P. F.; Rivoltini, L.; Topatian, S. L.; Miki, T.; Rosenberg, S. A. 1994. Cloning of the gene coding for a shared human melanoma antigen recognized by autologous T cells infiltrating into tumor. *Proc. Natl. Acad. Sci. U.S.A.* 91: 3515-3519.

40. Wang, R. F., P. F. Robbins, Y. Kawakami, X. Q. Kang, and S. A. Rosenberg. 1995. Identification of a gene encoding a melanoma tumor antigen recognized by HLA-A31-restricted tumor-infiltrating lymphocytes. *J. Exp. Med.* 181: 799-804.

41. Wang, R. F., E. Appella, Y. Kawakami, X. Kang, and S. A. Rosenberg. 1996. Identification of TRP-2 as a human tumor antigen recognized by cytotoxic T lymphocytes. *J. Exp. Med.* 184: 2207-2216.

42. Kawakami, Y., S. Eliyahu, C. H. Delgado, P. F. Robbins, K. Sakaguchi, E. Appella, J. R. Yannelli, G. J. Adema, T.

41. Mikli, and S. A. Rosenberg. 1994. Identification of a human melanoma antigen recognized by tumor-infiltrating lymphocytes associated with in vivo tumor rejection. *Proc. Natl. Acad. Sci. U.S.A.* 91: 6458-6462.
43. van der Bruggen, P., C. Traversari, P. Chomez, C. Lurquin, E. De Plaen, B. Van den Eynde, A. Knuth, and T. Boon. 1991. A gene encoding an antigen recognized by cytolytic T lymphocytes on a human melanoma. *Science* 254: 1643-1647.
44. Chen, Y. T. M. J. Scanlan, U. Sahin, O. Tureci, A. O. Gure, B. Tsang, E. Williamson, E. Stockert, M. Pfreundschuh, L. J. Old. 1997. A testicular antigen aberrantly expressed in human cancers detected by autologous antibody screening. *Proc. Natl. Acad. Sci. U.S.A.* 94: 1914-1918.
45. Wang, R. F., S. L. Johnston, G. Zeng, S. L. Topalian, D. J. Schwartzentruber, and S. A. Rosenberg. 1998. A breast and melanoma-shared tumor antigen: T cell responses to antigenic peptides translated from different open reading frames. *J. Immunol.* 161: 3596-3606.
46. Robbins, P. F., M. El-Gamil, Y. F. Li, Y. Kawakami, D. Loftus, E. Appella, and S. A. Rosenberg. 1995. A mutated beta-catenin gene encodes a melanoma-specific antigen recognized by tumor infiltrating lymphocytes. *J. Exp. Med.* 183: 1185-1192.
47. Jager, E., Y. T. Chen, J. W. Drijfhout, J. Karbach, M. Ringhoffer, D. Jager, M. Arand, H. Wada, Y. Noguchi, E. Stockert, L. J. Old, and A. Knuth. 1998. Simultaneous humoral and cellular immune response against cancer-testis antigen NY-ESO-1: definition of human histocompatibility leukocyte antigen (HLA)-A2-binding peptide epitopes. *J. Exp. Med.* 187: 265-270.
48. Stockert, E., E. Jager, Y. T. Chen, M. J. Scanlan, I. Gout, J. Karbach, M. Arand, A. Knuth, and L. J. Old. 1998. A survey of the humoral immune response of cancer patients to a panel of human tumor antigens. *J. Exp. Med.* 187: 1349-1354.
49. Pardoll, D. M. and S. L. Topalian. 1998. The role of CD4+ T cell responses in antitumor immunity. *Curr. Opin. Immunol.* 10: 588-594.
50. Zeng, G., C. E. Toulouklian, X. Wang, N. P. Restifo, S. A. Rosenberg, and R. F. Wang. 2000. Identification of CD4+ T Cell Epitopes from NY-ESO-1 Presented by HLA-DR Molecules. *J. Immunol* 165: 1153-1159.
51. Jager, E., D. Jager, J. Karbach, Y. T. Chen, G. Ritter, Y. Nagata, S. Gnjatic, E. Stockert, M. Arand, L. J. Old, and A. Knuth. 2000. Identification of NY-ESO-1 epitopes presented by human histocompatibility antigen (HLA)-DRB4*0101-0103 and recognized by CD4(+) T lymphocytes of patients with NY-ESO-1-expressing melanoma. *J. Exp. Med.* 191: 625-630.
52. Gjertson, D. W., L. Geer, S-H. Lee, J. Kawata, and R. Sutrisno. 1997. Population Studies, In HLA 1997. P. Terasaki and D. W. Gjerson, editors. UCLA Tissue Typing Laboratory, Los Angeles, Calif. 174-427.
53. Riley, J. L., S. D. Westerheide, J. A. Price, J. A. Brown, and J. M. Boss. 1995. Activation of class II MHC genes requires both the X box region and the class II transactivator (CIITA). *Immunity* 2: 533-543.
54. Wang, R. F., X. Wang, A. C. Atwood, S. L. Topalian, and S. A. Rosenberg. 1999. Cloning genes encoding MHC class II-restricted antigens: mutated CDC27 as a tumor antigen. *Science* 284: 1351-1354.
55. Walter, E. A., P. D. Greenberg, M. J. Gilbert, R. J. Finch, K. S. Watanabe, E. D. Thomas, and S. R. Riddell. 1995. Reconstitution of cellular immunity against cytomegalovirus in recipients of allogeneic bone marrow by transfer of T-cell clones from the donor. *N. Engl. J. Med.* 333: 1038-1044.
56. Lethe, B., S. Lucas, L. Michaux, C. De Smet, D. Godelaine, A. Serrano, E. De Plaen, T. Boon. 1998. LAGE-1, a new genie with tumor specificity. *Int. J. Cancer.* 76: 903-908.
57. Rammensee, H. G., T. Friede, and S. Stevanovuic. 1995. MHC ligands and peptide motifs: first listing. *Immunogenetics* 41: 178-228.
58. Touloukian, C. E., W. W. Leitner, S. L. Topalian, Y. F. Li, P. F. Robbins, S. A. Rosenberg, and N. P. Restifo. 2000. Identification of a MHC class II-restricted human gp100 epitope using DR41E transgenic mice. *J. Immunol.* 164: 3535-3542.
59. Topalian, S. L., M. I. Gonzales, M. Parkhurst, Y. F. Li, S. Southwood, A. Sette, S. A. Rosenberg, and P. F. Robbins. 1996. Melanoma-specific CD4+ T cells recognize nonmutated HLA-DR-restricted tyrosinase epitopes. *J. Exp. Med.* 183: 1965-1971.

We claim:

1. An isolated cancer epitope of NY-ESO-1, wherein the cancer epitope consists of a sequence selected from the group consisting of SEQ ID NO: 21, 40, and 53-64, wherein the cancer epitope is immunologically recognized by HLA-DP-restricted T lymphocytes.

2. The isolated cancer epitope according to claim 1, wherein the isolated cancer epitope is immunologically recognized by HLA-DPB1*0401 or HLA-DPB1*0402 restricted T lymphocytes.

3. The isolated cancer epitope according to claim 2, wherein the T lymphocytes are CD4+.

4. The isolated cancer epitope according to claim 1, wherein the cancer is selected from the group consisting of: a non-Hodgkins lymphoma, leukemia, Hodgkins lymphoma, lung cancer, liver cancer, metastases, melanoma, head cancer, neck cancer, neuroblastoma, adenocarcinoma, thymoma, colon cancer, uterine cancer, breast cancer, prostate cancer, ovarian cancer, cervical cancer, bladder cancer, kidney cancer, pancreatic cancer, and sarcoma.

5. A pharmaceutical composition comprising at least one cancer epitope according to claim 1 and a pharmaceutically acceptable carrier.

6. An immunogen comprising at least one cancer epitope according to claim 1, alone or in combination with at least one HLA-DP molecule.

7. A target antigen-cancer epitope carrier conjugate comprising a target antigen or target cancer epitope of the target antigen linked to a cancer epitope carrier consisting of a cancer epitope selected from the group consisting of SEQ ID NO: 21, SEQ ID NO: 40, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63 and SEQ ID NO: 64.

8. The isolated cancer epitope of claim 1, wherein the cancer epitope is SEQ ID NO: 54.

9. The immunogen of claim 6, wherein the HLA-DP molecule is an HLA-DPB1*0401 molecule or an HLA-DPB1*0402 molecule.

10. An immunogen comprising an HLA-DP molecule and a cancer epitope of NY-ESO-1 consisting of an amino acid sequence selected from the group consisting of SEQ ID NO: 21, 40, 53-64, and 79, wherein the cancer epitope is immunologically recognized by HLA-DP restricted-T lymphocytes.

11. The immunogen of claim 10, wherein the HLA-DP molecule is an HLA-DPB1*0401 molecule or an HLA-DPB1*0402 molecule.

12. The target antigen-cancer epitope cancer conjugate of claim 7, wherein the target antigen is selected from the group consisting of TRP2, GP100, TRP1, gp120, an HIV antigen, and a malaria antigen.

* * * * *

UNITED STATES PATENT AND TRADEMARK OFFICE
CERTIFICATE OF CORRECTION

PATENT NO. : 7,619,057 B2
APPLICATION NO. : 10/182506
DATED : November 17, 2009
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Twenty-sixth Day of October, 2010

David J. Kappos
*Director of the United States Patent and Trademark Office*

SEQUENCE LISTING

```
<160> NUMBER OF SEQ ID NOS: 80

<210> SEQ ID NO 1
<211> LENGTH: 805
<212> TYPE: DNA
<213> ORGANISM: Homo sapiens

<400> SEQUENCE: 1 agcaggggc   gctgtgtgta   ccgagaatac   gagaatacct   cgtgggccct   gaccttctct        60 ctgagaccg   ggcagaggct   ccggagccat   gcaggccgaa   ggccggggca   caggggttc       120 gacgggcgat   gctgatggcc   caggaggccc   tggcattcct   gatggcccag   ggggcaatgc      180
tggcggccca   ggagaggcgg   gtgccacggg   cggcagaggt   ccccggggcg   cagggggcagc     240 aagggcctcg   gggccgggag   gaggcgcccc   gcggggtccg   catggcggcg   cggcttcagg      300
gctgaatgga   tgctgcagat   gcggggccag   ggggccggag   agccgcctgc   ttgagttcta      360
```

```
cctcgccatg cctttcgcga cacccatgga agcagagctg gcccgcagga gcctggccca    420
ggatgcccca ccgcttcccg tgccaggggt gcttctgaag gagttcactg tgtccggcaa    480
catactgact atccgactca ctgctgcaga ccaccgccaa ctgcagctct ccatcagctc    540
ctgtctccag cagctttccc tgttgatgtg gatcacgcag tgctttctgc ccgtgttttt    600
ggctcagcct ccctcagggc agaggcgcta agcccagcct ggcgccccct cctaggtcat    660
gcctcctccc ctagggaatg gtcccagcac gagtggccag ttcattgtgg gggcctgatt    720
gtttgtcgct ggaggaggac ggcttacatg tttgtttctg tagaaaataa aactgagcta    780
cgaaaaaaaa aaaaaaaaaa aaaaa                                          805

<210> SEQ ID NO 2
<211> LENGTH: 540
<212> TYPE: DNA
<213> ORGANISM: Homo sapiens

<400> SEQUENCE: 2
atgcaggccg aaggccgggg cacaggggt tcgacgggcg atgctgatgg cccaggaggc    60
cctggcattc ctgatggccc aggggggcaat gctggcggcc caggagaggc gggtgccacg   120
ggcggcagag gtcccggggc gcaggggcag caagggcctc ggggccggga ggaggcgccc   180
cgcggggtcc gcatggcggc gcggcttcag ggctgaatgg atgctgcaga tgcggggcca   240
gggggccgga gagccgcctg cttgagttct acctcgccat gcctttcgcg cacccatgg    300 aagcagagct ggcccgcagg agcctggccc aggatgcccc accgcttccc gtgccagggg   360
tgcttctgaa ggagttcact gtgtccggca acatactgac tatccgactc actgctgcag   420
accaccgcca actgcagctc tccatcagct cctgtctcca gcagctttcc ctgttgatgt   480
ggatcacgca gtgctttctg cccgtgtttt tggctcagcc tccctcaggg cagaggcgct   540

<210> SEQ ID NO 3
<211> LENGTH: 180
<212> TYPE: PRT
<213> ORGANISM: Homo sapiens

<400> SEQUENCE: 3

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160
```

```
Trp Ile Thr Gln Cys Phe Leu Pro Val Phe Leu Ala Gln Pro Pro Ser
                165                 170                 175

Gly Gln Arg Arg
            180

<210> SEQ ID NO 4
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is variable
<220> FEATURE:
<221> NAME/KEY: MISC_FEATURE
<222> LOCATION: (8)..(8)
<223> OTHER INFORMATION: Xaa is variable

<400> SEQUENCE: 4

Xaa Lys Glu Phe Thr Val Ser Xaa
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is no amino acid or variable
<220> FEATURE:
<221> NAME/KEY: MISC_FEATURE
<222> LOCATION: (12)..(12)
<223> OTHER INFORMATION: Xaa is no amino acid or variable

<400> SEQUENCE: 5

Xaa Val Leu Leu Lys Glu Phe Thr Val Ser Gly Xaa
1               5                   10

<210> SEQ ID NO 6
<211> LENGTH: 27
<212> TYPE: PRT
<213> ORGANISM: Artificial Sequence
<220> FEATURE:
<223> OTHER INFORMATION: Synthetic

<400> SEQUENCE: 6

Gln Asp Ala Pro Pro Leu Pro Val Pro Gly Val Leu Leu Lys Glu Phe
1               5                   10                  15

Thr Val Ser Gly Asn Ile Leu Thr Ile Arg Leu
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic

<400> SEQUENCE: 7

Ala Pro Pro Leu Pro Val Pro Gly Val Leu Leu Lys Glu Phe Thr Val
1               5                   10                  15

Ser Gly Asn Ile Leu Thr Ile Arg Leu
```

```
                    20                  25

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Ala Pro Pro Leu Pro Val Pro Gly Val Leu Leu Lys Glu Phe Thr Val
1               5                   10                  15

Ser

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Ala Pro Pro Leu Pro Val Pro Gly Val Leu Leu Lys Glu Phe Thr Val
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Leu Pro Val Pro Gly Val Leu Leu Lys Glu Phe Thr Val Ser Gly
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Pro Val Pro Gly Val Leu Leu Lys Glu Phe Thr Val Ser Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Val Pro Gly Val Leu Leu Lys Glu Phe Thr Val Ser Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13
```

```
Pro Gly Val Leu Leu Lys Glu Phe Thr Val Ser Gly
1               5                   10
```

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

```
Gly Val Leu Leu Lys Glu Phe Thr Val Ser Gly
1               5                   10
```

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

```
Leu Leu Lys Glu Phe Thr Val Ser Gly Asn Ile Leu Thr Ile Arg
1               5                   10                  15
```

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

```
Leu Lys Glu Phe Thr Val Ser Gly Asn Ile Leu Thr Ile Arg Leu
1               5                   10                  15
```

<210> SEQ ID NO 17
<211> LENGTH: 14
<212> TYPE: PRT
<213> ORGANISM: Artificial Sequence
<220> FEATURE:
<223> OTHER INFORMATION: Synthetic

<400> SEQUENCE: 17

```
Lys Glu Phe Thr Val Ser Gly Asn Ile Leu Thr Ile Arg Leu
1               5                   10
```

<210> SEQ ID NO 18
<211> LENGTH: 20
<212> TYPE: PRT
<213> ORGANISM: Artificial Sequence
<220> FEATURE:
<223> OTHER INFORMATION: Synthetic

<400> SEQUENCE: 18

```
Leu Pro Val Pro Gly Val Leu Leu Lys Glu Phe Thr Val Ser Gly Asn
1               5                   10                  15

Ile Leu Thr Ile
            20
```

<210> SEQ ID NO 19
<211> LENGTH: 10
<212> TYPE: PRT
<213> ORGANISM: Artificial Sequence
<220> FEATURE:
<223> OTHER INFORMATION: Synthetic

```
<400> SEQUENCE: 19

Val Leu Leu Lys Glu Phe Thr Val Ser Gly
1               5                   10

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Asp His Arg Gln Leu Gln Leu Ser Ile Ser Ser Cys Leu Gln Gln Leu
1               5                   10                  15

Ser Leu Leu Met
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Trp Ile Thr Gln Cys Phe Leu Pro Val Phe Leu Ala Gln Pro Pro Ser
1               5                   10                  15

Gly Gln Arg Arg
            20

<210> SEQ ID NO 22
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is no amino acid or variable
<220> FEATURE:
<221> NAME/KEY: MISC_FEATURE
<222> LOCATION: (2)..(2)
<223> OTHER INFORMATION: Xaa is Ala, Thr, Val, Leu or Arg
<220> FEATURE:
<221> NAME/KEY: MISC_FEATURE
<222> LOCATION: (3)..(3)
<223> OTHER INFORMATION: Xaa is Ser, Ala, Val, Ile, Leu, Thr
<220> FEATURE:
<221> NAME/KEY: MISC_FEATURE
<222> LOCATION: (11)..(11)
<223> OTHER INFORMATION: Xaa is Arg or Lys

<400> SEQUENCE: 22

Xaa Xaa Xaa Gly Pro Gly Gly Gly Ala Pro Xaa
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Ala Ser Gly Pro Gly Gly Gly Ala Pro Arg
1               5                   10
```

```
<210> SEQ ID NO 24
<211> LENGTH: 80
<212> TYPE: DNA
<213> ORGANISM: Artificial Sequence
<220> FEATURE:
<223> OTHER INFORMATION: Synthetic

<400> SEQUENCE: 24
caggatgccc caccgcttcc cgtgccaggg gtgcttctga aggagttcac tgtgtccggc      60
aacatactga ctatcgactc                                                  80

<210> SEQ ID NO 25
<211> LENGTH: 60
<212> TYPE: DNA
<213> ORGANISM: Artificial Sequence
<220> FEATURE:
<223> OTHER INFORMATION: Synthetic

<400> SEQUENCE: 25
agaccaccgc caactgcagc tctccatcag ctcctgtctc cagcagcttt ccctgttgat      60

<210> SEQ ID NO 26
<211> LENGTH: 60
<212> TYPE: DNA
<213> ORGANISM: Artificial Sequence
<220> FEATURE:
<223> OTHER INFORMATION: Synthetic

<400> SEQUENCE: 26
tggatcacgc agtgctttct gcccgtgttt ttggctcagc ctccctcagg gcagaggcgc      60

<210> SEQ ID NO 27
<211> LENGTH: 211
<212> TYPE: DNA
<213> ORGANISM: Artificial Sequence
<220> FEATURE:
<223> OTHER INFORMATION: Synthetic

<400> SEQUENCE: 27
caggatgccc caccgcttcc cgtgccaggg gtgcttctga aggagttcac tgtgtccggc      60
aacatactga ctatccgact cactgctgca gaccaccgcc aactgcagct ctccatcagc     120
tcctgtctcc agcagctttc cctgttgatg tggatcacgc agtgctttct gcccgtgttt     180
ttggctcagc ctccctcagg gcagaggcgc t                                    211

<210> SEQ ID NO 28
<211> LENGTH: 18
<212> TYPE: DNA
<213> ORGANISM: Artificial Sequence
<220> FEATURE:
<223> OTHER INFORMATION: Synthetic

<400> SEQUENCE: 28
aaggagttca ctgtctcc                                                    18

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Asp His Arg Gln Leu Gln Leu Ser Ile Ser Ser Cys Leu Gln Gln Leu
```

```
                1               5                  10                  15

Ser

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

Asp His Arg Gln Leu Gln Leu Ser Ile Ser Ser Cys Leu Gln
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic

<400> SEQUENCE: 31

Gln Leu Gln Leu Ser Ile Ser Ser Cys Leu Gln Gln Leu
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Gln Cys Phe Leu Pro Val Phe Leu Ala Gln Pro Pro Ser Gly Gln Arg
1               5                   10                  15

Arg

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Leu Pro Val Phe Leu Ala Gln Pro Pro Ser Gly Gln Arg Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic

<400> SEQUENCE: 34

Cys Phe Leu Pro Val Phe Leu Ala Gln Pro Pro Ser Gly Gln
1               5                   10

<210> SEQ ID NO 35
<211> LENGTH: 31
<212> TYPE: DNA
<213> ORGANISM: Homo sapiens

<400> SEQUENCE: 35
```

-continued

```
gctccggaca tatgcaggcc gaaggccggg g                                    31
```

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36

```
aaggggctcg aggctgggct tagcgcctct                                      30
```

<210> SEQ ID NO 37
<211> LENGTH: 20
<212> TYPE: PRT
<213> ORGANISM: Artificial Sequence
<220> FEATURE:
<223> OTHER INFORMATION: Synthetic

<400> SEQUENCE: 37

Arg Gly Pro Glu Ser Arg Leu Leu Glu Phe Tyr Leu Ala Met Pro Phe
1               5                   10                  15

Ala Thr Pro Met
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Phe Thr Val Ser Gly Asn Ile Leu Thr Ile Arg Leu Thr Ala Ala Asp
1               5                   10                  15

His Arg Gln Leu
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Asn Ile Leu Thr Ile Arg Leu Thr Ala Ala Asp His Arg Gln Leu Gln
1               5                   10                  15

Leu Ser Ile Ser
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic

<400> SEQUENCE: 40

Leu Ser Leu Leu Met Trp Ile Thr Gln Cys Phe Leu Pro Val Phe Leu
1               5                   10                  15

Ala Gln Pro Pro
            20

```
<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Gln Leu Ser Ile Ser Ser Cys Leu Gln Gln Leu Ser Leu Leu Met Trp
1               5                   10                  15

Ile Thr Gln Cys
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic

<400> SEQUENCE: 42

Gln Asp Ala Pro Pro Leu Pro Val Pro Gly Val Leu Leu Lys Glu Phe
1               5                   10                  15

Thr Val Ser Gly
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic

<400> SEQUENCE: 43

Tyr Leu Ala Met Pro Phe Ala Thr Pro Met Glu Ala Glu Leu Ala Arg
1               5                   10                  15

Arg Ser Leu Ala
            20

<210> SEQ ID NO 44
<211> LENGTH: 15
<212> TYPE: PRT
<213> ORGANISM: Artificial Sequence
<220> FEATURE:
<223> OTHER INFORMATION: Synthetic

<400> SEQUENCE: 44

Ala Pro Pro Leu Pro Val Pro Gly Val Leu Leu Lys Glu Phe Thr
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Ala Pro Pro Leu Pro Val Pro Gly Val Leu Leu Lys Glu Phe
1               5                   10

<210> SEQ ID NO 46
<211> LENGTH: 13
<212> TYPE: PRT
<213> ORGANISM: Artificial Sequence
<220> FEATURE:
```

```
<223> OTHER INFORMATION: Synthetic

<400> SEQUENCE: 46

Ala Pro Pro Leu Pro Val Pro Gly Val Leu Leu Lys Glu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Ala Pro Pro Leu Pro Val Pro Gly Val Leu Leu Lys
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Ala Pro Pro Leu Pro Val Pro Gly Val Leu Leu
1               5                   10

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Pro Pro Leu Pro Val Pro Gly Val Leu Leu Lys Glu Phe Thr Val Ser
1               5                   10                  15

Gly

<210> SEQ ID NO 50
<211> LENGTH: 16
<212> TYPE: PRT
<213> ORGANISM: Artificial Sequence
<220> FEATURE:
<223> OTHER INFORMATION: Synthetic

<400> SEQUENCE: 50

Pro Ile Pro Val Pro Gly Val Leu Leu Lys Glu Phe Thr Val Ser Gly
1               5                   10                  15

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is variable or Trp, Phe, Tyr, Met, Ile,
      Val, or Ala or a combination thereof.
<220> FEATURE:
<221> NAME/KEY: MISC_FEATURE
<222> LOCATION: (5)..(5)
<223> OTHER INFORMATION: Xaa is variable or Cys, Ser, Val, Ala, or Thr
      or a combination thereof.
<220> FEATURE:
```

```
<221> NAME/KEY: MISC_FEATURE
<222> LOCATION: (7)..(7)
<223> OTHER INFORMATION: Xaa is variable or Leu, Phe, Tyr, Met, Ile,
      Val, or Ala or a combination thereof.
<220> FEATURE:
<221> NAME/KEY: MISC_FEATURE
<222> LOCATION: (9)..(9)
<223> OTHER INFORMATION: Xaa is variable or Val, Tyr, Ile, Ala, Leu,
      or Pro or a combination thereof.

<400> SEQUENCE: 51

Xaa Ile Thr Gln Xaa Phe Xaa Pro Xaa
1               5

<210> SEQ ID NO 52
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is no amino acid or variable amino acids.
<220> FEATURE:
<221> NAME/KEY: MISC_FEATURE
<222> LOCATION: (12)..(12)
<223> OTHER INFORMATION: Xaa is no amino acid or variable amino acids.

<400> SEQUENCE: 52

Xaa Trp Ile Thr Gln Cys Phe Leu Pro Val Phe Xaa
1               5                   10

<210> SEQ ID NO 53
<211> LENGTH: 27
<212> TYPE: PRT
<213> ORGANISM: Artificial Sequence
<220> FEATURE:
<223> OTHER INFORMATION: Synthetic

<400> SEQUENCE: 53

Ser Cys Leu Gln Gln Leu Ser Leu Leu Met Trp Ile Thr Gln Cys Phe
1               5                   10                  15

Leu Pro Val Phe Leu Ala Gln Pro Pro Ser Gly
            20                  25

<210> SEQ ID NO 54
<211> LENGTH: 14
<212> TYPE: PRT
<213> ORGANISM: Artificial Sequence
<220> FEATURE:
<223> OTHER INFORMATION: Synthetic

<400> SEQUENCE: 54

Ser Leu Leu Met Trp Ile Thr Gln Cys Phe Leu Pro Val Phe
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetic

<400> SEQUENCE: 55

Leu Leu Met Trp Ile Thr Gln Cys Phe Leu Pro Val Phe Leu
1               5                   10
```

```
<210> SEQ ID NO 56
<211> LENGTH: 14
<212> TYPE: PRT
<213> ORGANISM: Artificial Sequence
<220> FEATURE:
<223> OTHER INFORMATION: Synthetic

<400> SEQUENCE: 56

Leu Met Trp Ile Thr Trp Cys Phe Leu Pro Val Phe Leu Ala
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic

<400> SEQUENCE: 57

Met Trp Ile Thr Gln Cys Phe Leu Pro Val Phe Leu Ala Gln
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic

<400> SEQUENCE: 58

Trp Ile Thr Gln Cys Phe Leu Pro Val Phe Leu Ala Gln Pro
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Synthetic

<400> SEQUENCE: 59

Ile Thr Gln Cys Phe Leu Pro Val Phe Leu Ala Gln Pro Pro
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetic

<400> SEQUENCE: 60

Gln Gln Leu Ser Leu Leu Met Trp Ile Thr Gln Cys Phe Leu
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic

<400> SEQUENCE: 61

Gln Leu Ser Leu Leu Met Trp Ile Thr Gln Cys Phe Leu Pro
1               5                   10

<210> SEQ ID NO 62
```

```
<211> LENGTH: 14
<212> TYPE: PRT
<213> ORGANISM: Artificial Sequence
<220> FEATURE:
<223> OTHER INFORMATION: Synthetic

<400> SEQUENCE: 62

Leu Ser Leu Leu Met Trp Ile Thr Gln Cys Phe Leu Pro Val
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic

<400> SEQUENCE: 63

Arg Ser Leu Leu Met Trp Ile Thr Gln Cys Phe Leu Pro Val
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic

<400> SEQUENCE: 64

Ser Leu Leu Met Trp Ile Thr Gln Cys Phe Leu Pro Val Arg
1               5                   10

<210> SEQ ID NO 65
<211> LENGTH: 18
<212> TYPE: PRT
<213> ORGANISM: Artificial Sequence
<220> FEATURE:
<223> OTHER INFORMATION: Synthetic

<400> SEQUENCE: 65

Val Leu Leu Lys Glu Phe Thr Val Ser Gly Asn Ile Leu Thr Ile Arg
1               5                   10                  15

Leu Thr

<210> SEQ ID NO 66
<211> LENGTH: 18
<212> TYPE: PRT
<213> ORGANISM: Artificial Sequence
<220> FEATURE:
<223> OTHER INFORMATION: Synthetic

<400> SEQUENCE: 66

Ala Ala Asp His Arg Gln Leu Gln Leu Ser Ile Ser Ser Cys Leu Gln
1               5                   10                  15

Gln Leu

<210> SEQ ID NO 67
<211> LENGTH: 14
<212> TYPE: PRT
<213> ORGANISM: Artificial Sequence
<220> FEATURE:
<223> OTHER INFORMATION: Synthetic

<400> SEQUENCE: 67

Thr Gln Cys Phe Leu Pro Val Phe Leu Ala Gln Pro Pro Ser
1               5                   10
```

<210> SEQ ID NO 68
<211> LENGTH: 14
<212> TYPE: PRT
<213> ORGANISM: Artificial Sequence
<220> FEATURE:
<223> OTHER INFORMATION: Synthetic

<400> SEQUENCE: 68

Gln Cys Phe Leu Pro Val Phe Leu Ala Gln Pro Pro Ser Gly
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Synthetic

<400> SEQUENCE: 69

Leu Gln Gln Leu Ser Leu Leu Met Trp Ile Thr Gln Cys Phe
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic

<400> SEQUENCE: 70

Cys Leu Gln Gln Leu Ser Leu Leu Met Trp Ile Thr Gln Cys
1               5                   10

<210> SEQ ID NO 71
<211> LENGTH: 14
<212> TYPE: PRT
<213> ORGANISM: Artificial Sequence
<220> FEATURE:
<223> OTHER INFORMATION: Synthetic

<400> SEQUENCE: 71

Ser Cys Leu Gln Gln Leu Ser Leu Leu Met Trp Ile Thr Gln
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Synthetic

<400> SEQUENCE: 72

Ser Cys Leu Gln Gln Leu Ser Leu Leu Met Trp Ile Thr
1               5                   10

<210> SEQ ID NO 73
<211> LENGTH: 32
<212> TYPE: DNA
<213> ORGANISM: Artificial Sequence
<220> FEATURE:
<223> OTHER INFORMATION: Synthetic

<400> SEQUENCE: 73
cattgctagc atgcaggccg aaggccgggg ca                               32

```
<210> SEQ ID NO 74
<211> LENGTH: 38
<212> TYPE: DNA
<213> ORGANISM: Artificial Sequence
<220> FEATURE:
<223> OTHER INFORMATION: Synthetic

<400> SEQUENCE: 74
aaggctacat tgcggccgct tagcgcctct gccctgag                          38

<210> SEQ ID NO 75
<211> LENGTH: 22
<212> TYPE: DNA
<213> ORGANISM: Artificial Sequence
<220> FEATURE:
<223> OTHER INFORMATION: Synthetic

<400> SEQUENCE: 75
atgcgccctg aacacagaat gt                                           22

<210> SEQ ID NO 76
<211> LENGTH: 26
<212> TYPE: DNA
<213> ORGANISM: Artificial Sequence
<220> FEATURE:
<223> OTHER INFORMATION: Synthetic

<400> SEQUENCE: 76
tcacagggtc ccctgggccc gggga                                        26

<210> SEQ ID NO 77
<211> LENGTH: 22
<212> TYPE: DNA
<213> ORGANISM: Artificial Sequence
<220> FEATURE:
<223> OTHER INFORMATION: Synthetic

<400> SEQUENCE: 77
atgatggttc tgcaggtttc tg                                           22

<210> SEQ ID NO 78
<211> LENGTH: 25
<212> TYPE: DNA
<213> ORGANISM: Artificial Sequence
<220> FEATURE:
<223> OTHER INFORMATION: Synthetic

<400> SEQUENCE: 78
ttatgcagat cctcgttgaa ctttc                                        25

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Ser Leu Leu Met Trp Ile Thr Gln Cys Phe Leu
 1               5                   10

<210> SEQ ID NO 80
<211> LENGTH: 10
<212> TYPE: PRT
```

```
-continued

<213> ORGANISM: Artificial Sequence
<220> FEATURE:
<223> OTHER INFORMATION: Synthetic

<400> SEQUENCE: 80

Trp Ile Thr Gln Cys Phe Leu Pro Val Phe
1               5                   10
```